US007053182B2

(12) United States Patent
Wagner et al.

(10) Patent No.: US 7,053,182 B2
(45) Date of Patent: May 30, 2006

(54) GENES REGULATING CIRCADIAN CLOCK FUNCTIONAL AND PHOTOPERIODISM

(75) Inventors: Ry Wagner, Eugene, OR (US); Karen A. Hicks, Mt. Vernon, OH (US); Michelle T. Z. Spence, Capitola, WA (US); Henriette Foss, Eugene, OR (US); Xiang Liang Liu, Eugene, OR (US); Michael F. Covington, San Diego, CA (US)

(73) Assignee: State of Oregon Acting by and through the State Board of Higher Education on behalf of the University of Oregon, Eugene, OR (US)

( * ) Notice: Subject to any disclaimer, the term of this patent is extended or adjusted under 35 U.S.C. 154(b) by 0 days.

(21) Appl. No.: 11/109,077

(22) Filed: Apr. 18, 2005

(65) Prior Publication Data

US 2005/0204424 A1     Sep. 15, 2005

Related U.S. Application Data

(60) Division of application No. 10/719,885, filed on Nov. 21, 2003, now Pat. No. 6,903,192, which is a division of application No. 09/746,801, filed on Dec. 20, 2000, now Pat. No. 6,689,940, which is a continuation-in-part of application No. 09/513,057, filed on Feb. 24, 2000, now Pat. No. 6,433,251, which is a continuation-in-part of application No. PCT/US99/18747, filed on Aug. 17, 1999.

(60) Provisional application No. 60/096,802, filed on Aug. 17, 1998.

(51) Int. Cl.
*C07K 14/00* (2006.01)
*C07K 16/00* (2006.01)

(52) U.S. Cl. .................................. 530/350; 530/387.9
(58) Field of Classification Search ................. 530/350, 530/387.9
See application file for complete search history.

(56) References Cited

U.S. PATENT DOCUMENTS

| 4,990,607 | A | 2/1991 | Katagiri et al. |
| 5,563,032 | A | 10/1996 | Fields et al. |
| 5,811,536 | A | 9/1998 | Yanofsky |
| 6,002,069 | A | 12/1999 | Yanofsky |

FOREIGN PATENT DOCUMENTS

WO    WO 00/09658    2/2000

OTHER PUBLICATIONS

Carré, "ELF3: a circadian safeguard to buffer effects of light," *Plant Science* 7(1):4-6, 2002.

Chen et al., "Minimal regions in the *Arabidopsis pistillata* promoter responsive to the *Apetala3/pistillata* feedback control do not contain a CArG box," *Sex Plant Reprod.*, pp. 85-94, 2000.
Covington et al., "ELF3 modulates resetting of the circadian clock in *Arabidopsis,*" *Plant Cell* 13:1305-1315, 2001.
Donald et al., "Mutation of either G box or I box sequences profoundly affects expression from the *Arabidopsis* rbcS-1A promoter," *The EMBO Journal* 9(6):1717-1726, 1990.
GardenWeb Glossary of Botanical Terms, at glossary.gardenweb.com/glossary/, accessed Jan. 6, 2003.
Foden-Vencil, "Oregon research team studies genetic manipulation of plants," *Oregonian* Science section, 1992.
"UO Molecular Biologist Studying Genes that Make Plants Flower," *Advance Science & Technology Institute*, University of Oregon, p. 5, 1994.
Hicks et al., "*Arabidopsis* early-flowering mutants reveal multiple levels of regulation in the vegetative-to-floral transition," *Cell Dev. Biol.*, 7:409-418, 1996.
Hicks et al., "Early flowering3 encodes a novel protein that regulates circadian clock function and flowering in *Arabidopsis,*" *The Plant Cell* 13:1281-1292, 2001.
Hicks et al., "Conditional Circadian Dysfunction of the *Arabidopsis* early-flowering 3 Mutant," *Science*, 274:790-792, 1996.
Hill et al., "Functional analysis of conserved histidines in ADP-glucose pyrophosphorylase from *Escherichia coli,*" *Biochemical and Biophysical* 244:573-577, 1998.
Lazar et al., "Transforming growth factor α: mutation of aspartic acid 47 and leucine 48 results in different biological activities," *Molecular and Cellular Biology* 8:1247-1252, 1988.
Newman et al., 21244 CD4-14 *Arabidopsis thaliana* cDNA clone F5H5T3, GenBank Accession # N96569, 1998.
Puzio et al., "A New Nematode Responsible Gene in *Arabidopsis thaliana,*" Database SPTREML-11, O04419, 1997.
Puzio et al., "Isolation of gene from *Arabidopsis thaliana* related to nematode feeding structures," *Gene*, 239:163-175, 1999.
Puzio et al., Nematode Responsive Protein, EMBL Accession No. Y11994, 1997.
Puzio et al., Database Genebank, Accession No. O04419, 1997.
Rounsley et al., GenBank Accession No. B28787, 1997.
Schaffer et al., "The late elongated hypocotyl Mutation of *Arabidopsis* Disrupts Circadian Rhythms and the Photoperiodic Control of Flowering," *Cell* 93:1219-1229, 1998.

(Continued)

*Primary Examiner*—Celian Qian
*Assistant Examiner*—Tara L. Garvey
(74) *Attorney, Agent, or Firm*—Klarquist Sparkman, LLP

(57) ABSTRACT

Nucleic acid molecules that encode plant proteins involved in photoperiodism and circadian rhythms are disclosed. These molecules may be introduced into plants in order to alter the photoperiodic and/or circadian clock-based gene expression of the plants.

6 Claims, 6 Drawing Sheets

OTHER PUBLICATIONS

Shannon et al., "A Mutation in the *Arabidopsis* TFLI Gene Affects Inflorescence Meristem Development," *The Plant Cell* 3:877-892, 1991.

Town et al., Accession No. BH456629, Dec. 12, 2001.

Tymms et al., "A novel epithelial-expressed ETS gene, ELF3: human and murine cDNA sequences, murine genomic organization, human mapping to 1q32.2 and expression in tissues and cancer," *Oncogene* 15:2449-2462, 1997.

Wang and Tobin, "Constitutive Expression of the Circadian Clock Associated 1 (CCA1) Gene Disrupts Circadian Rhythms and Suppresses Its Own Expression," *Cell*, 93:1207-1217, 1998.

Weigel et al., "LEAFY Controls Floral Meristem Identity in *Arabidopsis*," *Cell* 69:843-859, 1992.

Zagotta et al., "The *Arabidopsis* ELF3 gene regulates vegetative photomorphogenesis and the photoperiodic induction of flowering," *Plant J.* 10(4);691-702, 1996.

Zagotta et al., "Early-flowering Mutants of *Arabidopsis thaliana*," *Aust. J. Plant Physiol.*, 19:411-418,1992.

FIG. 1 (Part 1)

FIG. 1 (Part 2)

FIG. 1 (Part 3)

FIGURE 2

```
BLOCK I:
AtELP3         13  PMFPRLHVHD ADKGG-PRAP PRNKMALYEQ LSIPSQFF  49
AtEEC          15  PLFPRVHVHD TGRGG-LSQQ FDGKTMSLVS SKRFNLPS  49
cardamineELP3  13  PMFPRLHVHD ADEGG-PRAP PRNKMALYEQ LSIPSERF  49
tomatoELP3     13  PMFPRLNVHD TBKGG-PRAP PRNKMALYEQ LSIPSQFY  49
riceELP3       22  PLFPRLHVHD AARGGGPRAP PRNKMALYEQ FTVPSHRF  59

BLOCK II:
AtELP3         317 SPDDVVGILG QKRFWRARKA IAHQQRVFAV QLFELHRLIK VQKLIAASP  365
AtEEC          238 SSYDIARVIG EKRFWKMRTY MINQQKKFAG QVFELHRLIM VQFMVAKSP  285
cELP3          291 SPDDVVGALG QKRFWRARKA ITHQQRVPAV QLFELHRLIK VQRLIAASP  339
tELP3          341 SPDDIVGIIG LKRFWKARRA IVHQQRVFAH QVFELHRLIK VQRLIAGSP  389
rELP3          394 SPDKIVGAIG TKBFWKARRA IMHQQRVFAV QVFELHKLVK VQKLIAASP  442
maizeELP3      ?   SPDDVVSAIG PKHFWKARRA IVHQQRVFAV QVFELHRLIK VQKLIAASP  ?

BLOCK III:
AtELP3         462 PPPSGNHQQW LIPVMSPSEG LIYKP  469
AtEEC          358 PPP-GH--QW LVPVITDSDG LVYKP  379
cELP3          441 PPPSGH-QQW LIPVMSPSEG LIYKP  464
tELP3          485 QQPSG-H-QW LIPVMSPSEG LVYKP  508
rELP3          544 -QPPQH--QW LVPVMSPLEG LVYKP  565
mELP3          ?   -------QW LIPVMSPSEG LVYKP  ?

BLOCK IV:
AtELP3         660 RVIKVVPHKA KLASENAARI FQSIQEER  691
AtEEC          505 RAIKAVPHHS TSASESAARI FRFIQEER  536
cELP3          577 RVIKVVPHKA KLASEN----  ---------  577
tELP3          677 RVIKVVPHKA HSATESVARI FQSIQQER  704
rELP3          729 NVIKVVPHHS RTASESAARI FRSIQMER  756
mELP3          ?   RVIRVVPHTA RTASESAARI FRSIQMER  ?
```

FIG. 3

Table 1. *Arabidopsis* seedlings overexpressing ELF3 have a reduced sensitivity to red light in hypocotyl elongation and flower late in LD. Mean hypocotyl length in millimeter and flowering time ± SE are indicated. Number of plants measured for each character and genotype is indicated in parenthesis

| Genotype | Hypocotyl Length in millimeter | Flowering Time As Number of Leaves at 1cm Bolt | | Flowering Time As Days to 1cm Bolt | |
|---|---|---|---|---|---|
| | | LD | SD | LD | SD |
| COL-0 | 5.69 ± 0.55 (21) | 10.8 ± 1.36 (20) | 64.60 ± 5.10 (10) | 29.00 ± 2.02 (20) | 102.4 ± 6.41 (10) |
| ELF3-OX | 2.96 ± 0.52 (27) | 42.5 ± 4.42 (16) | 57.03 ± 1.37 (47) | 60.56 ± 7.53 (16) | 96.96 ± 0.92 (47) |
| *elf3-1* | 12.40 ± 0.94 (27) | 5.15 ± 0.73 (20) | 9.65 ± 2.95 (17) | 20.75 ± 1.26 (20) | 47.06 ± 6.59 (17) |
| phyB-9 | 14.69 ± 0.86 (20) | 7.17 ± 1.34 (18) | NA | 25.83 ± 1.98 (18) | NA |
| phyB/ELF3-OX | 10.09 ± 0.70 (19) | 44.07 ± 5.21 (27) | NA | 64.37 ± 9.58 (27) | NA |

FIG. 4

Features of the predicted 695 amino acid ELF3 protein

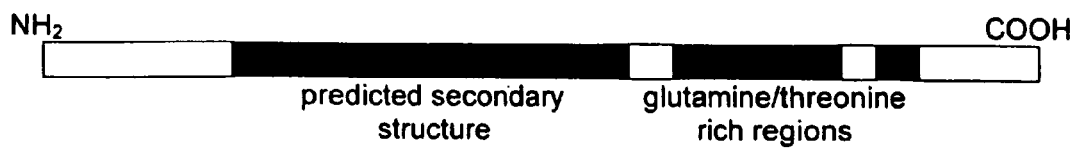

predicted secondary   glutamine/threonine
structure             rich regions

**Molecular basis of the *elf 3* mutations**

| | |
|---|---|
| elf3-1 | C to T change in exon 3 (stop) |
| elf3-2 | ~1.5 kb C-terminal deletion |
| elf3-3 | G to T change in exon 2 (stop) |
| elf3-4 | 11 bp deletion in exon 1 (stop) |
| elf3-5 | C to T change in exon 1 (stop) |
| elf3-6 | AG to AA change in the exon 4 splice acceptor site |
| elf3-7 | G to A change in the exon 1 splice donor site* |
| | *makes ~ 20% full length wild type *ELF3* mRNA |
| elf3-8 | unknown |
| elf3-9 | unknown |

GENES REGULATING CIRCADIAN CLOCK FUNCTIONAL AND PHOTOPERIODISM

CROSS REFERENCE TO RELATED CASES

This is a division of U.S. patent application Ser. No. 10/719,885, filed Nov. 21, 2003, now U.S. Pat. No. 6,903,192, issued Jun. 7, 2005, which is a division of U.S. patent application Ser. No. 09/746,801, filed Dec. 20, 2000, now U.S. Pat. No. 6,689,940, issued Feb. 10, 2004, which is a continuation-in-part of application Ser. No. 09/513,057, filed Feb. 24, 2000, now U.S. Pat. No. 6,433,251, issued Aug. 13, 2002, which is a continuation-in-part of International Application No. PCT/US99/18747, filed Aug. 17, 1999, which claims the benefit of Provisional Application No. 60/096,802, filed Aug. 17, 1998. All of these applications are incorporated herein in their entirety.

FIELD OF THE INVENTION

This invention relates to genes that regulate circadian clock functions and photoperiodism in plants, and relates in particular to the ELF3 gene. Aspects of the invention include the purified ELF3 gene product (ELF3 protein), as well as nucleic acid molecules encoding this gene product. Nucleic acid vectors, transgenic cells, and transgenic plants having modified ELF3 activity are also provided.

INCORPORATION-BY-REFERENCE OF MATERIAL SUBMITTED ON COMPACT DISC

A Sequence Listing is provided in electronic format only on compact discs, as permitted under 37 CFR 1.52(e) and 1.821(c). The discs (copy 1 and copy 2) contain the file entitled "Sequence Listing.txt" (218 KB). The material on these discs is hereby incorporated by reference in its entirety.

BACKGROUND OF THE INVENTION

Shoot development in flowering plants is a continuous process ultimately controlled by the activity of the shoot apical meristem. Apical meristem activity during normal plant development is sequential and progressive, and can be summarized as a series of overlapping phases: vegetative→inflorescence→floral (V→I→F). Over the past 50 years many models have been proposed for the control of the vegetative-to-floral transition. These models range from simple single pathway models to complex multiple pathway models, and are largely based on physiological studies (for review, see Bernier, 1988). Modern techniques provide researchers with genetic and molecular methods that can be used to further investigate the control of V→I→F transitions.

One such modern technique now routinely practiced by plant molecular biologists is the production of transgenic plants carrying a heterologous gene sequence. Methods for incorporating an isolated gene sequence into an expression cassette, producing plant transformation vectors, and transforming many types of plants are well known. Examples of the production of transgenic plants having modified characteristics as a result of the introduction of a heterologous transgene include: U.S. Pat. No. 5,268,526 (modification of phytochrome expression in transgenic plants); U.S. Pat. No. 5,719,046 (production of herbicide resistant plants by introduction of bacterial dihydropteroate synthase gene); U.S. Pat. No. 5,231,020 (modification of flavenoids in plants); U.S. Pat. No. 5,583,021 (production of virus resistant plants); and U.S. Pat. Nos. 5,767,372 and 5,500,365 (production of insect resistant plants by introducing *Bacillus thuringiensis* genes).

Light quality, photoperiod, and temperature often act as important, and for some species essential, environmental cues for the initiation of flowering. However, there is very little information on the molecular mechanisms that directly regulate the developmental pathway from reception of the inductive light signal(s) to the onset of flowering and the initiation of floral meristems. The analysis of floral transition mutants in pea (*Pisum sativum*) (see Murfet, 1985) and *Arabidopsis* (see Koornneef et al., 1991) has demonstrated that at least part of the genetic hierarchy controlling flowering onset is responsive to the number of hours of light perceived by a plant within a 24 hour light/dark cycle. The monitoring of the length of the light period is referred to as the photoperiodic response. Photoperiodic responses have long been thought to be tied to one or more biological clocks that regulate many physiological and developmental processes on the basis of an endogenous circadian rhythm.

Many important physiological and developmental plant processes are influenced by circadian rhythms. These include the induction of gene transcription, leaf movement, stomatal opening, and the photoperiodic control of flowering. While the relationship of these plant processes to the circadian rhythm has long been recognized, the genetic analysis of circadian rhythms in plants has only recently begun. Most of the genetic analysis of circadian regulation has been performed with *Drosophila* and *Neurospora crassa*, where mutational studies have led to the isolation of the per and frq genes, respectively (Hall, 1990; Dunlap, 1993). These genes are thought to encode components of the circadian oscillator, in part because, while null alleles cause arrhythmic responses, alleles of these genes exist that produce either long or short period responses. Transcriptional production of per and frq mRNA cycles on a twenty-four hour period, and both genes regulate their own expression (Edery et al., 1994; Aronson et al., 1994).

*Arabidopsis* is a quantitative long-day (LD) plant—wild-type plants will initiate flowering more quickly when grown under LD light conditions than when grown under short-day (SD) light conditions. In order to identify genes required for floral initiation and development, populations of *Arabidopsis thaliana* ecotype Columbia grown in SD conditions have been screened for early-flowering mutants. Isolated mutants were then examined for additional shoot development anomalies, and those with discreet shoot phenotypes related to meristem function or light perception were considered for further analysis. Such mutants may identify genes that are part of functionally redundant pathways that operate, to varying degrees, as "fail-safe" mechanisms for ensuring shoot growth and reproductive development. Examples of such functionally redundant pathways have been described in studies of *Drosophila* (e.g., Hηlskamp et al., 1990) and *C. elegans* (e.g., Lambie and Kimble, 1991). The key genes identified by these *Arabidopsis* screens were the TERMINAL FLOWER 1 (TFL1) gene and the EARLY-FLOWERING 3 (ELF3) gene (Shannon and Meeks-Wagner, 1991; Zagotta et al., 1992).

The early-flowering (elf3) mutant of *Arabidopsis* is insensitive to photoperiod with regard to floral initiation. Plants homozygous for a mutation in the ELF3 locus flower at the same time in LD and SD growth conditions, whereas floral initiation of wild-type plants is promoted by LD growth conditions (Zagotta et al., 1992; Zagotta et al., 1996). In LD conditions, the flowering time of the elf3-1 heterozygote is intermediate between wild-type and the homozygous mutant. In addition to being photoperiod-insensitive, all elf3 mutants display the long hypocotyl phenotype characteristic of plants defective in light reception or the transduction of light signals (Zagotta et al., 1992; Zagotta et al., 1996). The majority of long hypocotyl mutants that have been identified are defective in red light-mediated inhibition of hypocotyl elongation. In contrast, elf3 mutants are primarily defective in blue light-dependent inhibition of hypocotyl elongation, although they are also partially deficient in red light-dependent inhibition of hypocotyl elongation (Zagotta et al., 1996).

The availability of the ELF3 gene would facilitate the production of transgenic plants having altered circadian clock function and programmed photoperiodic responses. It is to such a gene that the present invention is directed.

SUMMARY OF THE INVENTION

The invention provides an isolated ELF3 gene from *Arabidopsis* that is shown to complement the elf3 photoperiod-insensitive flowering and elongated hypocotyl defects when introduced into elf3 mutant plants.

One aspect of this invention is a purified protein having ELF3 protein biological activity. The prototypical *Arabidopsis* ELF3 protein has the amino acid sequence shown in SEQ ID NO: 2. Variants of this protein that differ from SEQ ID NO: 2 by one or more conservative amino acid substitutions are also provided, as are homologs of the ELF3 protein. Such homologs typically share at least 60% sequence identity with the sequence shown in SEQ ID NO: 2. Nucleic acid molecules encoding these proteins are also part of this invention. Such nucleic acid molecules include those having the nucleotide sequences set forth in SEQ ID NO: 1, SEQ ID NO: 3, and SEQ ID NO:4.

Recombinant nucleic acid molecules in which a promoter sequence is operably linked to any of these ELF3 protein-encoding nucleic acid sequences are further aspects of this invention. The invention also provides cells transformed with such a recombinant nucleic acid molecule and transgenic plants comprising the recombinant nucleic acid molecule. Such transgenic plants may be, for instance, *Arabidopsis*, pepper, tomato, tobacco, broccoli, cauliflower, cabbage, canola, bean, soybean, rice, corn, wheat, barley, citrus, cotton, cassava and walnut, trees such as poplar, oak, maple, pine, spruce, and other conifers, and ornamental plants (e.g., petunias, orchids, carnations, roses, impatiens, pansies, lilies, snapdragons, geraniums, and so forth).

A further aspect of this invention is an isolated nucleic acid molecule or oligonucleotide comprising 15, 20, 30, 50, or 100 contiguous nucleotides of the sequence shown in SEQ ID NOs: 1, 3, or 4. Such nucleic acid molecules or oligonucleotides may be operably linked to a promoter sequence, and may be in the sense or antisense orientation in relation to such a promoter. The invention also includes cells and plants transformed with such recombinant nucleic acid molecules, with or without an attached promoter.

Further embodiments of this invention include isolated nucleic acid molecules that hybridize under specified hybridization conditions to the nucleic acid sequence set forth in SEQ ID NO: 1, and that encode a protein having ELF3 protein biological activity. Closely related ELF3 gene homologs may be detected by hybridization under stringent conditions, whereas less closely related homologs may be detected by hybridization at low stringency. Appropriate wash conditions for stringent hybridization may be 55° C., 0.2×SSC and 0.1% SDS for 1 hour. Appropriate wash conditions for low stringency hybridization may be 50° C., 2×SSC, 0.1% for 3 hours. Such a hybridizing isolated nucleic acid molecule may be operably linked to a promoter for expression in plants. Cells transformed with such a recombinant nucleic acid molecule, and transgenic plants that comprise such a molecule, are also provided.

The invention also provides the 5' regulatory region of the ELF3 gene. This regulatory region, or parts thereof, may be used to obtain ELF3-like circadian-rhythm expression of particular genes. For example, the ELF3 5' regulatory region may be operably linked to an open reading frame of a gene of interest, and the resulting recombinant construct may be introduced into a plant by transformation. One embodiment of an ELF3 regulatory region is about nucleotides 1 through about 1900 of the 5' upstream region shown in SEQ ID NO: 5.

BRIEF DESCRIPTION OF THE DRAWINGS

Figure 1:
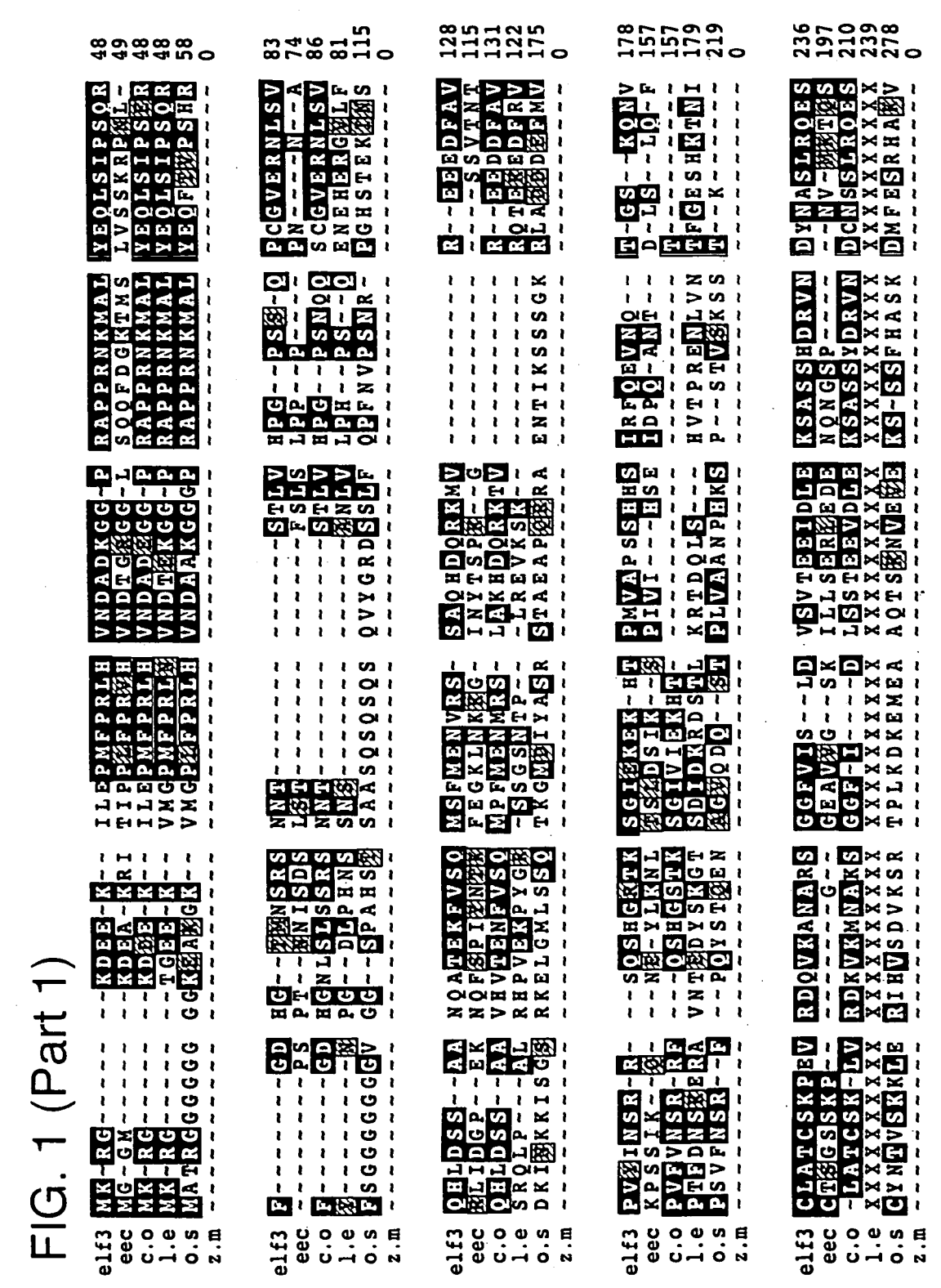
Figure 1:
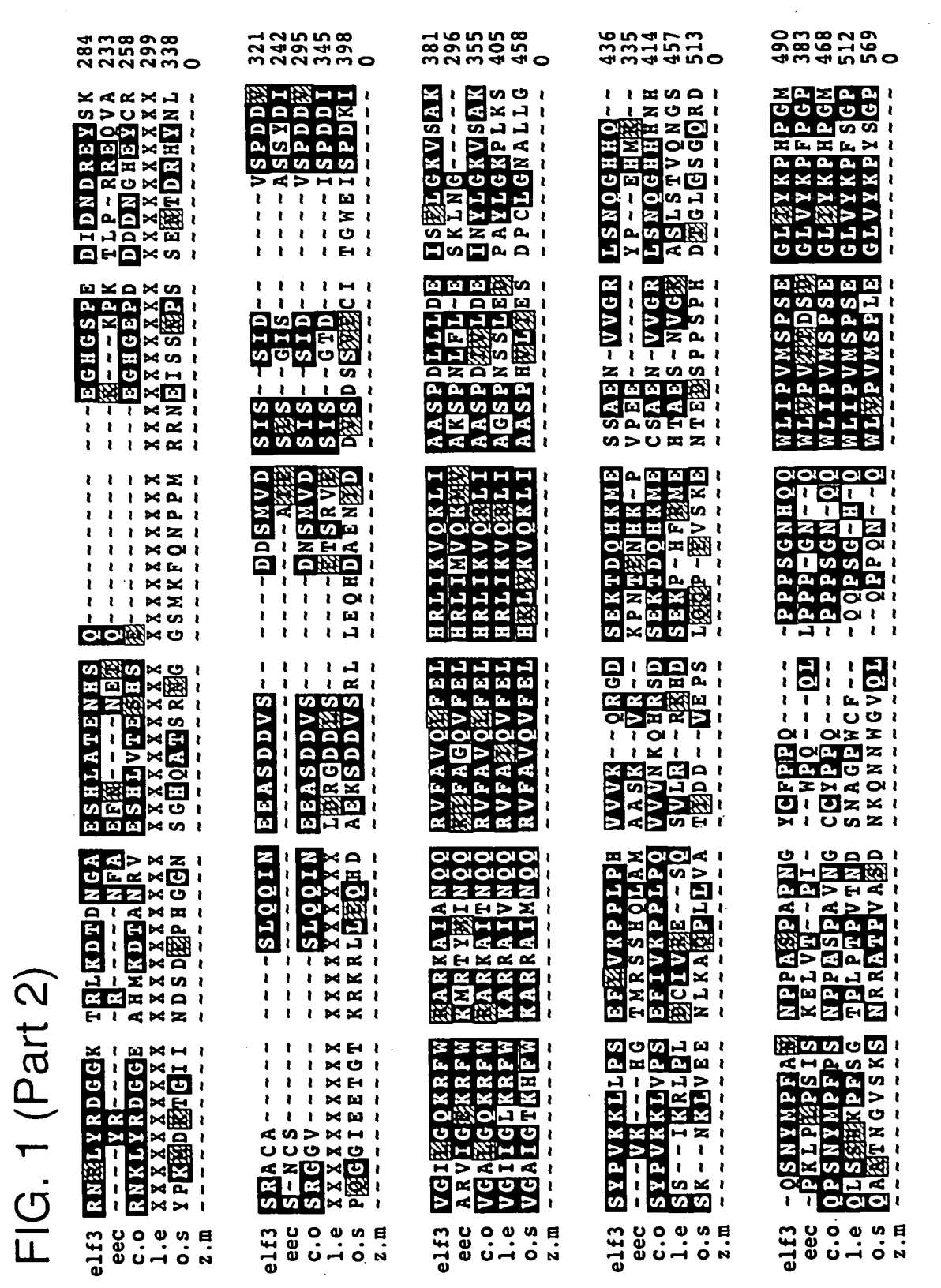
Figure 1:
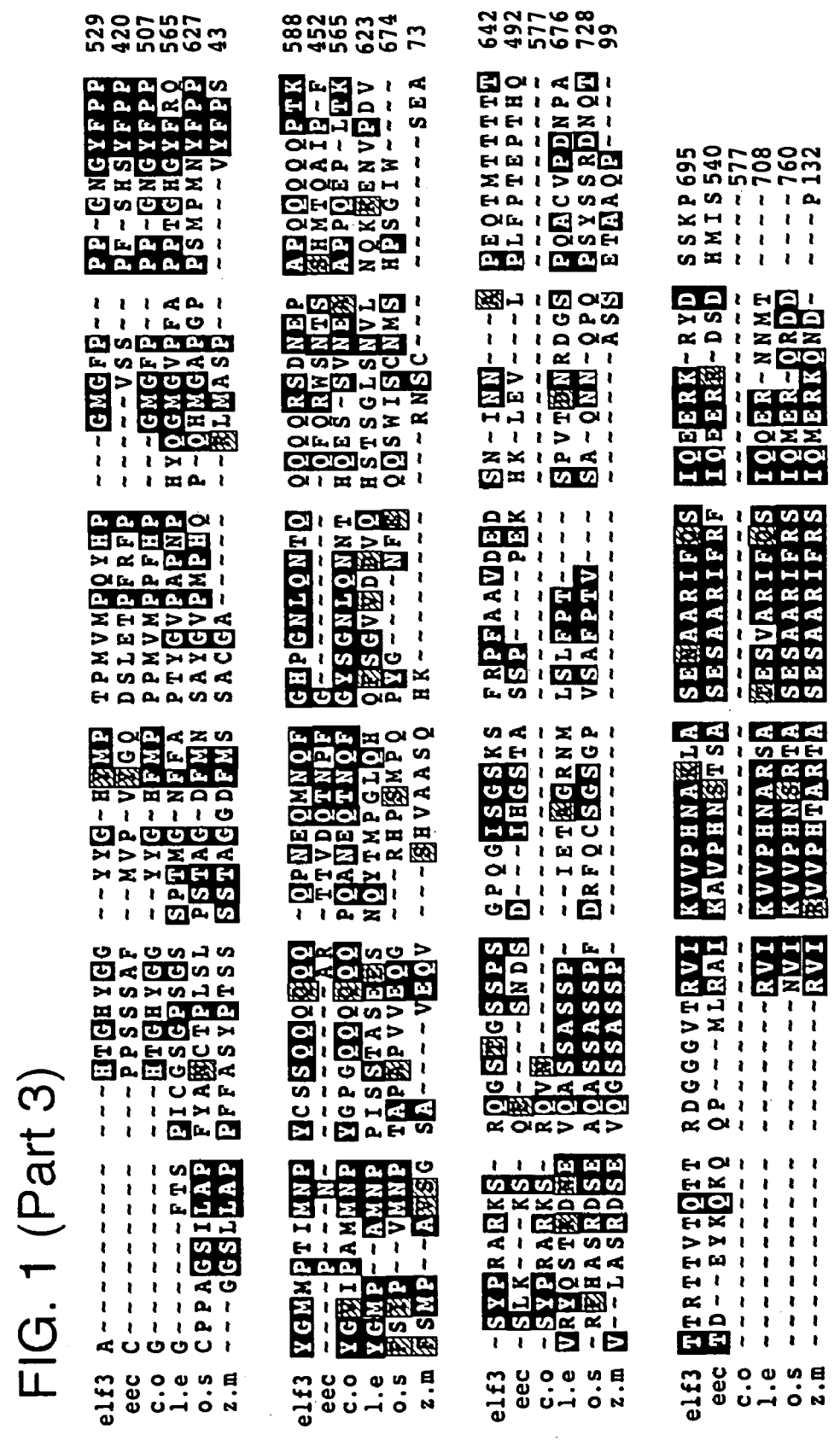

FIG. 1. Sequence Comparison of ELF3 Homologs.

Multiple-sequence alignment of ELF3 (residues 1–695 of SEQ ID NO: 2) and several putative ELF3 homologs from *Arabidopsis thaliana* (Essence of ELF3 Consensus, EEC) (residues 1–540 of SEQ ID NO: 33) and other plant species (*Cardamine oligosperma* (residues 1–577 of SEQ ID NO: 13), tomato (residues 1–179 of SEQ ID NO. 24 and residues 1–389 of SEQ ID NO: 23), rice (residues 1–760 of SEQ ID NO: 27), and maize (residues 117–247 of SEQ ID NO: 29)). Protein designations are given on the left in the same order. Amino acid residues are numbered on the right. Residues shaded in black indicate identity of at least three ELF3/ELF3-related sequences in the alignment; light-shaded residues indicate similarity to consensus. Nucleotide sequences from *C. oligosperma* (a member of the family Brassicaceae) were obtained by sequencing polymerase chain reaction products using degenerate oligos to the *Arabidopsis* ELF3 gene and genomic DNA or cDNA prepared from *C. oligosperma* seedlings. Sequences were aligned and analyzed using CLUSTAL W (J. D. Thompson, D. G. Higgins, T. Gibson, *Nucleic Acids Res.* 22, 4673–80, 1994) and PrettyBox (Genetics Computer Group, Inc., Madison, Wis.).

FIG. 2. Sequence Comparison of ELF3 Homologs Showing Consensus Boxes.

Multiple-sequence alignment shows four highly conserved regions within ELF3 and putative ELF3 homologs from *Arabidopsis thaliana* (Essence of ELF3 Consensus, EEC) and other plant species (*Cardamine oligosperma*, tomato, rice, and maize). Protein designations are given on the left in the same order. Amino acid residues are numbered on both the right and left. Residues shaded in black indicate identity of at least three ELF3/ELF3-related sequences in the alignment; light-shaded residues indicate similarity to consensus. Sequences were aligned and analyzed using CLUSTAL W (J. D. Thompson, D. G. Higgins, T. Gibson, *Nucleic Acids Res.* 22, 4673–80, 1994) and PrettyBox (Genetics Computer Group, Inc., Madison, Wis.).

GenBank accession numbers for ELF3 and putative ELF3 homologs are as follows: AtELF3 (*A. thaliana* genomic DNA: AC004747, published Dec. 17, 1999), AtEEC (*A. thaliana* genomic DNA: AB023045, published Nov. 20, 1999), cELF3 (yet to be submitted), tELF3 *[Lycopersicon esculentum* Expressed Sequence Tags (ESTs) from Clemson University Genomics Institute: AW093790 (Oct. 18, 1999), AI894513 (Jul. 27, 1999), AI488927 (Jun. 29, 1999), AI486934 (Jun. 29, 1999), AI894398 (Jul. 27, 1999)], rELF3 (*Oryza sativa* genomic DNA: AP000399, published Dec. 3, 1999), mELF3 (*Zea mays* EST from Stanford University Genome Center: AI637184, published Apr. 26, 1999).

In Block I, the "AtELF3" amino acid sequence corresponds to residues 13–49 of SEQ ID NO: 2; the "AtEEC" amino acid sequence corresponds to residues 15–51 of SEQ ID NO: 33; the "cardamineELF3" amino acid sequence corresponds to residues 13–49 of SEQ ID NO: 13; the "tomatoELF3" amino acid sequence corresponds to residues 13–49 of SEQ ID NO: 24; and the "riceELF3" amino acid sequence corresponds to residues 22–59 of SEQ ID NO: 27.

In Block II, the "AtELF3" amino acid sequence corresponds to residues 317–365 of SEQ ID NO: 2; the "AtEEC" amino acid sequence corresponds to residues 238–286 of SEQ ID NO: 33; the "cELF3" amino acid sequence corresponds to residues 291–339 of SEQ ID NO: 13; the "tELF3" amino acid sequence corresponds to residues 22–70 of SEQ ID NO: 23; the "rELF3" amino acid sequence corresponds to residues 394–442 of SEQ ID NO: 27; and the "maizeELF3" amino acid sequence corresponds to residues 22–70 of SEQ ID NO: 57.

In Block III, the "AtELF3" amino acid sequence corresponds to residues 462–486 of SEQ ID NO: 2; the "AtEEC" amino acid sequence corresponds to residues 358–379 of SEQ ID NO: 33; the "cELF3" amino acid sequence corresponds to residues 441–464 of SEQ ID NO: 13; the "tELF3" amino acid sequence corresponds to residues 167–189 of SEQ ID NO: 23; the "rELF3" amino acid sequence corresponds to residues 544–565 of SEQ ID NO: 27; and the "mELF3" amino acid sequence corresponds to residues 162–178 of SEQ ID NO: 57.

In Block IV, the "AtELF3" amino acid sequence corresponds to residues 660–687 of SEQ ID NO: 2; the "AtEEC" amino acid sequence corresponds to residues 505–532 of SEQ ID NO: 33; the "cELF3" amino acid sequence corresponds to residues 639–653 of SEQ ID NO: 14; the "tELF3" amino acid sequence corresponds to residues 358–385 of SEQ ID NO: 23; the "rELF3" amino acid sequence corresponds to residues 729–756 of SEQ ID NO: 27; and the "mELF3" amino acid sequence corresponds to residues 285–312 of SEQ ID NO: 57.

FIG. 3 is a Table showing growth and flowering characteristics of *Arabidopsis* seedlings over-expressing ELF3 (ELF3-OX), seedlings that are mutant in ELF3 (elf3-1).

FIG. 4 shows the features of the predicted 695 amino acid ELF3 protein, and the molecular basis of the several elf3 mutations.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 shows the cDNA and amino acid sequence of *Arabidopsis* ELF3.

SEQ ID NO: 2 shows the amino acid sequence of *Arabidopsis* ELF3 protein.

SEQ ID NO: 3 shows the genomic sequence of *Arabidopsis* ELF3. The sequence comprises the following regions:

| Nucleotides | Feature |
|---|---|
| 1–142 | promoter region |
| 143–424 | exon 1(5' UTR) |
| 425–644 | exon 1 continued (initiating ATG at 425) |
| 645–1006 | intron 1 |
| 1007–1803 | exon 2 |
| 1804–2983 | intron 2 |
| 2984–3037 | exon 3 |
| 3038–3127 | intron 3 |
| 3128–4142 | exon 4 |
| 4143–4145 | stop codon |
| 4146–4221 | 3' UTR and 3' regulatory region. |

SEQ ID NO: 4 shows the DNA and corresponding amino acid sequence of the *Arabidopsis* ELF3 ORF.

SEQ ID NO: 5 shows the 4071 base pair *Arabidopsis* ELF3 5' regulatory region.

SEQ ID NO: 6–11 show primers that can be used to amplify certain portions of the *Arabidopsis* ELF3 sequence.

SEQ ID NO: 12 shows the cDNA and corresponding amino acid sequence of the *Cardamine oligosperma* ELF3 ortholog, cELF3. This sequence can also be determined by applying well known computer analyses to the genomic sequence shown in SEQ ID NO: 14 (also referred to as COELF3~1) to determine where the introns and exons are.

SEQ ID NO: 13 (also referred to as COELF3~2) shows the amino acid sequence of the *Cardamine oligosperma* ELF3 ortholog, cELF3.

SEQ ID NO: 14 (also referred to as COELF3~1) shows the genomic sequence of the *Cardamine oligosperma* ELF3 ortholog, cELF3.

SEQ ID NO: 15 shows a partial DNA sequence (also referred to as PEAELF~2) of the pea ELF 3 ortholog.

SEQ ID NO: 16 (also referred to as PEAELF~1) shows the amino acid sequence of the partial pea ELF 3 ortholog.

SEQ ID NO: 17 (also referred to as BROCCA~2) shows the amino acid sequence of the broccoli/cauliflower EEC protein.

SEQ ID NO: 18 shows a partial DNA (also referred to as GMELF3~2) sequence of the *Glycine max* (soybean) ELF3 coding region.

SEQ ID NO: 19 (also referred to as GMELF3~1) shows the amino acid sequence of the partial *Glycine max* (soybean) ELF3 protein.

SEQ ID NO: 20 shows the DNA (also referred to as BROCCA~1) a sequence of the *Lycopersicon esculentum* (tomato) ELF3 (N-terminus #2) coding region.

SEQ ID NO: 21 shows the DNA (also referred to as LEAFFO~1) sequence of the *Lycopersicon esculentum* (tomato) ELF3 (N-terminus #1) coding region.

SEQ ID NO: 22 shows the DNA (also referred to as LE5B39~1) sequence of the *Lycopersicon esculentum* (tomato) coding region.

SEQ ID NO: 23 (also referred to as LEELF3~3) shows the amino acid sequence of the *Lycopersicon esculentum* (tomato) ELF3 (C-terminus) coding region.

SEQ ID NO: 24 (also referred to as LEELF~2) shows a partial amino acid sequence of the *Lycopersicon esculentum* (tomato) protein. SEQ ID NO: 25 (also referred to as LEELF3~1) shows the amino acid sequence of the *Lycopersicon esculentum* (tomato) ELF3 (N-terminus #2) protein.

SEQ ID NO: 26 shows the DNA (also referred to as OSELF3~2) sequence of the *Oryza sativa* (rice) ELF3 genomic region.

SEQ ID NO: 27 (also referred to as OSELF3~1) shows the amino acid sequence of the *Oryza sativa* (rice) ELF3 protein.

SEQ ID NO: 28 shows a partial DNA (also referred to as ZM8CC4~1) sequence of the *Zea mays* (maize) ELF3 coding region.

SEQ ID NO: 29 (also referred to as ZMELF3~2) shows the amino acid sequence of the partial *Zea mays* (maize) ELF3 protein.

SEQ ID NO: 30 shows a partial DNA (also referred to as ZMELF3~4) sequence of the *Zea mays* (maize) ELF3 #2 coding region.

SEQ ID NO: 31 (also referred to as ZMELF3~3) shows the amino acid sequence of the partial *Zea mays* (maize) ELF3 #2 coding region.

SEQ ID NO: 32 shows the DNA (also known as ATEECG~1) of the *Arabidopsis thaliana* EEC genomic region.

SEQ ID NO: 33 (also known as ATEECP~1) shows the amino acid sequence of the *Arabidopsis thaliana* EEC protein.

SEQ ID NO: 34 shows the DNA (also known as ATELF3~1) sequence of the *Arabidopsis thaliana* ELF3 genomic region.

SEQ ID NO: 35 (also known as ATELF3~2) shows the amino acid sequence of the *Arabidopsis thaliana* ELF3 protein.

SEQ ID NO: 36 (also known as MTELF3N1) shows a portion of exon 1, including 5'UTR and start codon, of the *Medicago trunculata* ELF3 cDNA nucleotide sequence. This partial sequence was originally reported in Genbank Accession No. AW690413.

SEQ ID NO: 37 (also known as MTELF3P1) shows the peptide portion of the *Medicago trunculata* ELF3 protein encoded for by SEQ ID NO: 36.

SEQ ID NO: 38 (also known as MTELF3N4) shows a portion of exon 4, including stop codon and 3'UTR, of the *Medicago trunculata* ELF3 nucleotide sequence. This partial sequence was originally reported as Genbank Accession No. AW693560.

SEQ ID NO: 39 (also known as MTELF3P4) shows the peptide portion of the *Medicago trunculata* ELF3 protein encoded for by SEQ ID NO: 38.

SEQ ID NO: 40 (also known as PSELF3N3) shows a portion of exon 3 to exon 4 of the *Pisum sativa* genomic DNA encoding ELF3.

SEQ ID NO: 41 (also known as PSELF3P3) shows the peptide portion of the *Pisum sativa* ELF3 protein encoded for by SEQ ID NO:40.

SEQ ID NO: 42 (also known as PSELF3N4) shows a portion of exon 4 of the *Pisum sativa* genomic DNA encoding ELF3.

SEQ ID NO: 43 (also known as PSELF3P4) shows the peptide portion of the *Pisum sativa* ELF3 protein encoded for by SEQ ID NO: 42.

SEQ ID NO: 44 (also known as GMELF3N) shows a portion of the *Glycine max* cDNA encoding ELF3. This partial sequence was originally reported in Genbank Accession No. AW757137.

SEQ ID NO: 45 (also known as GMELF3P) shows the peptide portion of the *Glycine max* ELF3 protein encoded for by SEQ ID NO: 44.

SEQ ID NO: 46 (also known as XELF3N1) shows a portion of the *Xanthium* genomic DNA (from exon 3 to exon 4) encoding ELF3.

SEQ ID NO: 47 (also known as XELF3P1) shows the peptide portion of the *Xanthium* ELF3 protein encoded for by SEQ ID NO: 46.

SEQ ID NO: 48 (also known as XELF3N2) shows a portion of the *Xanthium* genomic DNA (from exon 3 to exon 4) encoding ELF3.

SEQ ID NO: 49 (also known as XELF3P2) shows the peptide portion of the *Xanthium* ELF3 protein encoded for by SEQ ID NO: 48.

SEQ ID NO: 50 (also known as XELF3N4) shows a portion of the *Xanthium* genomic DNA (a portion of exon 4) encoding ELF3.

SEQ ID NO: 51 (also known as XELF3P4) shows the peptide portion of the *Xanthium* ELF3 protein encoded for by SEQ ID NO: 50.

SEQ ID NO: 52 (also known as POPELF3N) shows a portion of the Poplar genomic DNA (a portion of exon 4) encoding ELF3.

SEQ ID NO: 53 (also known as POPELF3P) shows the peptide portion of the Poplar ELF3 protein encoded for by SEQ ID NO: 52.

SEQ ID NO: 54 (also known as MIMELF3N) shows a portion of the *Mimulus* genomic DNA (a portion of exon 4) encoding ELF3.

SEQ ID NO: 55 (also known as MIMELF3P) shows the peptide portion of the *Mimulus* ELF3 protein encoded for by SEQ ID NO: 54.

SEQ ID NO: 56 (also known as ZMELF3N) shows a portion of the *Zea mays* contig of cDNA/genomic DNA (exon 2, exon 3, intronic sequence, and exon 4, including stop codon and 3'UTR) encoding ELF3. This partial sequence was originally reported in Genbank Accession No. AI637184.

SEQ ID NO: 57 (also known as ZMELF3P) shows the peptide portion of the *Zea mays* ELF3 protein encoded for by SEQ ID NO: 56.

SEQ ID NO: 58 (also known as LEELF3-AN) shows a portion of the *Lycopersicon esculentum* cDNA (exon 1, exon 2, exon 3, and exon 4, including stop codon and 3'UTR) encoding ELF3.

SEQ ID NO: 59 (also known as LEELF3-AP) shows the peptide portion of the *Lycopersicon esculentum* ELF3 protein encoded for by SEQ ID NO: 58.

SEQ ID NO: 60 (also known as BRELF3AN) shows a portion of the Broccoli genomic DNA (portion of exon 1, exon 2, exon 3, and portion of exon 4) encoding ELF3.

SEQ ID NO: 61 (also known as BRELF3AP) shows the peptide portion of the Broccoli ELF3 protein encoded for by SEQ ID NO: 60.

SEQ ID NO: 62 (also known as BRELF3BN) shows a portion of the Broccoli genomic DNA (a portion of exon 4) encoding ELF3.

SEQ ID NO: 63 (also known as BRELF3BP) shows the peptide portion of the Broccoli ELF3 protein encoded for by SEQ ID NO: 62.

SEQ ID NOs: 64–68 (also known as C-FWD, D-REV, B-FWD, Pea1b-C-FWD, and C-REV, respectively) show primers used to amplify ELF3 homologous sequences.

DETAILED DESCRIPTION OF THE INVENTION

I. Definitions

Unless otherwise noted, technical terms are used according to conventional usage. Definitions of common terms in molecular biology may be found in Benjamin Lewin, *Genes*

V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

ELF3 gene/ELF3 cDNA: Nucleic acid molecules that encode an ELF3 protein. Nucleic acid molecules that encode the *Arabidopsis* ELF3 protein are provided in SEQ ID NO: 3 (*Arabidopsis* ELF3 gene), SEQ ID NO: 1 (*Arabidopsis* ELF3 cDNA) and SEQ ID NO:4 (*Arabidopsis* ELF3 open reading frame). The invention includes not only the nucleic acid molecules provided in SEQ ID NOS: 1, 3 and 4, but also homologs and orthologs of these sequences, other nucleic acid molecules that encode ELF3 proteins, and probes and primers that are derived from these sequences.

elf3 mutant: The early-flowering (elf3) mutant of *Arabidopsis* is insensitive to photoperiod with regard to floral initiation (Zagotta et al., 1992; Zagotta et al., 1996). In addition to being photoperiod-insensitive, all *Arabidopsis* elf3 mutants display the long-hypocotyl phenotype characteristic of plants defective in light reception or the transduction of light signals (Zagotta et al., 1992; Zagotta et al., 1996). Elf3 mutants are primarily defective in blue light-dependent inhibition of hypocotyl elongation, although elf3 mutants are also partially deficient in red light-dependent inhibition of hypocotyl elongation (Zagotta et al., 1996).

ELF3 protein: A protein having ELF3 protein biological activity and sharing amino acid sequence identity with the amino acid sequence of the prototypical ELF3 protein shown in SEQ ID NO: 2 (the *Arabidopsis* ELF3 protein). ELF3 proteins that are more distantly related to the prototypical ELF3 protein will share at least 60% amino acid sequence identity with the sequence shown in SEQ ID NO: 2, as determined by the methods described below. More closely related ELF3 proteins may share at least 70%, 75% or 80% sequence identity with the *Arabidopsis* ELF3 protein. ELF3 proteins that are most closely related to the *Arabidopsis* protein will have ELF3 protein biological activity and share at least 85%, 90% or 95% sequence identity with the *Arabidopsis* protein.

ELF3 protein biological activity: The ability of a protein to complement an elf3 mutant. The ability of a protein to complement an elf3 mutant may be readily determined by introducing the gene encoding the protein into an elf3 mutant plant using standard methods. If the encoded protein has ELF3 protein biological activity, this will be manifested as a proportion of the transgenic progeny plants having a wild-type phenotype for those characteristics linked to the elf3 mutant (e.g., photoperiod-insensitive flowering and elongated hypocotyl).

ELF3 promoter: The region of nucleic acid sequence upstream (5') of the ELF3 coding sequence that is responsible for spatial and temporal regulation of ELF3 transcription. ELF3 transcription is circadian regulated, but with an RNA maximum that is "later" in the 24-hour period than that of other known circadian genes, e.g., CAB, CCR2, CCA1 and LHY (Wang and Tobin, 1998; Schaffer et al., 1998). ELF3-like circadian rhythm or cyclic transcriptional regulation refers to this type of a relatively delayed transcription maximum. Because ELF3 transcription reaches a maximal level relatively late in the 24-hour period, the ELF3 promoter will allow for altering the setting of the circadian clock. For instance, if another circadian-regulated gene (e.g., chlorophyll a/b binding protein) is expressed from the ELF3 promoter, the circadian set on this protein will be delayed to match that of ELF3. In addition, the ELF3 promoter may be used to provide altered expression of other genes that are under control of the circadian clock, if clock components and/or regulators such as CCA1 and LHY are driven by the ELF3 promoter instead of their own promoters or a constitutive promoter, for instance the 35S promoter.

The ELF3 promoter region is contained within the 4071 kb 5' regulatory region sequence shown in SEQ ID NO: 5, but one of ordinary skill in the art will appreciate that expression may be controlled by using less than this entire 5' upstream region, e.g., nucleotides 500–4071, 1000–4071, 1500–4071, 2000–4071, 2500–4071, 3000–4071, 3500–4071 or 4000–4071. One embodiment of an ELF3 promoter is about nucleotides 1 through about 1900 of the 5' upstream region shown in SEQ ID NO: 5.

Sequences as short as 50 or 100 nucleotides from within the 5' regulatory region may also be employed. The degree to which such a sequence provides for ELF3-like circadian cyclic transcriptional regulation, when included in an expression vector, can be ascertained by the methods described herein. Thus, the term "biologically active ELF3 promoter" refers to a 5' regulatory region of an ELF3 gene, or a part or a variant of such a region, that, when operably linked to the 5' end of an ORF and introduced into a plant, results in ELF3-like (i.e., relatively late) circadian cyclic transcript expression of the protein encoded by the ORF.

Essence of ELF3 Consensus (EEC): One or more highly conserved regions of amino acid sequence within an ELF3 protein or ELF3 protein homolog. EECs are depicted in FIGS. 1 and 2.

Oligonucleotide: A linear polynucleotide sequence of up to about 100 nucleotide bases in length.

Probes and primers: Nucleic acid probes and primers can be readily prepared based on the nucleic acid molecules provided in this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acid molecules, typically DNA oligonucleotides 15 nucleotides or more in length. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al. (1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 20 consecutive nucleotides of the *Arabidopsis* ELF3 cDNA or gene will anneal to a target sequence such as an ELF3 gene homolog from tomato contained within a tomato genomic DNA library with a higher specificity than a corresponding primer of only 15 nucleotides. Thus, in order to obtain greater specificity, probes and primers can be selected that comprise 20, 25, 30, 35, 40, 50 or more consecutive nucleotides of the *Arabidopsis* ELF3 cDNA or gene sequences.

The invention thus includes isolated nucleic acid molecules that comprise specified lengths of the disclosed ELF3 cDNA or gene sequences. Such molecules may comprise at least 20, 25, 30, 35, 40, 50 or 100 consecutive nucleotides of these sequences and may be obtained from any region of the disclosed sequences. By way of example, the *Arabidopsis* ELF3 cDNA, ORF and gene sequences may be apportioned into halves or quarters based on sequence length, and the isolated nucleic acid molecules may be derived from the first or second halves of the molecules, or any of the four quarters. The *Arabidopsis* ELF3 cDNA, shown in SEQ ID NO: 1, can be used to illustrate this. The *Arabidopsis* ELF3 cDNA is 2518 nucleotides in length and so may be hypothetically divided into about halves (nucleotides 1–1259 and 1260–2518) or about quarters (nucleotides 1–629, 630–1259, 1260–1889 and 1890–2518). Nuclei molecules may be selected that comprise at least 20, 25, 30, 35, 40, 50 or 100 consecutive nucleotides of any of these or other portions of the *Arabidopsis* ELF3 cDNA. Thus, representative nucleic acid molecules might comprise at least 25 consecutive nucleotides of the region comprising nucleotides 1–1259 of the disclosed *Arabidopsis* cDNA, or of the regions comprising nucleotides 1–1135 or 2502–2518 of the cDNA.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs of the *Arabidopsis* ELF3 protein will possess a relatively high degree of sequence identity when aligned using standard methods. Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene,* 73: 237–244, 1988; Higgins & Sharp *CABIOS* 5: 151–153, 1989; Corpet et al. *Nuc. Acids Res.* 16, 10881–90, 1988; Huang et al. *Computer Appls. in the Biosciences* 8, 155–65, 1992; and Pearson et al. *Meth. Mol. Bio.* 24, 307–31, 1994. Altschul et al. (*J. Mol. Biol.* 215:403–410, 1990), presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI BLAST web-site. A description of how to determine sequence identity using this program is available at the help page of the NCBI web-site.

Homologs of the disclosed *Arabidopsis* ELF3 protein typically possess at least 60% sequence identity counted over full length alignment with the amino acid sequence of *Arabidopsis* ELF3 using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 91%, at least 92%, at least 93%, at least 94% or at least 95% sequence identity. When less than the entire sequence is being compared for sequence identity, homologs will typically possess at least 75% sequence identity over short windows of 10–20 amino acids, and may possess sequence identities of at least 85% or at least 90% or 95% or more depending on their similarity to the reference sequence. Methods for determining sequence identity over such short windows are described at the NCBI web-site, frequently asked questions page. One of ordinary skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs. ELF3 homologs will typically also have ELF3 protein biological activity.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993). Nucleic acid molecules that hybridize under stringent conditions to the *Arabidopsis* ELF3 sequences will typically hybridize to a probe based on either the entire *Arabidopsis* ELF3 cDNA or selected portions of the cDNA under wash conditions of 0.2×SSC, 0.1% SDS at 55° C. for 1 hour. A more detailed discussion of hybridization conditions, including low stringency conditions, is presented below.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Ortholog: Two nucleotide or amino acid sequences are orthologs of each other if they share a common ancestral sequence and diverged when a species carrying that ancestral sequence split into two species. Orthologous sequences are also homologous sequences.

Specific binding agent: An agent that binds substantially only to a defined target. Thus an ELF3 protein specific binding agent binds substantially only the ELF3 protein. As used herein, the term "ELF3 protein specific binding agent" includes anti-ELF3 protein antibodies and other agents that bind substantially only to the ELF3 protein.

Anti-ELF3 protein antibodies may be produced using standard procedures described in a number of texts, including Harlow and Lane (1988). The determination that a particular agent binds substantially only to the ELF3 protein may readily be made by using or adapting routine procedures. One suitable in vitro assay makes use of the Western blotting procedure (described in many standard texts, including Harlow and Lane (1988)). Western blotting may be used to determine that a given ELF3 protein binding agent, such as an anti-ELF3 protein monoclonal antibody, binds substantially only to the ELF3 protein.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules.

Purified: The term purified does not require absolute purity; rather, it is intended as a relative term. Thus, for example, a purified ELF3 protein preparation is one in which the ELF3 protein is more enriched than the protein is in its natural environment within a cell. Generally, a preparation of ELF3 protein is purified such that ELF3 represents at least 5% of the total protein content of the preparation. For particular applications, higher purity may be desired, such that preparations in which ELF3 represents at least 25%, 50% or at least 90% of the total protein content may be employed.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

cDNA (complementary DNA): A piece of DNA lacking internal, non-coding segments (introns) and regulatory sequences that determine transcription. cDNA is synthesized in the laboratory by reverse transcription from messenger RNA extracted from cells.

ORF (open reading frame): A series of nucleotide triplets (codons) coding for amino acids without any internal termination codons. These sequences are usually translatable into a peptide.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually).

II. ELF3 Protein and Nucleic Acid Sequences

This invention provides ELF3 proteins and ELF3 nucleic acid molecules, including cDNA and gene sequences. The prototypical ELF3 sequences are the *Arabidopsis* sequences, and the invention provides for the use of these sequences to produce transgenic plants, such as corn and rice plants, having increased or decreased levels of ELF3 protein.

a. *Arabidopsis* ELF3

The *Arabidopsis* ELF3 genomic sequence is shown in SEQ ID NO: 3. The sequence comprises three introns and four exons, and encodes a protein that is 696 amino acids in length (SEQ ID NO: 2 shows the amino acid sequence of the ELF3 protein). The *Arabidopsis* ELF3 protein shares no significant homology to any known published proteins with assigned function. However, one published *Arabidopsis* EST (GenBank # N96569; Newman et al., 1994) overlaps nucleotides 853–2088 of the *Arabidopsis* ELF3 open reading frame (ORF) (SEQ ID NO: 4) (nucleotides 1136–2501 of the *Arabidopsis* ELF3 cDNA, SEQ ID NO: 1).

GenBank accession numbers for ELF3 and putative ELF3 homologs identified as such by this research group are as follows: AtELF3 (*A. thaliana* genomic DNA: AC004747, published Dec. 17, 1999), AtEEC (*A. thaliana* genomic DNA: AB023045, published Nov. 20, 1999), cELF3 (yet to be submitted), tELF3 *[Lycopersicon esculentum* Expressed Sequence Tags (ESTs) from Clemson University Genomics Institute: AW093790 (Oct. 18, 1999), AI894513 (Jul. 27, 1999), AI488927 (Jun. 29, 1999), AI486934 (Jun. 29, 1999), AI894398 (Jul. 27, 1999)], rELF3 (*Oryza sativa* genomic DNA: AP000399, published Dec. 3, 1999), and mELF3 (*Zea mays* EST from Stanford University Genome Center: AI637184, published Apr. 26, 1999).

The cDNA corresponding to the ELF3 gene is shown in SEQ ID NO: 1, and the ELF3 ORF is shown in SEQ ID NO: 4. As described below, the *Arabidopsis* ELF3 protein has ELF3 biological activity, i.e., it complements the defective characteristics of photoperiod-insensitive flowering and elongated hypocotyl in elf3 mutant plants when the ELF3 gene sequence is introduced into these plants and the ELF3 protein is thereby expressed. In addition, ELF3 proteins contain one or more ESSENCE of ELF3 CONSENSUS (EEC) regions (see FIG. 2).

With the provision herein of the *Arabidopsis* ELF3 cDNA and gene sequences, the polymerase chain reaction (PCR) may now be utilized as a preferred method for producing nucleic acid sequences encoding the *Arabidopsis* ELF3 protein. For example, PCR amplification of the *Arabidopsis* ELF3 cDNA sequence may be accomplished either by direct PCR from a plant cDNA library or by reverse-transcription PCR (RT-PCR) using RNA extracted from plant cells as a template. Methods and conditions for both direct PCR and RT-PCR are known in the art and are described in Innis et al. (1990). Any plant cDNA library would be useful for direct PCR. The ELF3 gene sequences can be isolated from other libraries, for instance the IGF *Arabidopsis* BAC library (Mozo et al. 1998).

The selection of PCR primers will be made according to the portions of the ELF3 cDNA (or gene) that are to be amplified. Primers may be chosen to amplify small segments of the cDNA, the open reading frame, the entire cDNA molecule or the entire gene sequence. Variations in amplification conditions may be required to accommodate primers of differing lengths; such considerations are well known in the art and are discussed in Innis et al. (1990), Sambrook et al. (1989), and Ausubel et al. (1992). By way of example only, the *Arabidopsis* ELF3 cDNA molecule as shown in SEQ ID NO: 1 (excluding the poly A tail) may be amplified using the following combination of primers:

```
primer 1:
5' TGAAAACTCACTTTGGTTTTGTTTG 3'    (SEQ ID NO: 6)
primer 2:
5' AAGACAAATTAACACATATAAATGA 3'    (SEQ ID NO: 7)
```

The open reading frame portion of the cDNA (SEQ ID NO: 4) may be amplified using the following primer pair:

```
primer 3:
5' ATGAATAGAGGGAAAGATGAGGAG 3'     (SEQ ID NO: 8)
primer 4:
5' TTAAGGCTTAGAGGAGTCATAGCGT 3'    (SEQ ID NO: 9)
```

These primers are illustrative only; one of ordinary skill in the art will appreciate that many different primers may be derived from the provided cDNA and gene sequences in order to amplify particular regions of these molecules. Resequencing of PCR products obtained by these amplification procedures is recommended; this will facilitate confirmation of the amplified sequence and will also provide information on natural variation in this sequence in different ecotypes and plant populations. Oligonucleotides derived from the *Arabidopsis* ELF3 sequence may be used in such sequencing methods.

Oligonucleotides that are derived from the *Arabidopsis* ELF3 cDNA or gene sequences are encompassed within the scope of the present invention. Preferably, such oligonucleotide primers will comprise a sequence of at least 15–20 consecutive nucleotides of the *Arabidopsis* ELF3 cDNA or gene sequences. To enhance amplification specificity, oligonucleotide primers comprising at least 25, 30, 35, 40, 45 or 50 consecutive nucleotides of these sequences may also be used.

b. ELF3 Genes in Other Plant Species

Orthologs of the ELF3 gene are present in a number of plant species including *Chlamydomonas*, Douglas fir, corn, broccoli, cauliflower, soybean, *Medicago*, rice, poplar, tobacco, *Cardamine*, and tomato (see Examples 4, 5 and 6, below). With the provision herein of the prototypical ELF3 protein from *Arabidopsis* and cDNA and gene sequences that encode this protein, cloning of cDNAs and genes that encode ELF3 protein orthologs in other plant species is now enabled. Standard methods, including those described herein, can be used. As described above, orthologs of the disclosed *Arabidopsis* ELF3 protein have ELF3 protein biological activity and typically possess at least 60% sequence identity counted over the full length alignment with the amino acid sequence of *Arabidopsis* ELF3 using the NCBI Blast 2.0, gapped blastp set to default parameters. Proteins with even greater similarity to the *Arabidopsis* sequence will show greater percentage identities when assessed by this method, such as at least 70%, at least 75%, at least 80%, at least 90%, at least 91%, at least 92%, at least 93%, at least 94% or at least 95% or more sequence identity.

Both conventional hybridization and PCR amplification procedures may be utilized to clone sequences encoding ELF3 protein orthologs. Common to these techniques is the hybridization of probes or primers derived from the *Arabidopsis* ELF3 cDNA or gene sequence to a target nucleotide preparation. This target may be, in the case of conventional hybridization approaches, a cDNA or genomic library or, in the case of PCR amplification, a cDNA or genomic library, or an mRNA preparation.

Direct PCR amplification may be performed on cDNA or genomic libraries prepared from the plant species in question, or RT-PCR may be performed using mRNA extracted from the plant cells using standard methods. PCR primers will comprise at least 15 consecutive nucleotides of the *Arabidopsis* ELF3 cDNA or gene. One of ordinary skill in the art will appreciate that sequence differences between the *Arabidopsis* ELF3 cDNA or gene and the target nucleic acid to be amplified may result in lower amplification efficiencies. To compensate for this difference, longer PCR primers or lower annealing temperatures may be used during the amplification cycle. Where lower annealing temperatures are used, sequential rounds of amplification using nested primer pairs may be necessary to enhance amplification specificity.

For conventional hybridization techniques, the hybridization probe is preferably conjugated with a detectable label such as a radioactive label, and the probe is preferably of at least 20 nucleotides in length. As is well known in the art, increasing the length of hybridization probes tends to give enhanced specificity. The labeled probe derived from the *Arabidopsis* cDNA or gene sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

Orthologs of the *Arabidopsis* ELF3 may alternatively be obtained by immunoscreening an expression library. With the provision herein of the disclosed *Arabidopsis* ELF3 nucleic acid sequences, the protein may be expressed in and purified from a heterologous expression system (e.g., *E. coli*) and used to raise antibodies (monoclonal or polyclonal) specific for the *Arabidopsis* ELF3 protein. Antibodies may also be raised against synthetic peptides derived from the *Arabidopsis* ELF3 amino acid sequence presented herein. Methods of raising antibodies are well known in the art and are described in Harlow and Lane (1988). Such antibodies can be used to screen an expression cDNA library produced from the plant from which it is desired to clone the ELF3 ortholog, using routine methods. The selected cDNAs can be confirmed by sequencing.

c. ELF3 Sequence Variants

With the provision of the *Arabidopsis* ELF3 protein and ELF3 cDNA and gene sequences herein, the creation of variants of these sequences is now enabled.

Variant ELF3 proteins include proteins that differ in amino acid sequence from the *Arabidopsis* ELF3 sequence disclosed but which retain ELF3 protein biological activity. Such proteins may be produced by manipulating the nucleotide sequence of the *Arabidopsis* ELF3 cDNA or gene using standard procedures, including for instance site-directed mutagenesis or PCR. The simplest modifications involve the substitution of one or more amino acids for amino acids having similar biochemical properties. These so-called conservative substitutions are likely to have minimal impact on the activity of the resultant protein. Table 1 shows amino acids that may be substituted for an original amino acid in a protein, and which are regarded as conservative substitutions.

TABLE 1

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in protein functions or other features may be obtained by selecting amino acid substitutions that are less conservative than those listed in Table 1. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine). The effects of these amino acid substitutions, deletions, or additions may be assessed in ELF3 protein derivatives by analyzing the ability of a gene encoding the derivative protein to complement the photoperiod-insensitive flowering and elongated hypocotyl defects in an elf3 mutant. Alternatively, the effect may be examined by studying circadian influenced CAB-luc transcription and/or leaf movement as discussed in Example 2, below.

Variant ELF3 cDNA or genes may be produced by standard DNA mutagenesis techniques, for example, M13 primer mutagenesis. Details of these techniques are provided in Sambrook et al. (1989), Ch. 15. By the use of such techniques, variants may be created which differ in minor ways from the *Arabidopsis* ELF3 cDNA or gene sequences disclosed, yet which still encode a protein having ELF3 protein biological activity. DNA molecules and nucleotide sequences that are derivatives of those specifically disclosed herein and that differ from those disclosed by the deletion, addition, or substitution of nucleotides while still encoding a protein that has ELF3 protein biological activity are comprehended by this invention. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed *Arabidopsis* ELF3 protein sequence. For example, the 23rd amino acid residue of the *Arabidopsis* ELF3 protein is alanine. This alanine residue is encoded for by the nucleotide codon triplet GCA. Because of the degeneracy of the genetic code, three other nucleotide codon triplets—GCT, GCC and GCG—also code for alanine. Thus, the nucleotide sequence of the *Arabidopsis* ELF3 ORF could be changed at this position to any of these three alternative codons without affecting the amino acid composition or other characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences that encode an ELF3 protein, but which vary from the disclosed nucleic acid sequences by virtue of the degeneracy of the genetic code.

Variants of the ELF3 protein may also be defined in terms of their sequence identity with the prototype ELF3 protein shown in SEQ ID NO: 2. As described above, ELF3 proteins have ELF3 biological activity and share at least 60% sequence identity with the *Arabidopsis* ELF3 protein. Nucleic acid sequences that encode such proteins may readily be determined simply by applying the genetic code to the amino acid sequence of an ELF3 protein, and such nucleic acid molecules may readily be produced by assembling oligonucleotides corresponding to portions of the sequence.

Nucleic acid molecules that are derived from the *Arabidopsis* ELF3 cDNA and gene sequences disclosed include molecules that hybridize under stringent conditions to the disclosed prototypical ELF3 nucleic acid molecules, or fragments thereof. Stringent conditions are hybridization at 55° C. in 6×SSC, 5× Denhardt's solution, 0.1% SDS and 100 µg sheared salmon testes DNA, followed by 15–30 minute sequential washes at 55° C. in 2×SSC, 0.1% SDS, followed by 1×SSC, 0.1% SDS and finally 0.2×SSC, 0.1% SDS.

Low stringency hybridization conditions (to detect less closely related homologs) are performed as described above but at 50° C. (both hybridization and wash conditions); however, depending on the strength of the detected signal, the wash steps may be terminated after the first 2×SSC, 0.1% SDS wash.

The *Arabidopsis* ELF3 gene or cDNA, and orthologs of these sequences from other plants, may be incorporated into transformation vectors and introduced into plants to produce plants with an altered photoperiodic or circadian rhythm phenotype, as described below.

III. Introducing ELF3 into Plants

Once a nucleic acid molecule (e.g., cDNA or gene) encoding a protein involved in the determination of a particular plant characteristic has been isolated, standard techniques may be used to express the cDNA in transgenic plants in order to modify that particular plant characteristic. The basic approach is to clone, for instance, the cDNA into a transformation vector, such that it is operably linked to control sequences (e.g., a promoter) that direct expression of the cDNA in plant cells. The transformation vector is then introduced into plant cells by one of a number of techniques (e.g., electroporation) and progeny plants containing the introduced cDNA are selected. Preferably all or part of the transformation vector will stably integrate into the genome of the plant cell. That part of the transformation vector that integrates into the plant cell and that contains the introduced cDNA and associated sequences for controlling expression (the introduced "tansgene") may be referred to as the recombinant expression cassette.

Selection of progeny plants containing the introduced transgene may be based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

Successful examples of the modification of plant characteristics by transformation with cloned cDNA sequences are replete in the technical and scientific literature. Selected examples, which serve to illustrate the knowledge in this field of technology, include:

U.S. Pat. No. 5,451,514 (modification of lignin synthesis using antisense RNA and co-suppression);

U.S. Pat. No. 5,750,385 (modification of plant light-, seed- and fruit-specific gene expression using sense and antisense transformation constructs);

U.S. Pat. No. 5,583,021 (modification of virus resistance by expression of plus-sense untranslatable RNA);

U.S. Pat. No. 5,589,615 (production of transgenic plants with increased nutritional value via the expression of modified 2S storage albumins);

U.S. Pat. No. 5,268,526 (modification of phytochrome expression in transgenic plants);

U.S. Pat. No. 5,741,684 (production of plants resistant to herbicides or antibiotics through the use of anti-sense expression);

U.S. Pat. No. 5,773,692 (modification of the levels of chlorophyll by transformation of plants with anti-sense messages corresponding to chlorophyll a/b binding protein);

WO 96/13582 (modification of seed VLCFA composition using over expression, co-suppression and antisense RNA in conjunction with the *Arabidopsis* FAE1 gene)

These examples include descriptions of transformation vector selection, transformation techniques and the assembly of constructs designed to over-express the introduced nucleic acid, as well as techniques for sense suppression and anti-sense expression. In light of the foregoing and the provision herein of the *Arabidopsis* ELF3 cDNA and gene sequences, one of ordinary skill in the art will be able to introduce these nucleic acid molecules, or orthologous, homologous or derivative forms of these molecules, into plants in order to produce plants having altered ELF3 activity. Manipulating the expression of ELF3 in plants will be useful to confer altered circadian clock and/or photoperiodism function. Alteration of the ELF3 protein levels in plants could be used to re-set or customize the circadian clock, for instance in order to alter the plant developmental patterns or photoperiodic responses (e.g., the timing of floral development).

a. Plant Types

The presence of a circadian cycle appears to be universal, occurring not only in all plants thus far examined, but also in insects, including *Drosophila* (Hall, 1990) and microbes such as *Neurospora crassa* (Dunlap, 1993). At the molecular level, ELF3 homologs have been found in a variety of plant species (see Example 4, below). Thus, expression of the ELF3 protein may be modified in a wide range of higher plants to confer altered circadian clock and/or photoperiodism function, including monocotyledonous and dicotyledenous plants. These include, but are not limited to, *Arabidopsis, Cardamine*, cotton, tobacco, maize, wheat, rice, barley, soybean, beans in general, rape/canola, alfalfa, flax, sunflower, safflower, *brassica*, cotton, flax, peanut, clover; vegetables such as lettuce, tomato, cucurbits, cassava, potato, carrot, radish, pea, lentils, cabbage, cauliflower, broccoli, Brussels sprouts, peppers; tree fruits such as citrus, apples, pears, peaches, apricots, walnuts; other trees including poplar, oak, maple, pine, spruce and other conifers; and flowers or other ornamental plants such as carnations, roses, petunias, orchids, impatiens, pansies, lilies, snapdragons, geraniums, and so forth.

b. Vector Construction, Choice of Promoters

A number of recombinant vectors suitable for stable transformation of plant cells or for the establishment of transgenic plants have been described including those described in Pouwels et al., (1987), Weissbach and Weissbach, (1989), and Gelvin et al., (1990). Typically, plant transformation vectors include one or more cloned plant genes (or cDNAs) under the transcriptional control of 5' and 3' regulatory sequences, and at least one dominant selectable marker. Such plant transformation vectors typically also contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters that may be useful for expressing an ELF3 nucleic acid molecule include: the cauliflower mosaic virus (CaMV) 35S promoter, which confers constitutive, high-level expression in most plant tissues (see, e.g., Odel et al., 1985, Dekeyser et al., 1990, Terada and Shimamoto, 1990; Benfey and Chua. 1990); the nopaline synthase promoter (An et al., 1988); and the octopine synthase promoter (Fromm et al., 1989).

A variety of plant gene promoters are regulated in response to environmental, hormonal, chemical, and/or developmental signals, and can be used for expression of the cDNA in plant cells. Such promoters include, for instance, those regulated by: (a) heat (Callis et al., 1988; Ainley, et al. 1993; Gilmartin et al. 1992); (b) light (e.g., the pea rbcS-3A promoter, Kuhlemeier et al., 1989, and the maize rbcS promoter, Schaffner and Sheen, 1991); (c) hormones, such as abscisic acid (Marcotte et al., 1989); (d) wounding (e.g., wunI, Siebertz et al., 1989); and (e) chemicals such as methyl jasminate or salicylic acid (see also Gatz et al., 1997).

Alternatively, tissue specific (root, leaf, flower, or seed, for example) promoters (Carpenter et al 1992, Denis et al 1993, Opperman et al 1993, Stockhause et al 1997; Roshal et al, 1987; Schernthaner et al, 1988; and Bustos et al., 1989) can be fused to the coding sequence to obtained protein expression in specific organs.

Promoters responsive to the circadian cycle can also be used in plant gene expression vectors. Such promoters include the native ELF3 promoter as described herein, and the promoter from the chlorophyll a/b binding protein (Millar et al. 1992).

Plant transformation vectors may also include RNA processing signals, for example, introns, which may be positioned upstream or downstream of the ORF sequence in the transgene. In addition, the expression vectors may include further regulatory sequences from the 3'-untranslated region of plant genes, e.g., a 3' terminator region to increase mRNA stability of the mRNA, such as the PI-II terminator region of potato or the *Agrobacterium* octopine or nopaline synthase 3' terminator regions. The 3' region of the ELF3 gene can also be used.

Finally, as noted above, plant transformation vectors may include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

c. Arrangement of ELF3 Sequence in the Vector

The particular arrangement of the ELF3 sequence in the transformation vector will be selected according to the type of expression of the sequence that is desired.

Where enhanced ELF3 protein activity is desired in the plant, an ELF3 ORF may be operably linked to a constitutive high-level promoter such as the CaMV 35S promoter. As noted below, modification of ELF3 synthesis may also be achieved by introducing into a plant a transformation vector containing a variant form of an ELF3 cDNA or gene.

In contrast, a reduction of ELF3 activity in the transgenic plant may be obtained by introducing into plants an antisense construct based on an ELF3 cDNA or gene sequence. For antisense suppression, an ELF3 cDNA or gene is arranged in reverse orientation relative to the promoter sequence in the transformation vector. The introduced sequence need not be a full length ELF3 cDNA or gene, and need not be exactly homologous to the native ELF3 cDNA or gene found in the plant type to be transformed. Generally, however, where the introduced sequence is of shorter length, a higher degree of homology to the native ELF3 sequence will be needed for effective antisense suppression. The introduced antisense sequence in the vector generally will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous ELF3 gene in the plant cell. Although the exact mechanism by which antisense RNA molecules interfere with gene expression has not been elucidated, it is believed that antisense RNA molecules bind to the endogenous mRNA molecules and thereby inhibit translation of the endogenous mRNA. The production and use of antisense constructs are disclosed, for instance, in U.S. Pat. No. 5,773,692 (using constructs encoding anti-sense RNA for chlorophyll ab binding protein to reduce plant chlorophyll content), and U.S. Pat. No. 5,741,684 (regulating the fertility of pollen in various plants through the use of anti-sense RNA to genes involved in pollen development or function).

Suppression of endogenous ELF3 gene expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. Inclusion of ribozyme sequences within antisense RNAs may be used to confer RNA cleaving activity on the antisense RNA, such that endogenous mRNA molecules that bind to the antisense RNA are cleaved, leading to an enhanced antisense inhibition of endogenous gene expression.

Constructs in which an ELF3 cDNA or gene (or variants thereof) are over-expressed may also be used to obtain co-suppression of the endogenous ELF3 gene in the manner described in U.S. Pat. No. 5,231,021 to Jorgensen. Such co-suppression (also termed sense suppression) does not require that the entire ELF3 cDNA or gene be introduced into the plant cells, nor does it require that the introduced sequence be exactly identical to the endogenous ELF3 gene. However, as with antisense suppression, the suppressive efficiency will be enhanced as (1) the introduced sequence is lengthened and (2) the sequence similarity between the introduced sequence and the endogenous ELF3 gene is increased.

Constructs expressing an untranslatable form of an ELF3 mRNA may also be used to suppress the expression of endogenous ELF3 activity. Methods for producing such constructs are described in U.S. Pat. No. 5,583,021 to Dougherty et al. Preferably, such constructs are made by introducing a premature stop codon into an ELF3 ORF.

Finally, dominant negative mutant forms of the disclosed sequences may be used to block endogenous ELF3 activity. Such mutants require the production of mutated forms of the ELF3 protein that interact with the same molecules as ELF3 but do not have ELF3 activity.

d. Transformation and Regeneration Techniques

Transformation and regeneration of both monocotyledonous and dicotyledonous plant cells is now routine, and the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* (AT) mediated transformation. Typical procedures for transforming and regenerating plants are described in the patent documents listed at the beginning of this section.

e. Selection of Transformed Plants

Following transformation and regeneration of plants with the transformation vector, transformed plants are usually selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed using the methods described herein to determine whether the circadian cycle or photoperiodism of the transformed plant has been altered as a result of the introduced transgene.

IV. Production of Recombinant ELF3 Protein in Heterologous Expression Systems

Many different expression systems are available for expressing cloned nucleic acid molecules. Examples of prokaryotic and eukaryotic expression systems that are routinely used in laboratories are described in Chapters 16–17 of Sambrook et al. (1989). Such systems may be used to express ELF3 at high levels to facilitate purification of the protein. The purified ELF3 protein may be used for a variety of purposes. For example, the purified recombinant enzyme may be used as an immunogen to raise anti-ELF3 antibodies. Such antibodies are useful as both research reagents (such as in the study of circadian clock and photoperiodism mechanisms in plants) as well as diagnostically to determine expression levels of the protein in plants that are being developed for agricultural or other use. Thus, the antibodies may be used to quantify the level of ELF3 protein both in non-transgenic plant varieties and in transgenic varieties that are designed to over-express or under-express the ELF3 protein. Such quantification may be performed using standard immunoassay techniques, such as ELISA and in situ immunofluorescence and others described in Harlow & Lane (1988).

By way of example only, high level expression of the ELF3 protein may be achieved by cloning and expressing the ELF3 cDNA in yeast cells using the pYES2 yeast expression vector (INVITROGEN, Carlsbad, Calif.). Alternatively, a genetic construct may be produced to direct secretion of the recombinant ELF3 protein from yeast cells into the growth medium. This approach will facilitate the purification of the ELF3 protein, if this is necessary. Secretion of the recombinant protein from the yeast cells may be achieved by placing a yeast signal sequence adjacent to the ELF3 coding region. A number of yeast signal sequences have been characterized, including the signal sequence for yeast invertase. This sequence has been successfully used to direct the secretion of heterologous proteins from yeast cells, including such proteins as human interferon (Chang et al., 1986), human lactoferrin (Liang and Richardson, 1993) and prochymosin (Smith et al., 1985).

Alternatively, the enzyme may be expressed at high level in prokaryotic expression systems, such as *E. coli*, as described in Sambrook et al. (1989). Commercially available prokaryotic expression systems include the pBAD expression system and the ThioFusion expression system (INVITROGEN, Carlsbad, Calif.).

V. ELF3 Promoter

The 5' regulatory region of the ELF3 gene is also provided herein (SEQ ID NO: 5). This regulatory region confers ELF3-like circadian rhythm-based expression on open reading frames to which it is operably linked. Approximately 4 kb of the ELF3 5' regulatory region is provided in SEQ ID NO: 5. While this entire ca. 4 kb regulatory sequence may be employed, one of ordinary skill in the art will appreciate that less than this entire sequence may be sufficient to confer ELF3-like circadian rhythm expression. For example, sequences comprising nucleotides 1–4071 of SEQ ID NO: 5 or shorter sequences such as those spanning nucleotides 500–4071, 1000–4071, 1500–4071, 2000–4071, 2500–4071, 3000–4071, 3500–4071 and 4000–4071 may be employed. One embodiment of an ELF3 promoter is about nucleotides 1 through about 1900 of the 5' upstream region shown in SEQ ID NO: 5. Other particular embodiments include about nucleotides 50–1900, 150–1900, 250–1900, 350–1900, 450–1900, 550–1900 and so forth.

Sequences as short as 50 or 100 nucleotides from within the 5' regulatory region of ELF3 may also be employed. The determination of whether a particular sub-region of the disclosed sequence operates to confer effective ELF3-like circadian rhythm expression in a particular system (taking into account the plant species into which the construct is being introduced, the level of expression required, etc.) will be performed using known methods. These include, for instance, operably linking the promoter sub-region to a marker gene (e.g. GUS or luciferase), introducing such constructs into plants, and determining the level of expression of the marker gene.

The present invention therefore facilitates the production, by standard molecular biology techniques, of nucleic acid molecules comprising this promoter sequence operably linked to a nucleic acid sequence, such as an open reading frame. Suitable open reading frames include open reading frames encoding any protein for which ELF3-like circadian rhythm expression is desired.

EXAMPLES

Example 1

Cloning *Arabidopsis* ELF3

The ELF3 gene was isolated by map-based positional cloning. Molecular markers tightly linked to the ELF3 gene were identified by random fragment length polymorphism (RFLP) analysis, and a high resolution genetic map of the locus was constructed. The region containing the ELF3 gene was narrowed down to 30 kb contained on a single bacterial artificial chromosome (BAC). This BAC was sequenced, and cDNAs with homology to sequences within the BAC were isolated from a variety of cDNA libraries. The ELF3 sequence was further localized by complementation experiments to a 10 kb subcloned fragment contained within the BAC. Identification of the appropriate gene within the subcloned fragment was confirmed through isolation and sequencing of elf3 alleles from various *Arabidopsis* elf3 mutants.

The isolated ELF3 gene (SEQ ID NO: 3) has no significant sequence similarity to other DNA or protein sequences with assigned function. However, a published EST (GenBank # N96569; Newman et al., 1994) overlaps nucleotide 1235–2501 of the corresponding cDNA (SEQ ID NO: 1). ELF3 has four exons, and is transcribed as an mRNA of about 2.4 kb in *Arabidopsis* seedlings and in mature leaves. The putative protein (SEQ ID NO: 2) encoded by the ELF3 ORF (SEQ ID NO: 4) is 695 amino acids in length and has a predicted molecular weight of approximately 80 KDa.

Research by this group has recently identified several putative ELF3 orthologs from other plant species, including *Cardamine oligosperma*, tomato, rice, and maize (see Examples 4 and 5, below). GenBank accession numbers for ELF3 and putative ELF3 homologs identified as such by this research group are as follows: AtELF3 (*A. thaliana* genomic DNA: AC004747, published Dec. 17, 1999), AtEEC (*A. thaliana* genomic DNA: AB023045, published Nov. 20, 1999), cELF3 (yet to be submitted), tELF3 *[Lycopersicon esculentum* Expressed Sequence Tags (ESTs) from Clemson University Genomics Institute: AW093790 (Oct. 18, 1999), AI894513 (Jul. 27, 1999), AI488927 (Jun. 29, 1999), AI486934 (Jun. 29, 1999), AI894398 (Jul. 27, 1999)], rELF3 (*Oryza sativa* genomic DNA: AP000399, published Dec. 3, 1999), and mELF3 (*Zea mays* EST from Stanford University Genome Center: AI637184, published Apr. 26, 1999).

Example 2

Analysis of ELF3 Phenotype

Sensitive assays for monitoring circadian rhythm responses in *Arabidopsis* have been developed (Millar and Kay, 1991; Millar et al., 1992). One assay system is based on the observation that the transcription of the chlorophyll a/b binding protein gene, CAB2, cycles on a 24-hour period. Transcription from the CAB2 promoter increases prior to subjective dawn, peaks in late morning, and falls to a low level late in the day (Millar and Kay, 1991). Cycling of CAB mRNA continues under constant light conditions. In order to follow expression in vivo, the CAB2 promoter has been fused to the gene encoding firefly luciferase (luc), and this fusion has been transformed in wild-type *Arabidopsis* (Millar et al., 1992). Transcriptional expression from the CAB2-luc fusion construct is monitored by imaging single transgenic seedlings using a low-light video camera and a photon-counting image processor; the results from imaging the CAB2-luc fusion is comparable to the transcriptional expression of the endogenous CAB2 gene. With this system, over one hundred individual seedlings can be imaged every 30 minutes, thus allowing the collection of thousands of data points in less than one week. This very powerful system has recently been used to characterize several known photomorphogenic *Arabidopsis* mutants (Millar et al., 1995a) and to isolate a short-period mutant of *Arabidopsis* (Millar et al., 1995b). Elf3 mutants examined using this system are defective in circadian regulated CAB2 transcription (Hicks et al., 1996).

An automatic video imaging system can also be used to monitor a second circadian regulated process, leaf movement (Millar and Kay, 1991). Plant leaves turn down (open) during the day and turn up (closed) during the night in a circadian fashion. *Arabidopsis* seedlings display this circadian leaf movement in constant light, and this can be assayed and quantified using a relatively inexpensive video and computer system (Millar and Kay, 1991). The analysis of leaf movements provides an independent circadian regulated process with which to evaluate potential circadian rhythm mutants (see, for instance, Schaffer et al. 1998, using leaf movement to analyze circadian cycle disruption in late elongated hypocotyl (lhy) mutants in *Arabidopsis*). Elf3 mutants are also defective in circadian regulated leaf movements.

These assays may be used to assess the effect that modifying ELF3 protein expression level (e.g., through introduction of ELF3 antisense or sense constructs into plants) has on plant phenotype.

Example 3

Introducing ELF3 Sequences into Plants

Plasmid Construction

*Arabidopsis* ELF3 cDNA (SEQ ID NO: 1) and full-length genomic (SEQ ID NO: 3) sequences were used in the construction of over-expression and antisense vectors. These sequences were operably linked to the CaMV 35S (constitutive) promoter, in both the sense and antisense orientations, and cloned using standard molecular biology techniques into pSJL4 (Jones et al. 1992).

The over-expression and antisense expression cassettes were removed from the above vectors and inserted into pMON505 for *Agrobacterium*-mediated plant transformation.

Plant Transformation

Wild-type and elf3 mutant *Arabidopsis* plants (ecotype Columbia) were transformed using standard in planta *Agrobacterium*-mediated techniques (Chang et al. 1994, Katavic et al. 1994). Transformed seeds were selected on kanamycin, and Kan$^R$ seedlings transferred to soil and grown for further analysis.

Over-expression of ELF3 protein in elf3 mutant plants comprising the ELF3 genomic gene sequence as the transgene resulted in full complementation of the elf3 mutant phenotype in some transformed plants. In some instances, over-expression of ELF3 protein from cDNA-based transgenes in wild-type plants produced elf3 mutant-like plants or plants having intermediate phenotype; this is probably the result of co-suppression. Antisense expression of the full-length ELF3 cDNA in wild-type plants produced some transformants with an elf3 mutant-like phenotype.

Example 4

ELF3 Orthologs

As noted above, orthologs of ELF3 exist in a number of plant species including corn, tomato and tobacco. The existence of these sequences may be demonstrated by hybridization techniques, such as Southern blotting. Hybridization was performed using a probe based on the entire ELF3 cDNA sequence (SEQ ID NO: 1). This probe was hybridized to genomic DNA from *Arabidopsis, Chlamydomonas*, Douglas fir, corn, rice, poplar, tobacco, and tomato. High stringency hybridization was performed at 55° C. in 6×SSC, 5× Denhardt's solution, 0.1% SDS and 100 µg sheared salmon testes DNA, followed by 15–30 minute sequential washes at 55° C. in 2×SSC, 0.1% SDS, followed by 1×SSC, 0.1% SDS and finally 0.2×SSC, 0.1% SDS. A single, clean hybridizing band was observed on the Southern blot in *Arabidopsis*, rice, and tobacco genomic DNA preparations.

Lower stringency hybridization conditions were used to detect less closely related ELF3 homologs. Such hybridization was performed at 50° C. for 24 hours in the hybridization solution described above, followed by washing in 2×SSC, 0.1% SDS at 50° C. for 3 hours, with five sequential changes of wash solution. Hybridization of full length cDNA probe under low stringency hybridization conditions detected ELF3 homologs (indicated by one or more bands on the Southern) in *Arabidopsis, Chlamydomonas*, Douglas fir, corn, rice, poplar, tobacco, and tomato and other plant species.

Once an ELF3-hybridizing band is detected in a plant species, standard techniques such as screening cDNA or genomic libraries from the plant with the ELF3 probe may be used. Alternatively, ELF3 homologs may be isolated by screening an expression library from the plant in question using a ELF3 protein specific binding agent, such as an anti-ELF3 antibody produced as described above. Such homologs may be introduced into plants using the methods described above in order to produce altered circadian rhythm and/or photoperiodic phenotypes.

It is also possible to use primers complementary to the *Arabidopsis* ELF3 sequence to amplify orthologous nucleic acid sequences. For example, an ELF3 ortholog has been isolated in this manner from a *Cardamine* genomic DNA preparation, using the following PCR amplification primers:

```
primer 5:
5' ATGAAGAGAGGGAAAGATGAGG 3'      (SEQ ID NO: 10)

primer 6:
5' GCCACCATCTCGGTATAACC 3'.       (SEQ ID NO: 11)
```

Degenerate mixtures of oligonucleotides may also be used to amplify orthologous nucleic acid sequences. The construction of degenerate oligonucleotides is well known to one of ordinary skill in the art.

Nucleotide sequences from *C. oligosperma* (a member of the family Brassicaceae) were obtained by sequencing polymerase chain reaction products using degenerate oligonucleotides to the *Arabidopsis* ELF3 gene and genomic DNA or cDNA prepared from *C. oligosperma* seedlings using standard techniques. The sequence of the amplified *Cardamine* ELF3 ortholog (cELF3) is shown in SEQ ID NO: 12.

Example 5

Consensus Sequences Within the ELF3 Protein and Homologs Thereof

Computerized, searchable databases were searched for sequences having significant homology the *Arabidopsis* ELF3 cDNA and genomic nucleotide sequences depicted herein, and the *Cardamine* ELF3 ortholog nucleotide sequence (SEQ ID NO: 12).

This search yielded several putative ELF3 homologs. GenBank accession numbers for ELF3 and the putative ELF3 homologs identified as such by this research group are as follows: AtELF3 (*A. thaliana* genomic DNA: AC004747), AtEEC (*A. thaliana* genomic DNA: AB023045), cELF3 (yet to be submitted), tELF3 (*Lycopersicon esculentum* Expressed Sequence Tags (ESTs) from Clemson University Genomics Institute: AW093790, AI894513, AI488927, AI486934, AI894398), rELF3 (*Oryza sativa* genomic DNA: AP000399), and mELF3 (*Zea mays* EST from Stanford University Genome Center: AI637184).

Multiple sequence alignment of the ELF3 proteins (FIGS. 1 and 2) shows four highly conserved regions within ELF3 and putative ELF3 homologs from *Arabidopsis thaliana* (Essence of ELF3 Consensus, EEC) and other plant species (*Cardamine oligosperma*, tomato, rice, and maize) (FIG. 2). Sequences were aligned and analyzed using CLUSTAL W (Thompson et al., *Nucleic Acids Res.* 22, 4673–80, 1994) and PrettyBox (Genetics Computer Group, Inc.). Protein designations are given on the left. Amino acid residues are numbered on both the left and right. Residues shaded in black indicate identity of at least three ELF3/ELF3-related sequences in the alignment; light-shaded residues indicate similarity to consensus.

Example 6

Additional ELF3 Orthologs

The ELF3 sequences and consensus sequences isolated as described above were used additional similar sequences from other plant species, using nucleic acid amplification and/or computer database searches. Additional ELF3 orthologs have been identified in *Medicago trunculata* (SEQ ID NOs: 36–39), *Pisum sativa* (SEQ ID NOs: 40–43), *Glycine max* (SEQ ID NOs: 44- and 45), *Xanthium* (SEQ ID NOs: 46–51), Poplar (SEQ ID NOs: 52–53), *Mimulus* (SEQ ID NOs: 54 and 55), *Zea mays* (SEQ ID NOs: 56 and 57), *Lycopersicon esculentum* (SEQ ID NOs: 58 and 59), and Broccoli (SEQ ID NOs: 60–63). Nucleic acid amplification, particularly polymerase chain amplification (PCR) also was used to confirm several of these sequences. For isolation and/or confirmation, amplification reactions were annealed at 55° C. and extended for 35 seconds per round. The primers used were as follows:

| Amplified ortholog | Forward primer | Reverse primer |
| --- | --- | --- |
| Pisum sativa (SEQ ID NO: 40) | B-FWD, SEQ ID NO: 66 | C-REV, SEQ ID NO: 68 |
| Pisum sativa (SEQ ID NO: 42) first round | Pealb-C-FWD, SEQ ID NO: 67 | D-REV, SEQ ID NO: 65 |
| Pisum sativa (SEQ ID NO: 42) second round | C-FWD, SEQ ID NO: 64 | D-REV, SEQ ID NO: 65 |
| Xanthium (SEQ ID NO: 46) | B-FWD, SEQ ID NO: 66 | C-REV, SEQ ID NO: 68 |
| Xanthium (SEQ ID NO: 48) | B-FWD, SEQ ID NO: 66 | C-REV, SEQ ID NO: 68 |
| Xanthium (SEQ ID NO: 50) | C-FWD, SEQ ID NO: 64 | D-REV, SEQ ID NO: 65 |
| Poplar (SEQ ID NO: 52) | C-FWD, SEQ ID NO: 64 | D-REV, SEQ ID NO: 65 |
| Mimulus (SEQ ID NO: 54) | C-FWD, SEQ ID NO: 64 | D-REV, SEQ ID NO: 65 |
| Zea mays (SEQ ID NO: 56) | B-FWD, SEQ ID NO: 66 | C-REV, SEQ ID NO: 68 |
| Zea mays (SEQ ID NO: 56) | C-FWD, SEQ ID NO: 64 | D-REV, SEQ ID NO: 65 |
| Broccoli (SEQ ID NO: 62) | C-FWD, SEQ ID NO: 64 | D-REV, SEQ ID NO: 65 |

The amplified products were of the expected sizes.

The foregoing examples are provided by way of illustration only. One of skill in the art will appreciate that numerous variations on the biological molecules and methods described above may be employed to make and use the ELF3 gene, corresponding protein, and promoter region. We claim all such subject matter that falls within the scope and spirit of the following claims.

REFERENCES

Ainley et al. (1993) *Plant Mol. Biol.* 22:13–23.
Altschul et al. (1990). *J. Mol. Biol.*, 215, 403–10
Altschul et al. (1994). *Nature Genet.*, 6, 119–29.
An et al. (1988) *Plant Physiol.* 88:547.
Aronson et al. (1994) *Science* 263:1578–1584.
Ausubel et al. (1987) In *Current Protocols in Molecular Biology*, Greene Publishing Associates and Wiley-Intersciences.
Benfey and Chua (1990) *Science* 250:959–966.
Bernier (1988) *Ann. Rev. Plant Phys. and Plant Mol. Bio.* 39:175–219.
Bustos et al. (1989) *Plant Cell* 1:839.
Callis et al. (1988) *Plant Physiol.* 88:965.
Carpenter et al. (1992) *The Plant Cell* 4:557–571.
Chang et al. (1994) *Plant J.* 5:551–558.
Chang et al. (1986) *Mol. And Cell. Biol.* 6:1812–1819.
Corpet et al. (1988). *Nucleic Acids Research* 16, 10881–90.
Dekeyser et al. (1990) *Plant Cell* 2:591.
Denis et al. (1993) *Plant Physiol.* 101: 1295–1304.
Dunlap (1993) *Annu. Rev. Physiol.* 55:683.
Edery et al. (1994) *Science* 263:237–240.
Fromm et al. (1989) *Plant Cell* 1:977.
Gatz et al. (1997) *Ann. Rev. Plant Physiol. Plant Mol. Biol.* 48:89–108.
Gelvin et al. (1990) *Plant Molecular Biology Manual*, Kluwer Academic Publishers.
Gilmartin et al. (1992) *The Plant Cell* 4:839–949.
Hall (1990) *Ann. Rev. Genet.* 24:659.
Harlow & Lane (1988) *Antibodies, A Laboratory Manual*, Cold Spring Harbor Laboratory, New York.
Hicks et al. (1996) *Science* 274(5288):790–792.
Higgins and Sharp (1988). *Gene,* 73: 237–244.
Higgins and Sharp (1989). *CABIOS* 5: 151–153.
Huang et al. (1992). *Computer Applications in the Biosciences* 8, 155–65.
Hülskamp et al. (1990) *Nature* 346:577–580.
Innis et al. (eds.) (1990) *PCR Protocols, A Guide to Methods and Applications*, Academic Press, Inc., San Diego, Calif.
Jones et al. (1992) *Transgenic Res.* 1:285–297.
Katavic et al. (1994) *Mol. Gen. Genet.* 245:363–370.
Koornneef et al. (1991) *Mol. Gen. Genet.* 229:57–66.
Kuhlemeier et al. (1989) *Plant Cell* 1:471.
Lambie and Kimble (1991) *Development* 112:231–240.
Liang & Richardson (1993) *J. Agric. Food Chem.* 41:1800–1807.
Marcotte et al. (1989) *Plant Cell* 1:969.
Millar et al. (1995a) *Science* 267(5201):1163–1166.
Millar et al. (1995b) *Science* 267(5201):1161–1163.
Millar et al. (1992) *Plant Cell* 4:1075–1087.
Millar and Kay (1991) *Plant Cell* 3:541–550.
Mozo et al. (1998) *Mo. Gen. Genet.* 258(5):562–570.
Murfet (1985) *Pisum sativum*. In *Handbook of Flowering Plants Vol. IV*, ed. A. H. Halevy. (CRC Press: Boca Raton, Fla.), pp. 97–126.
Needleman and Wunsch (1970). *J. Mol. Biol.* 48:443.
Newman et al. (1994) *Plant Physiol.* 106(4): 1241–1255.
Odel et al. (1985) *Nature* 313:810.
Opperman et al. (1993) *Science* 263:221–223.
Pearson and Lipman (1988). *Proc. Natl. Acad. Sci. USA* 85:2444.
Pearson et al. (1994). *Methods in Molecular Biology* 24, 307–31.
Pouwels et al. (1987) *Cloning Vectors: A Laboratory Manual,* 1985, supp.
Roshal et al. (1987) *EMBO J.* 6:1155.
Sambrook et al. (1989) In *Molecular Cloning: A Laboratory Manual*, Cold Spring Harbor, N.Y.
Schaffer et al. (1998) *Cell* 93:1219–1229.
Schaffner & Sheen (1991) *Plant Cell* 3:997.
Schernthaner et al. (1988) *EMBO J.* 7:1249.
Shannon and Meeks-Wagner (1991) *Plant Cell* 3:877–892.
Siebertz et al. (1989) *Plant Cell* 1:961.
Smith et al. (1985) *Science* 229:1219–1224.
Smith and Waterman (1981). *Adv. Appl. Math.* 2:482.
Stockhause et al. (1997) *The Plant Cell* 9:479–489.
Terada & Shimamoto (1990) *Mol. Gen. Genet.* 220:389.
Tijssen (1993). *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, N.Y.
Wang & Tobin (1998) *Cell* 93:1207–1217.
Weissbach & Weissbach (1989) *Methods for Plant Molecular Biology*, Academic Press.
Zagotta et al. (1992) *Aust. J. Plant Physiol.* 19:411–418.
Zagotta et al. (1996) *Plant J.* 10(4):691–702.

We claim:

1. A purified protein having ELF3 protein biological activity, the amino acid sequence of which comprises
   (a) an amino acid sequence set forth as SEQ ID NO: 13, or
   (b) an amino acid sequence having at least 95% sequence identity to the sequence specified in (a).

2. The purified protein of claim 1, comprising the amino acid sequence of SEQ ID NO: 13.

3. The purified protein of claim 1, comprising an amino acid sequence having at least 95% sequence identity to SEQ ID NO: 13.

4. The purified protein of claim 1 bound by an anti-ELF3 protein antibody.

5. An isolated ELF3 protein consisting of the amino acid sequence of SEQ ID NO: 13.

6. A purified anti-ELF3 protein antibody that binds specifically to the protein of claim 1.

* * * * *

UNITED STATES PATENT AND TRADEMARK OFFICE
CERTIFICATE OF CORRECTION

| | | |
|---|---|---|
| PATENT NO. | : 7,053,182 B2 | Page 1 of 1 |
| APPLICATION NO. | : 11/109077 | |
| DATED | : May 30, 2006 | |
| INVENTOR(S) | : Wagner et al. | |

It is certified that error appears in the above-identified patent and that said Letters Patent is hereby corrected as shown below:

In the Specification, insert at Column 1, line 18:
--ACKNOWLEDGEMENT OF GOVERNMENT SUPPORT
This invention was made with government support under Grant No. MCB9507218 awarded by the National Science Foundation. The government has certain rights in the invention.--

Column 2, line 54, "Hηlskamp" should be --Hülskamp--
Column 6, line 61, "SEQ ID NO: 25" should be the start of a new paragraph
Column 20, line 10, "gene)" should be --gene).--
Column 22, line 32, "ab" should be --a/b--
Column 27, line 36, "Southern)" should be --Southern blot)--
Column 28, line 52, "used additional" should be --used to identify additional--
Column 165, line 3, "comprises" should be --comprises:--

Signed and Sealed this

Fourth Day of December, 2007

JON W. DUDAS
*Director of the United States Patent and Trademark Office*

SEQUENCE LISTING

<160> NUMBER OF SEQ ID NOS: 68

<210> SEQ ID NO 1
<211> LENGTH: 2518
<212> TYPE: DNA
<213> ORGANISM: Arabidopsis thaliana
<220> FEATURE:
<221> NAME/KEY: CDS
<222> LOCATION: (284)..(2371)

<400> SEQUENCE: 1

```
tgaaaactca ctttggtttt gtttgattcc tctttagtct gttttcgat ttcgttttct      60 ctgattggtt tggtggtgag atctctatcg tagtttgtcc tttgggttaa gatatttcat    120
ttgattggtg ggtttgtttt attgaagctt attgttgtga aagttggagt ctttctcagt    180
ttttaggttg aattattaag agaaagggaa gattttggt gtgaagttag gttatttggg     240
gtttgagaag tttgcaagtg aaaaaggttg tgaattgtga gtg atg aag aga ggg      295
                                             Met Lys Arg Gly
                                               1 aaa gat gag gag aag ata ttg gaa cct atg ttt cct cgg ctt cat gtg      343
Lys Asp Glu Glu Lys Ile Leu Glu Pro Met Phe Pro Arg Leu His Val
  5              10                  15                  20 aat gat gca gat aaa gga ggg cct aga gct cct cct aga aac aag atg      391
Asn Asp Ala Asp Lys Gly Gly Pro Arg Ala Pro Pro Arg Asn Lys Met
             25                  30                  35 gct ctt tat gag cag ctt agt att cct tct cag agg ttt ggt gat cat      439
Ala Leu Tyr Glu Gln Leu Ser Ile Pro Ser Gln Arg Phe Gly Asp His
         40                  45                  50 gga acg atg aat tct cgt agt aac aac aca agc act ttg gtt cat cct      487
Gly Thr Met Asn Ser Arg Ser Asn Asn Thr Ser Thr Leu Val His Pro
     55                  60                  65 gga cca tct agt cag cct tgt ggt gtg gaa aga aac tta tct gtc cag      535
Gly Pro Ser Ser Gln Pro Cys Gly Val Glu Arg Asn Leu Ser Val Gln
 70                  75                  80 cat ctt gat tct tca gcc gca aac caa gca act gag aag ttt gtc tcc      583
His Leu Asp Ser Ser Ala Ala Asn Gln Ala Thr Glu Lys Phe Val Ser
 85                  90                  95                 100 caa atg tcc ttc atg gaa aat gtg aga tct tcg gca cag cat gat cag      631
Gln Met Ser Phe Met Glu Asn Val Arg Ser Ser Ala Gln His Asp Gln
            105                 110                 115 agg aaa atg gtg aga gag gaa gaa gat ttt gca gtt cca gta tat att      679
Arg Lys Met Val Arg Glu Glu Glu Asp Phe Ala Val Pro Val Tyr Ile
        120                 125                 130 aac tca aga aga tct cag tct cat ggc aga acc aag agt ggt att gag      727
Asn Ser Arg Arg Ser Gln Ser His Gly Arg Thr Lys Ser Gly Ile Glu
    135                 140                 145 aag gaa aaa cac acc cca atg gtg gca cct agc tct cat cac tcc att      775
Lys Glu Lys His Thr Pro Met Val Ala Pro Ser Ser His His Ser Ile
150                 155                 160 cga ttt caa gaa gtg aat cag aca ggc tca aag caa aac gta tgt ttg      823
Arg Phe Gln Glu Val Asn Gln Thr Gly Ser Lys Gln Asn Val Cys Leu
165                 170                 175                 180 gct act tgt tca aaa cct gaa gtt agg gat cag gtc aag gcg aat gca      871
Ala Thr Cys Ser Lys Pro Glu Val Arg Asp Gln Val Lys Ala Asn Ala
                185                 190                 195 agg tca ggt ggc ttt gta atc tct tta gat gta tca gtc aca gag gag      919
Arg Ser Gly Gly Phe Val Ile Ser Leu Asp Val Ser Val Thr Glu Glu
            200                 205                 210
```

```
att gat ctc gaa aaa tca gca tca agt cat gat aga gta aat gat tat    967
Ile Asp Leu Glu Lys Ser Ala Ser Ser His Asp Arg Val Asn Asp Tyr
        215                 220                 225 aat gct tcc ttg aga caa gag tct aga aat cgg tta tac cga gat ggt   1015
Asn Ala Ser Leu Arg Gln Glu Ser Arg Asn Arg Leu Tyr Arg Asp Gly
    230                 235                 240 ggc aaa act cgt ctg aag gac act gat aat gga gct gaa tct cac ttg   1063
Gly Lys Thr Arg Leu Lys Asp Thr Asp Asn Gly Ala Glu Ser His Leu
245                 250                 255                 260 gca acg gaa aat cat tca caa gag ggt cat ggc agt cct gaa gac att   1111
Ala Thr Glu Asn His Ser Gln Glu Gly His Gly Ser Pro Glu Asp Ile
                265                 270                 275 gat aat gat cgt gaa tac agc aaa agc aga gca tgc gcc tct ctg cag   1159
Asp Asn Asp Arg Glu Tyr Ser Lys Ser Arg Ala Cys Ala Ser Leu Gln
            280                 285                 290 cag ata aat gaa gag gca agt gat gac gtt tct gat gat tcg atg gtg   1207
Gln Ile Asn Glu Glu Ala Ser Asp Asp Val Ser Asp Asp Ser Met Val
        295                 300                 305 gat tct ata tcc agc ata gat gtc tct ccc gat gat gtt gtg ggt ata   1255
Asp Ser Ile Ser Ser Ile Asp Val Ser Pro Asp Asp Val Val Gly Ile
    310                 315                 320 tta ggt caa aaa cgt ttc tgg aga gca agg aaa gcc att gcc aat caa   1303
Leu Gly Gln Lys Arg Phe Trp Arg Ala Arg Lys Ala Ile Ala Asn Gln
325                 330                 335                 340 caa aga gta ttt gct gtt caa cta ttt gag ttg cac aga ctg att aag   1351
Gln Arg Val Phe Ala Val Gln Leu Phe Glu Leu His Arg Leu Ile Lys
                345                 350                 355 gtt caa aaa ctt att gct gca tca ccg gat ctc ttg ctc gat gag atc   1399
Val Gln Lys Leu Ile Ala Ala Ser Pro Asp Leu Leu Leu Asp Glu Ile
            360                 365                 370 agt ttt ctt gga aaa gtt tct gct aaa agc tat cca gtg aag aag ctc   1447
Ser Phe Leu Gly Lys Val Ser Ala Lys Ser Tyr Pro Val Lys Lys Leu
        375                 380                 385 ctt cca tca gaa ttt ctg gta aag cct cct cta cca cat gtt gtc gtc   1495
Leu Pro Ser Glu Phe Leu Val Lys Pro Pro Leu Pro His Val Val Val
    390                 395                 400 aaa caa agg ggt gac tcg gag aag act gac caa cat aaa atg gaa agc   1543
Lys Gln Arg Gly Asp Ser Glu Lys Thr Asp Gln His Lys Met Glu Ser
405                 410                 415                 420 tca gct gag aac gta gtt ggg agg ttg tca aat caa ggt cat cat caa   1591
Ser Ala Glu Asn Val Val Gly Arg Leu Ser Asn Gln Gly His His Gln
                425                 430                 435 caa tcc aac tac atg cct ttt gca aac aac cca ccg gct tca ccg gct   1639
Gln Ser Asn Tyr Met Pro Phe Ala Asn Asn Pro Pro Ala Ser Pro Ala
            440                 445                 450 cca aat gga tat tgc ttt cct cct cag cct cct cct tca gga aat cat   1687
Pro Asn Gly Tyr Cys Phe Pro Pro Gln Pro Pro Pro Ser Gly Asn His
        455                 460                 465 cag caa tgg ttg atc cct gta atg tct ccc tcg gaa gga ctg ata tac   1735
Gln Gln Trp Leu Ile Pro Val Met Ser Pro Ser Glu Gly Leu Ile Tyr
    470                 475                 480 aag cct cac cca ggt atg gca cac acg ggg cat tat gga gga tat tat   1783
Lys Pro His Pro Gly Met Ala His Thr Gly His Tyr Gly Gly Tyr Tyr
485                 490                 495                 500 ggt cat tat atg cct aca cca atg gta atg cct caa tat cac ccc ggc   1831
Gly His Tyr Met Pro Thr Pro Met Val Met Pro Gln Tyr His Pro Gly
                505                 510                 515 atg gga ttc cca cct cct ggt aat ggc tac ttc cct cca tat gga atg   1879
Met Gly Phe Pro Pro Pro Gly Asn Gly Tyr Phe Pro Pro Tyr Gly Met
            520                 525                 530
```

```
atg ccc acc ata atg aac cca tat tgt tca agc caa caa caa caa         1927
Met Pro Thr Ile Met Asn Pro Tyr Cys Ser Gln Gln Gln Gln
    535                 540                 545 caa caa ccc aat gag caa atg aac cag ttt gga cat cct gga aat ctt     1975
Gln Gln Pro Asn Glu Gln Met Asn Gln Phe Gly His Pro Gly Asn Leu
550                 555                 560 cag aac acc caa caa caa caa cag aga tct gat aat gaa cct gct cca     2023
Gln Asn Thr Gln Gln Gln Gln Arg Ser Asp Asn Glu Pro Ala Pro
565                 570                 575                 580 cag caa cag caa cag cca aca aag tct tat ccg cga gca aga aag agc     2071
Gln Gln Gln Gln Gln Pro Thr Lys Ser Tyr Pro Arg Ala Arg Lys Ser
                585                 590                 595 agg caa ggg agc aca gga agc agt cca agt ggg cca cag gga atc tct     2119
Arg Gln Gly Ser Thr Gly Ser Ser Pro Ser Gly Pro Gln Gly Ile Ser
                600                 605                 610 ggt agc aag tcc ttt cgg cca ttc gca gcc gtt gat gag gac agc aac     2167
Gly Ser Lys Ser Phe Arg Pro Phe Ala Ala Val Asp Glu Asp Ser Asn
                615                 620                 625 atc aac aat gca cct gag caa acg atg aca aca acc aca acg acg aca     2215
Ile Asn Asn Ala Pro Glu Gln Thr Met Thr Thr Thr Thr Thr Thr Thr
630                 635                 640 aga aca act gtt act cag aca aca aga gat ggg gga gga gtg acg aga     2263
Arg Thr Thr Val Thr Gln Thr Thr Arg Asp Gly Gly Gly Val Thr Arg
645                 650                 655                 660 gtg ata aag gtg gta cct cac aac gca aag ctc gcg agt gag aat gct     2311
Val Ile Lys Val Val Pro His Asn Ala Lys Leu Ala Ser Glu Asn Ala
                665                 670                 675 gcc aga att ttc cag tca ata caa gaa gaa cgt aaa cgc tat gac tcc     2359
Ala Arg Ile Phe Gln Ser Ile Gln Glu Glu Arg Lys Arg Tyr Asp Ser
                680                 685                 690 tct aag cct taa tcctctctat gcgtattgta cttgatatgt attttacaaa         2411
Ser Lys Pro
        695 attagaaaaa ttgtgataga tgttatcctc aatatatgta ccatgtaaac gtattatggt  2471 gtaagcctca tttatatgtg ttaatttgtc ttaaaaaaaa aaaaaaa                 2518

<210> SEQ ID NO 2
<211> LENGTH: 695
<212> TYPE: PRT
<213> ORGANISM: Arabidopsis thaliana

<400> SEQUENCE: 2

Met Lys Arg Gly Lys Asp Glu Glu Lys Ile Leu Glu Pro Met Phe Pro
1               5                   10                  15

Arg Leu His Val Asn Asp Ala Asp Lys Gly Gly Pro Arg Ala Pro Pro
                20                  25                  30

Arg Asn Lys Met Ala Leu Tyr Glu Gln Leu Ser Ile Pro Ser Gln Arg
            35                  40                  45

Phe Gly Asp His Gly Thr Met Asn Ser Arg Ser Asn Asn Thr Ser Thr
        50                  55                  60

Leu Val His Pro Gly Pro Ser Gln Pro Cys Gly Val Glu Arg Asn
65                  70                  75                  80

Leu Ser Val Gln His Leu Asp Ser Ser Ala Ala Asn Gln Ala Thr Glu
                85                  90                  95

Lys Phe Val Ser Gln Met Ser Phe Met Glu Asn Val Arg Ser Ser Ala
            100                 105                 110
```

-continued

```
Gln His Asp Gln Arg Lys Met Val Arg Glu Glu Asp Phe Ala Val
        115                 120                 125
Pro Val Tyr Ile Asn Ser Arg Arg Ser Gln Ser His Gly Arg Thr Lys
130                 135                 140
Ser Gly Ile Glu Lys Glu Lys His Thr Pro Met Val Ala Pro Ser Ser
145                 150                 155                 160
His His Ser Ile Arg Phe Gln Glu Val Asn Gln Thr Gly Ser Lys Gln
                165                 170                 175
Asn Val Cys Leu Ala Thr Cys Ser Lys Pro Glu Val Arg Asp Gln Val
            180                 185                 190
Lys Ala Asn Ala Arg Ser Gly Gly Phe Val Ile Ser Leu Asp Val Ser
        195                 200                 205
Val Thr Glu Glu Ile Asp Leu Glu Lys Ser Ala Ser Ser His Asp Arg
    210                 215                 220
Val Asn Asp Tyr Asn Ala Ser Leu Arg Gln Glu Ser Arg Asn Arg Leu
225                 230                 235                 240
Tyr Arg Asp Gly Gly Lys Thr Arg Leu Lys Asp Thr Asp Asn Gly Ala
                245                 250                 255
Glu Ser His Leu Ala Thr Glu Asn His Ser Gln Glu Gly His Gly Ser
            260                 265                 270
Pro Glu Asp Ile Asp Asn Asp Arg Glu Tyr Ser Lys Ser Arg Ala Cys
        275                 280                 285
Ala Ser Leu Gln Gln Ile Asn Glu Glu Ala Ser Asp Asp Val Ser Asp
    290                 295                 300
Asp Ser Met Val Asp Ser Ile Ser Ser Ile Asp Val Ser Pro Asp Asp
305                 310                 315                 320
Val Val Gly Ile Leu Gly Gln Lys Arg Phe Trp Arg Ala Arg Lys Ala
                325                 330                 335
Ile Ala Asn Gln Gln Arg Val Phe Ala Val Gln Leu Phe Glu Leu His
            340                 345                 350
Arg Leu Ile Lys Val Gln Lys Leu Ile Ala Ala Ser Pro Asp Leu Leu
        355                 360                 365
Leu Asp Glu Ile Ser Phe Leu Gly Lys Val Ser Ala Lys Ser Tyr Pro
    370                 375                 380
Val Lys Lys Leu Leu Pro Ser Glu Phe Leu Val Lys Pro Pro Leu Pro
385                 390                 395                 400
His Val Val Lys Gln Arg Gly Asp Ser Glu Lys Thr Asp Gln His
                405                 410                 415
Lys Met Glu Ser Ser Ala Glu Asn Val Val Gly Arg Leu Ser Asn Gln
            420                 425                 430
Gly His His Gln Gln Ser Asn Tyr Met Pro Phe Ala Asn Asn Pro Pro
        435                 440                 445
Ala Ser Pro Ala Pro Asn Gly Tyr Cys Phe Pro Pro Gln Pro Pro Pro
    450                 455                 460
Ser Gly Asn His Gln Gln Trp Leu Ile Pro Val Met Ser Pro Ser Glu
465                 470                 475                 480
Gly Leu Ile Tyr Lys Pro His Pro Gly Met Ala His Thr Gly His Tyr
                485                 490                 495
Gly Gly Tyr Tyr Gly His Tyr Met Pro Thr Pro Met Val Met Pro Gln
            500                 505                 510
Tyr His Pro Gly Met Gly Phe Pro Pro Pro Gly Asn Gly Tyr Phe Pro
        515                 520                 525
```

```
Pro Tyr Gly Met Met Pro Thr Ile Met Asn Pro Tyr Cys Ser Ser Gln
        530                 535                 540

Gln Gln Gln Gln Gln Gln Pro Asn Glu Gln Met Asn Gln Phe Gly His
545                 550                 555                 560

Pro Gly Asn Leu Gln Asn Thr Gln Gln Gln Gln Arg Ser Asp Asn
            565                 570                 575

Glu Pro Ala Pro Gln Gln Gln Gln Pro Thr Lys Ser Tyr Pro Arg
            580                 585                 590

Ala Arg Lys Ser Arg Gln Gly Ser Thr Gly Ser Ser Pro Gly Pro
        595                 600                 605

Gln Gly Ile Ser Gly Ser Lys Ser Phe Arg Pro Phe Ala Val Asp
        610                 615                 620

Glu Asp Ser Asn Ile Asn Asn Ala Pro Glu Gln Thr Met Thr Thr Thr
625                 630                 635                 640

Thr Thr Thr Thr Arg Thr Thr Val Thr Gln Thr Thr Arg Asp Gly Gly
            645                 650                 655

Gly Val Thr Arg Val Ile Lys Val Val Pro His Asn Ala Lys Leu Ala
        660                 665                 670

Ser Glu Asn Ala Ala Arg Ile Phe Gln Ser Ile Gln Glu Glu Arg Lys
    675                 680                 685

Arg Tyr Asp Ser Ser Lys Pro
    690                 695

<210> SEQ ID NO 3
<211> LENGTH: 4221
<212> TYPE: DNA
<213> ORGANISM: Arabidopsis thaliana
<220> FEATURE:
<221> NAME/KEY: promoter
<222> LOCATION: (1)..(142)
<220> FEATURE:
<221> NAME/KEY: 5'UTR
<222> LOCATION: (143)..(425)
<220> FEATURE:
<221> NAME/KEY: exon
<222> LOCATION: (426)..(644)
<220> FEATURE:
<221> NAME/KEY: Intron
<222> LOCATION: (645)..(1006)
<220> FEATURE:
<221> NAME/KEY: exon
<222> LOCATION: (1007)..(1803)
<220> FEATURE:
<221> NAME/KEY: Intron
<222> LOCATION: (1804)..(2983)
<220> FEATURE:
<221> NAME/KEY: exon
<222> LOCATION: (2984)..(3037)
<220> FEATURE:
<221> NAME/KEY: Intron
<222> LOCATION: (3038)..(3127)
<220> FEATURE:
<221> NAME/KEY: exon
<222> LOCATION: (3128)..(4142)
<220> FEATURE:
<221> NAME/KEY: 3'UTR
<222> LOCATION: (4146)..(4221)

<400> SEQUENCE: 3
tatctttggg ggctccactt ttcctatctc tttttgcccc tttcctctct ctgttcacaa      60
gtcatcttct tccttcctct gaatcttgtt ccttttgct ctctctactt gattcaccca     120 ctctgttttct cgattagtac gttgaaaact cactttggtt ttgtttgatt cctctttagt    180 ctgttttcg atttcgtttt ctctgattgg tttggtggtg agatctctat cgtagtttgt     240
```

-continued

```
cctttgggtt aagatatttc atttgattgg tgggtttgtt ttattgaagc ttattgttgt      300
gaaagttgga gtctttctca gttttttaggt tgaattatta agagaaaggg aagattttg      360 gtgtgaagtt aggttatttg gggtttgaga agtttgcaag tgaaaaaggt tgtgaattgt      420 gagtg atg aag aga ggg aaa gat gag gag aag ata ttg gaa cct atg ttt     470
      Met Lys Arg Gly Lys Asp Glu Glu Lys Ile Leu Glu Pro Met Phe
      1               5                   10                  15 cct cgg ctt cat gtg aat gat gca gat aaa gga ggg cct aga gct cct       518
Pro Arg Leu His Val Asn Asp Ala Asp Lys Gly Gly Pro Arg Ala Pro
            20                  25                  30 cct aga aac aag atg gct ctt tat gag cag ctt agt att cct tct cag       566
Pro Arg Asn Lys Met Ala Leu Tyr Glu Gln Leu Ser Ile Pro Ser Gln
                35                  40                  45 agg ttt ggt gat cat gga acg atg aat tct cgt agt aac aac aca agc       614
Arg Phe Gly Asp His Gly Thr Met Asn Ser Arg Ser Asn Asn Thr Ser
            50                  55                  60 act ttg gtt cat cct gga cca tct agt cag gtattgtttt gattttgatc         664
Thr Leu Val His Pro Gly Pro Ser Ser Gln
65                  70 attgtatagg ctcttgatgt tattagttgt atgagtttgg atgttatata gcctgaaaga     724
gaaagtagga cattggttga tctatgtttc aattgttatc agatcatagt atcttctttt     784
tgcttatgga ttgagctttt aggattgaat ctcctgtat atatgagagt cttgtagaca      844
caagtttatc taagtgtggt ttatttctta aaactaacat tcttgttgtg cctgattctt     904
tttatgttct gaagttcgat gaaagttttct tgtgattgcc ctgagcattc agactattgc    964
aaggacatga gaaataatcc ttttttaccc tcttcaatgc ag cct tgt ggt gtg        1018
                                              Pro Cys Gly Val
                                                      75 gaa aga aac tta tct gtc cag cat ctt gat tct tca gcc gca aac caa       1066
Glu Arg Asn Leu Ser Val Gln His Leu Asp Ser Ser Ala Ala Asn Gln
            80                  85                  90 gca act gag aag ttt gtc tcc caa atg tcc ttc atg gaa aat gtg aga       1114
Ala Thr Glu Lys Phe Val Ser Gln Met Ser Phe Met Glu Asn Val Arg
        95                  100                 105 tct tcg gca cag cat gat cag agg aaa atg gtg aga gag gaa gaa gat       1162
Ser Ser Ala Gln His Asp Gln Arg Lys Met Val Arg Glu Glu Glu Asp
110                 115                 120                 125 ttt gca gtt cca gta tat att aac tca aga aga tct cag tct cat ggc       1210
Phe Ala Val Pro Val Tyr Ile Asn Ser Arg Arg Ser Gln Ser His Gly
                130                 135                 140 aga acc aag agt ggt att gag aag gaa aaa cac acc cca atg gtg gca       1258
Arg Thr Lys Ser Gly Ile Glu Lys Glu Lys His Thr Pro Met Val Ala
            145                 150                 155 cct agc tct cat cac tcc att cga ttt caa gaa gtg aat cag aca ggc       1306
Pro Ser Ser His His Ser Ile Arg Phe Gln Glu Val Asn Gln Thr Gly
                160                 165                 170 tca aag caa aac gta tgt ttg gct act tgt tca aaa cct gaa gtt agg       1354
Ser Lys Gln Asn Val Cys Leu Ala Thr Cys Ser Lys Pro Glu Val Arg
175                 180                 185 gat cag gtc aag gcg aat gca agg tca ggt ggc ttt gta atc tct tta       1402
Asp Gln Val Lys Ala Asn Ala Arg Ser Gly Gly Phe Val Ile Ser Leu
190                 195                 200                 205 gat gta tca gtc aca gag gag att gat ctc gaa aaa tca gca tca agt       1450
Asp Val Ser Val Thr Glu Glu Ile Asp Leu Glu Lys Ser Ala Ser Ser
                210                 215                 220
```

-continued

```
cat gat aga gta aat gat tat aat gct tcc ttg aga caa gag tct aga        1498
His Asp Arg Val Asn Asp Tyr Asn Ala Ser Leu Arg Gln Glu Ser Arg
            225                 230                 235 aat cgg tta tac cga gat ggt ggc aaa act cgt ctg aag gac act gat        1546
Asn Arg Leu Tyr Arg Asp Gly Gly Lys Thr Arg Leu Lys Asp Thr Asp
        240                 245                 250 aat gga gct gaa tct cac ttg gca acg gaa aat cat tca caa gag ggt        1594
Asn Gly Ala Glu Ser His Leu Ala Thr Glu Asn His Ser Gln Glu Gly
    255                 260                 265 cat ggc agt cct gaa gac att gat aat gat cgt gaa tac agc aaa agc        1642
His Gly Ser Pro Glu Asp Ile Asp Asn Asp Arg Glu Tyr Ser Lys Ser
270                 275                 280                 285 aga gca tgc gcc tct ctg cag cag ata aat gaa gag gca agt gat gac        1690
Arg Ala Cys Ala Ser Leu Gln Gln Ile Asn Glu Glu Ala Ser Asp Asp
                290                 295                 300 gtt tct gat gat tcg atg gtg gat tct ata tcc agc ata gat gtc tct        1738
Val Ser Asp Asp Ser Met Val Asp Ser Ile Ser Ser Ile Asp Val Ser
            305                 310                 315 ccc gat gat gtt gtg ggt ata tta ggt caa aaa cgt ttc tgg aga gca        1786
Pro Asp Asp Val Val Gly Ile Leu Gly Gln Lys Arg Phe Trp Arg Ala
        320                 325                 330 agg aaa gcc att gcc aa  gtaagttcac tagaaattta cagtttggtt              1833
Arg Lys Ala Ile Ala Asn
    335 atttattctc cgctctttct atttatctcc ttctttgata ccaacatttt ttgcttgaaa    1893 gaagttaata tttaagcatt gttccgtagt cttactgaag cttttcctc tgttgttttt      1953 tgctattttc attgaggact gtggtagggc atatttcact atcaccaaat ttcaaatttc    2013 tagaacactc tccttcatat tttttttcat gattaatgct gcaattgatt gctgatatac    2073 atatatgact ataactcagt ttcatattct gtctcatttt gggagaaaga gatttcaggt    2133 ttatgcttga gaagtgatgg ttctatagtt gagaggcccc tgattcatct aaaatggtcc    2193 tattatgtgt ttagttgtag agtcctcggt agaatattaa cgcgtttaac acgttggatc    2253 atgttatagc agggagggac attctctgtt gacctatatt gtgcaaggtg cccgccgatg    2313 gctttattac tataccttct ttgcatctgg ttgttggaac atgtccctgt ctcggtttgg    2373 tattgctttt attctgcact gtcgtcttgg gcatttcccc tacttgtcat tcaaggggtt    2433 gaaccaggta gggaaatgtt tttccgagga ccccaggatc taaattttag ttaaccatac    2493 gtaaagttag ttttgagtct tatgacgatg cagaattata gtttcttctt actactgctt    2553 aagaggatcc ttagtgtggt tgtgaactac agagttttta tgattgtagg cttcatgact    2613 taactttaa ggttcaatgt actctaatcc atatggtaag gtatcggatt cacgaccaat     2673 gcaaataata agatttttat ttcttgcttc ttgttaaata tctgacatct cattttgcag    2733 aggataagct gcgctgtaag ctagatttca ataagcccgt cctttgcatt gttatctatg    2793 ctttaatatg tcattggacc cattgatttg gttttcttct atctttttg attggctatg     2853 tattcttgtt tctttttcc tatctcattt cgatcgtatt gttccattag ctgttcaacc     2913 taaactatgt ctctctttgt tgaacttttg atggataatc ttcttaatgt gactctgttt    2973 ctcattacag t caa caa aga gta ttt gct gtt caa cta ttt gag ttg cac     3023
              Gln Gln Arg Val Phe Ala Val Gln Leu Phe Glu Leu His
              340                 345                 350 aga ctg att aag gt  aaagtcattc agaaacttct catatgtttc catgagtatt      3077
Arg Leu Ile Lys Val
        355
```

```
                                                              -continued tgtttcttct cgagctgaaa caaacctctt caactgtgta ataatcaggt t caa aaa        3134
                                                         Gln Lys ctt att gct gca tca ccg gat ctc ttg ctc gat gag atc agt ttt ctt        3182
Leu Ile Ala Ala Ser Pro Asp Leu Leu Leu Asp Glu Ile Ser Phe Leu
360             365                 370                 375 gga aaa gtt tct gct aaa agc tat cca gtg aag aag ctc ctt cca tca        3230
Gly Lys Val Ser Ala Lys Ser Tyr Pro Val Lys Lys Leu Leu Pro Ser
            380                 385                 390 gaa ttt ctg gta aag cct cct cta cca cat gtt gtc gtc aaa caa agg        3278
Glu Phe Leu Val Lys Pro Pro Leu Pro His Val Val Val Lys Gln Arg
        395                 400                 405 ggt gac tcg gag aag act gac caa cat aaa atg gaa agc tca gct gag        3326
Gly Asp Ser Glu Lys Thr Asp Gln His Lys Met Glu Ser Ser Ala Glu
    410                 415                 420 aac gta gtt ggg agg ttg tca aat caa ggt cat cat caa caa tcc aac        3374
Asn Val Val Gly Arg Leu Ser Asn Gln Gly His His Gln Gln Ser Asn
425                 430                 435 tac atg cct ttt gca aac aac cca ccg gct tca ccg gct cca aat gga        3422
Tyr Met Pro Phe Ala Asn Asn Pro Pro Ala Ser Pro Ala Pro Asn Gly
440             445                 450                 455 tat tgc ttt cct cct cag cct cct cct tca gga aat cat cag caa tgg        3470
Tyr Cys Phe Pro Pro Gln Pro Pro Pro Ser Gly Asn His Gln Gln Trp
            460                 465                 470 ttg atc cct gta atg tct ccc tcg gaa gga ctg ata tac aag cct cac        3518
Leu Ile Pro Val Met Ser Pro Ser Glu Gly Leu Ile Tyr Lys Pro His
        475                 480                 485 cca ggt atg gca cac acg ggg cat tat gga gga tat tat ggt cat tat        3566
Pro Gly Met Ala His Thr Gly His Tyr Gly Gly Tyr Tyr Gly His Tyr
    490                 495                 500 atg cct aca cca atg gta atg cct caa tat cac ccc ggc atg gga ttc        3614
Met Pro Thr Pro Met Val Met Pro Gln Tyr His Pro Gly Met Gly Phe
505                 510                 515 cca cct cct ggt aat ggc tac ttc cct cca tat gga atg atg ccc acc        3662
Pro Pro Pro Gly Asn Gly Tyr Phe Pro Pro Tyr Gly Met Met Pro Thr
520             525                 530                 535 ata atg aac cca tat tgt tca agc caa caa caa caa caa caa ccc            3710
Ile Met Asn Pro Tyr Cys Ser Ser Gln Gln Gln Gln Gln Gln Pro
            540                 545                 550 aat gag caa atg aac cag ttt gga cat cct gga aat ctt cag aac acc        3758
Asn Glu Gln Met Asn Gln Phe Gly His Pro Gly Asn Leu Gln Asn Thr
        555                 560                 565 caa caa caa caa cag aga tct gat aat gaa cct gct cca cag caa cag        3806
Gln Gln Gln Gln Gln Arg Ser Asp Asn Glu Pro Ala Pro Gln Gln Gln
    570                 575                 580 caa cag cca aca aag tct tat ccg cga gca aga aag agc agg caa ggg        3854
Gln Gln Pro Thr Lys Ser Tyr Pro Arg Ala Arg Lys Ser Arg Gln Gly
585                 590                 595 agc aca gga agc agt cca agt ggg cca cag gga atc tct ggt agc aag        3902
Ser Thr Gly Ser Ser Pro Ser Gly Pro Gln Gly Ile Ser Gly Ser Lys
            600                 605                 610                 615 tcc ttt cgg cca ttc gca gcc gtt gat gag gac agc aac atc aac aat        3950
Ser Phe Arg Pro Phe Ala Ala Val Asp Glu Asp Ser Asn Ile Asn Asn
        620                 625                 630 gca cct gag caa acg atg aca aca acc aca acg aca aga aca act            3998
Ala Pro Glu Gln Thr Met Thr Thr Thr Thr Thr Thr Arg Thr Thr
    635                 640                 645 gtt act cag aca aca aga gat ggg gga gga gtg acg aga gta ata aag        4046
Val Thr Gln Thr Thr Arg Asp Gly Gly Gly Val Thr Arg Val Ile Lys
650                 655                 660
```

-continued

| gtg Val 665 | gta Val | cct Pro | cac His | aac Asn | gca Ala 670 | aag Lys | ctc Leu | gcg Ala | agt Ser | gag Glu 675 | aat Asn | gct Ala | gcc Ala | aga Arg | att Ile | 4094 |

| ttc Phe 680 | cag Gln | tca Ser | ata Ile | caa Gln | gaa Glu 685 | gaa Glu | cgt Arg | aaa Lys | cgc Arg | tat Tyr 690 | gac Asp | tcc Ser | tct Ser | aag Lys | cct Pro 695 | 4142 |

| taatcctctc tatgcgtatt gtacttgata tgtattttac aaaattagaa aaattgtgat | 4202 |
| agatgttatc ctcaatata | 4221 |

<210> SEQ ID NO 4
<211> LENGTH: 2088
<212> TYPE: DNA
<213> ORGANISM: Arabidopsis thaliana

<400> SEQUENCE: 4

| atgaagagag ggaaagatga ggagaagata ttggaaccta tgtttcctcg gcttcatgtg | 60 |
| aatgatgcag ataaaggagg cctagagct cctcctagaa acaagatggc tctttatgag | 120 |
| cagcttagta ttccttctca gaggtttggt gatcatggaa cgatgaattc tcgtagtaac | 180 |
| aacacaagca ctttggttca tcctggacca tctagtcagc cttgtggtgt ggaaagaaac | 240 |
| ttatctgtcc agcatcttga ttcttcagcc gcaaaccaag caactgagaa gtttgtctcc | 300 |
| caaatgtcct tcatggaaaa tgtgagatct tcggcacagc atgatcagag gaaaatggtg | 360 |
| agagaggaag aagattttgc agttccagta tatattaact caagaagatc tcagtctcat | 420 |
| ggcagaacca gagtggtat tgagaaggaa aaacacaccc caatggtggc acctagctct | 480 |
| catcactcca ttcgatttca agaagtgaat cagacaggct caaagcaaaa cgtatgtttg | 540 |
| gctacttgtt caaaacctga agttagggat caggtcaagg cgaatgcaag gtcaggtggc | 600 |
| tttgtaatct ctttagatgt atcagtcaca gaggagattg atctcgaaaa atcagcatca | 660 |
| agtcatgata gagtaaatga ttataatgct tccttgagac aagagtctag aaatcggtta | 720 |
| taccgagatg gtggcaaaac tcgtctgaag gacactgata tggagctga atctcacttg | 780 |
| gcaacggaaa atcattcaca agagggtcat ggcagtcctg aagacattga taatgatcgt | 840 |
| gaatacagca aaagcagagc atgcgcctct ctgcagcaga taaatgaaga ggcaagtgat | 900 |
| gacgtttctg atgattcgat ggtggattct atatccagca tagatgtctc tcccgatgat | 960 |
| gttgtgggta tattaggtca aaaacgtttc tggagagcaa ggaaagccat tgccaatcaa | 1020 |
| caaagagtat ttgctgttca actatttgag ttgcacagac tgattaaggt tcaaaaactt | 1080 |
| attgctgcat caccggatct cttgctcgat gagatcagtt ttcttggaaa agtttctgct | 1140 |
| aaaagctatc cagtgaagaa gctccttcca tcagaatttc tggtaaagcc tcctctacca | 1200 |
| catgttgtcg tcaaacaaag gggtgactcg agaagactg accaacataa aatggaaagc | 1260 |
| tcagctgaga acgtagttgg gaggttgtca aatcaaggtc atcatcaaca atccaactac | 1320 |
| atgcctttg caaacaaccc accggcttca ccggctccaa atggatattg ctttcctcct | 1380 |
| cagcctcctc cttcaggaaa tcatcagcaa tggttgatcc ctgtaatgtc tccctcggaa | 1440 |
| ggactgatat acaagcctca cccaggtatg cacacacgg gcattatgg aggatattat | 1500 |
| ggtcattata tgcctacacc aatggtaatg cctcaatatc accccggcat gggattccca | 1560 |
| cctcctggta atggctactt ccctccatat ggaatgatgc ccaccataat gaacccatat | 1620 |
| tgttcaagcc aacaacaaca caacaacaa cccaatgagc aaatgaacca gtttggacat | 1680 |
| cctggaaatc ttcagaacac ccaacaacaa caacagagat ctgataatga acctgctcca | 1740 |
| cagcaacagc aacagccaac aaagtcttat ccgcgagcaa gaaagagcag gcaagggagc | 1800 |

```
acaggaagca gtccaagtgg gccacaggga atctctggta gcaagtcctt tcggccattc    1860
gcagccgttg atgaggacag caacatcaac aatgcacctg agcaaacgat gacaacaacc    1920
acaacgacga caagaacaac tgttactcag acaacaagag atgggggagg agtgacgaga    1980
gtgataaagg tggtacctca caacgcaaag ctcgcgagtg agaatgctgc cagaattttc    2040
cagtcaatac aagaagaacg taaacgctat gactcctcta agccttaa                 2088

<210> SEQ ID NO 5
<211> LENGTH: 4071
<212> TYPE: DNA
<213> ORGANISM: Arabidopsis thaliana

<400> SEQUENCE: 5
tgtgttagtg actttcctcc tgaagaattc aactcaagac atgagacaat agattcatga      60
caatatctac tacagtactt gcataacaca atgtaaaact aactaacaat tgatagttta     120
gtacacaatc caaattgcaa agagagata ctgcaaatga tctaatcaaa actcatgcat      180
tctacagttc cataagacat ttcaaatcac taatctgaag aaatatgatg cattaataac     240
aaatatttga taactaaaca gacatttgga tcagaaatga agttaaatta agcatttaat     300
tgcttaataa tttaattgat tgattcaaag gcgtaataac acaaaattct tcggggggaat    360 ttgaagggat agagcaaatc gcttagggta aatgaaaac agcgataagt aacgaattat      420
caaagtctga gttaagaatc aggaaattga gggattgaag aagaataaag ggacctggtt     480
caggaggaat tgagacgtga gtacgctgtg ttggagagga cgacgtcatt ttcgatcaaa     540
gcagcagatt cagcaacgga tggatgggtc tttactcttt gggctgaaga taaccgcaac     600
tagattcttc ctgagttttt ttttctttt tgataaaacg agagccctta caggtaaaaa      660
cccaataaaa accacgatcc attttttattt ggacatttaa tatttaatta ttttaaatta    720
gaaaataatt acacgaatta ctaaattgta taatatgata ttaaaaaatt aagtgttatt     780 gatgtgttt cggtctgact gtctataaaa aaaatcccca acataagag ttgttgttgg       840 agtcattaaa ggatcctaatg gtttgtggtg gtgtgaccat tggaggaggg tttgttgatg    900
ggtcgtgtgt ttcaccatta atattatcaa atggttctcg gttgattggt catttttgga     960
gtcatcaaat ggctcatatg ttacgctatg tatcacgaaa atatatattt ttctcttaaa    1020
accattcttc cttttccaat aatatggatt tataaattcc cgtgaagata aatatgtggt    1080 tttttacttttt cgtttttttc ctaggtgagg agggtgttat tggttgctaa tttaaaagga  1140
attttgatga ttttaataat atcataaaa gtaaattaag attttaaact attgctaggg     1200
agttttttta tgatcttgtt aattagtttt tcacagtctt gtaaagtttt tcaaacaatc    1260
tctctatttt gatgatattt ttttactttta ttttgtgaac aaaagtgtag aaaattatta   1320
aacaataaca caatatttta attcattaac aatcatagtt ttttttaaaa aaaaattgaa    1380
taacgccaaa cttttagtga ctttataatt ttttttaatta taaggtaagt ctcctaagat   1440
atatgttttg ggttaaagta ttcacaatgt ccaccatgtt atgtgatata ttacccatgt    1500
atattcattt tgtcatttaa tcttaccttt ttgcattttt gtttggctta aaatctacaa    1560
tatcgtttta ctattaaaaa aacctgtaat attcatttac aaatcaatat tttattcttt    1620
ttagacatat cctattttaa tttctacatt cttttcaaaa tagttactaa aataattttt    1680
ttctaaaagc catgaatata aacacaacaa ctaatcaatc tccacaatat atattatata    1740
ttaacaaaaa gtgtattggt gataaaaagt acttgatgat acactaaaca aaaaggataa    1800
```

```
atgggagaat tttttatttt gaaagatgaa acatttagg ttatatattt catgacccctt   1860
ataaataaaa ttcctggctc caccactgga tatctctaca tatttccaac atcaatatcc   1920
attgatattt gataatcttt accaaaaatt cgcaatctcc tttagagtga aagcgagtat   1980
aaccgtatga ccaaactatt tgagtacca ttggtaattc cttaccttaa gcttccagag    2040
gtattagtgc tatatattca tagtgccacc gagtattttg aactccgaaa tgatttctca   2100
ctatccgacc actcccaatt atataacatg cttagaatta ttcgtaagat ggatcgtagt   2160
tgcattttac gacaccatac aggacaagtc catgatagtt tgagttggtg gattttggaa   2220
cccctgcaaa tttattttat acataacaaa ggccccaatc cattccttag catcacaact   2280
tgggacttct atcttttgaa ggatacattc acttgttggt tttggtaaat atgattgttt   2340
ctttacttcc gaataagcaa tatataaaag tatctaaaaa cggaagtaac ttttgatgat   2400
cctaaaggtt ttgtaattga tacatgtcca aaaacctctt aatattcttt ctcacaaact   2460
gttgatggag ttaacaaagg gagacaaggt aattgggaca atatcaacgt tagatacagg   2520
acaagtgaaa aatgtggggt tgatgtcttc agctgcagca tatcaccgtt ggtatatatt   2580
gtcaattatt agtcctatgg atttgaaacg tgttttagta aataagagtg tccaagtggg   2640
acatttccaa taacgtatca cagctcctag agcttttgct atgtttctct aggcctgggc   2700
cgcctagccc acattccaag caaggaaatg aatggagttg ggcatcaaaa ttttggaagc   2760
attttaaga caaattatct tttaagtttc cttttttaaa cataaactat attttaggct    2820
tttttaagat aaatattatt tggatttcct ttcactcata ttttggatt tcaacttaac    2880
aaaacatagg gcgtgtctat ttgactccac ctacccaccc tactggagtt cgatcccact   2940
aaatcgcgtt atcccgcata gtagggattg actatggatc ggactttgtc gatccaaaga   3000
tatctaagaa attcagaaaa gattgtataa aattcagaaa cgattttacg aaattcatga   3060
aaaatgagaa atacatgttt tttttaattt acgtcggcat taaaaacgtt ggaccggctc   3120
tgtgtttcac caagaaaatt gtttcagttt atgcatgatc ttcaacttcc atattcttgt   3180
tttcaattct ggaaatccct aacagatcgg agctctcctc attcagtgag ttggaagatt   3240
gcatgattat ataattactc ttcacatcca catatattac attatattcc cctataattt   3300
catacaaccc tagaaaagaa tcttcaagta atctaatcgt gtcgatgact ccactcattt   3360
gctagaaaag aaaaaacaaa cagacttcat ttagctgaaa acaatctttt attcaacatt   3420
acaaagcact gatcaaagaa cctctaacat ggtaatatat ctatgacatt ttacgtatcc   3480
taaaagaaaa caaaaagtga tgtattggat gatgttttt ttttttactt tctagtttct    3540
tattacaacg acaaaaagag tccacgtcgt cacgcacttt tccggtggtg aaaaaaatgt   3600
ccaaatggat taaatctata atatctccag agagatcctc tccttctatc tttggggct    3660
ccactttttcc tatctctttt tgcccctttc ctctctctgt tcacaagtca tcttcttcct   3720
tcctctgaat cttgttcctt tttgctctct ctacttgatt cacccactct gtttctcgat   3780
tagtacgttg aaaactcact ttggttttgt ttgattcctc tttagtctgt ttttcgattt   3840
cgttttctct gattggtttg gtggtgagat ctctatcgta gtttgtccct tgggttaaga   3900
tatttcattt gattggtggg tttgttttat tgaagcttat tgttgtgaaa gttggagtct   3960
ttctcagttt ttaggttgaa ttattaagag aaagggaaga ttttggtgt gaagttaggt    4020
tatttgggt ttgagaagtt tgcaagtgaa aaaggttgtg aattgtgagt g             4071
```

<210> SEQ ID NO 6
<211> LENGTH: 24

```
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 6
tgaaaactca ctttggtttt gttt                                            24

<210> SEQ ID NO 7
<211> LENGTH: 25
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 7
aagacaaatt aacacatata aatga                                           25

<210> SEQ ID NO 8
<211> LENGTH: 24
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 8
atgaatagag ggaaagatga ggag                                            24

<210> SEQ ID NO 9
<211> LENGTH: 25
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 9
ttaaggctta gaggagtcat agcgt                                           25

<210> SEQ ID NO 10
<211> LENGTH: 22
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 10
agtaagagag ggaaagatga gg                                              22

<210> SEQ ID NO 11
<211> LENGTH: 20
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 11
gccaccatct cggtataacc                                                 20

<210> SEQ ID NO 12
<211> LENGTH: 1960
<212> TYPE: DNA
```

```
<213> ORGANISM: Cardamine oligosperma
<220> FEATURE:
<221> NAME/KEY: CDS
<222> LOCATION: (1)..(1959)

<400> SEQUENCE: 12 atg aag aga ggg aaa gat gat gag aag ata ctg gaa cct atg ttt cct        48
Met Lys Arg Gly Lys Asp Asp Glu Lys Ile Leu Glu Pro Met Phe Pro
1               5                   10                  15 aga ctt cat gtg aat gat gca gat aaa gga gga cct aga gct cct cct        96
Arg Leu His Val Asn Asp Ala Asp Lys Gly Gly Pro Arg Ala Pro Pro
            20                  25                  30 aga aac aag atg gct ctt tat gag cag ctt agt atc cct tct cag agg       144
Arg Asn Lys Met Ala Leu Tyr Glu Gln Leu Ser Ile Pro Ser Gln Arg
        35                  40                  45 ttt ggt gat cat gga aat ttg tct ctg agt tct cgt agt aac aac aca       192
Phe Gly Asp His Gly Asn Leu Ser Leu Ser Ser Arg Ser Asn Asn Thr
    50                  55                  60 agt act ttg gtt cac cct gga cca tct aat cag cag tct tgt ggt gtg       240
Ser Thr Leu Val His Pro Gly Pro Ser Asn Gln Gln Ser Cys Gly Val
65                  70                  75                  80 gaa cga aac tta tct gtc cag cat ctt gat tct tca gct gca gtc cat       288
Glu Arg Asn Leu Ser Val Gln His Leu Asp Ser Ser Ala Ala Val His
                85                  90                  95 gta act gag aat ttt gtc tcc caa atg ccc ttc atg gaa aat atg aga       336
Val Thr Glu Asn Phe Val Ser Gln Met Pro Phe Met Glu Asn Met Arg
            100                 105                 110 tct ttg gca aag cat gat cag agg aaa aca gta aga gag gaa gat gac       384
Ser Leu Ala Lys His Asp Gln Arg Lys Thr Val Arg Glu Glu Asp Asp
        115                 120                 125 ttt gca gtt cca gtg ttt gtt aac tca aga aga ttc cag agt cat ggt       432
Phe Ala Val Pro Val Phe Val Asn Ser Arg Arg Phe Gln Ser His Gly
    130                 135                 140 agt acc aag agt ggg att gtg att gaa aaa cac acg aca ttg gct act       480
Ser Thr Lys Ser Gly Ile Val Ile Glu Lys His Thr Thr Leu Ala Thr
145                 150                 155                 160 tgt tca aaa ctt gtt aga gat aag gtg aag atg aac gca aag tca ggt       528
Cys Ser Lys Leu Val Arg Asp Lys Val Lys Met Asn Ala Lys Ser Gly
                165                 170                 175 ggc ttt ata gat tta tca tca aca gag gaa gtg gat ctc gaa aaa tca       576
Gly Phe Ile Asp Leu Ser Ser Thr Glu Glu Val Asp Leu Glu Lys Ser
            180                 185                 190 gca tca agt tat gac aga gta aat gat tgt aat tct tcc ttg aga caa       624
Ala Ser Ser Tyr Asp Arg Val Asn Asp Cys Asn Ser Ser Leu Arg Gln
        195                 200                 205 gag tct aga aat aag tta tac cga gat ggt ggc gaa gct cat atg aag       672
Glu Ser Arg Asn Lys Leu Tyr Arg Asp Gly Gly Glu Ala His Met Lys
    210                 215                 220 gac act gct aat aga gtt gaa tct cac ttg gta acg gaa agt cat tct       720
Asp Thr Ala Asn Arg Val Glu Ser His Leu Val Thr Glu Ser His Ser
225                 230                 235                 240 gag gag ggt cat ggc agt cct gat gat gat gac aac ggt cat gaa tac       768
Glu Glu Gly His Gly Ser Pro Asp Asp Asp Asp Asn Gly His Glu Tyr
                245                 250                 255 tgc aga agc aga gga ggc gtc tct cta cag cag ata aat gaa gag gca       816
Cys Arg Ser Arg Gly Gly Val Ser Leu Gln Gln Ile Asn Glu Glu Ala
            260                 265                 270 agt gat gac gtt tct gat aat tcg atg gtg gat tct ata tcc agc ata       864
Ser Asp Asp Val Ser Asp Asn Ser Met Val Asp Ser Ile Ser Ser Ile
        275                 280                 285
```

-continued

| | | |
|---|---|---|
| gat gtt tct cct gat gat gtt gtg gga gca tta ggt caa aaa cgt ttc<br>Asp Val Ser Pro Asp Asp Val Val Gly Ala Leu Gly Gln Lys Arg Phe<br>290                         295                         300 | 912 |
| tgg agg gca agg aag gct att acc aat caa caa aga gta ttt gct gtt<br>Trp Arg Ala Arg Lys Ala Ile Thr Asn Gln Gln Arg Val Phe Ala Val<br>305                       310                     315                   320 | 960 |
| caa cta ttt gag ttg cac aga ctg att aag gtt caa aga ctt att gct<br>Gln Leu Phe Glu Leu His Arg Leu Ile Lys Val Gln Arg Leu Ile Ala<br>                  325                     330                   335 | 1008 |
| gca tca ccg gat atc gtg ctc gac gaa atc aat tac ctt gga aaa gtt<br>Ala Ser Pro Asp Ile Val Leu Asp Glu Ile Asn Tyr Leu Gly Lys Val<br>                340                     345                   350 | 1056 |
| tct gct aaa agc tat cca gtg aag aag ctc gtt cca tca gaa ttt atc<br>Ser Ala Lys Ser Tyr Pro Val Lys Lys Leu Val Pro Ser Glu Phe Ile<br>355                       360                     365 | 1104 |
| gta aag cct cct cta cca caa gtt gtc gtc aac aaa cag cac agg agc<br>Val Lys Pro Pro Leu Pro Gln Val Val Val Asn Lys Gln His Arg Ser<br>370                       375                     380 | 1152 |
| gac tcc gaa aag act gac caa cat aaa atg gaa tgc tca gct gag aat<br>Asp Ser Glu Lys Thr Asp Gln His Lys Met Glu Cys Ser Ala Glu Asn<br>385                       390                    395                400 | 1200 |
| gtt gtt ggt agg ttg tca aac caa gga cat cat cat aat cat caa cct<br>Val Val Gly Arg Leu Ser Asn Gln Gly His His His Asn His Gln Pro<br>                  405                     410                   415 | 1248 |
| tcc aac tac atg cct ttt cca agc aac cca ccc gct tca cca gct gta<br>Ser Asn Tyr Met Pro Phe Pro Ser Asn Pro Pro Ala Ser Pro Ala Val<br>                  420                     425                   430 | 1296 |
| aac gga tgt tgc tat cct cct cag cct cct cct tca gga aac cag caa<br>Asn Gly Cys Cys Tyr Pro Pro Gln Pro Pro Pro Ser Gly Asn Gln Gln<br>                435                     440                   445 | 1344 |
| tgg tta atc cct gtt atg tct cct tct gaa gga ctt ata tac aag cct<br>Trp Leu Ile Pro Val Met Ser Pro Ser Glu Gly Leu Ile Tyr Lys Pro<br>450                       455                     460 | 1392 |
| cat cct ggt atg gga cac acg ggg cac tac gga gga tat tat ggt cat<br>His Pro Gly Met Gly His Thr Gly His Tyr Gly Gly Tyr Tyr Gly His<br>465                       470                     475                  480 | 1440 |
| ttt atg cct ccg ccg atg gta atg cct ccg ttt cat ccg ggc atg gga<br>Phe Met Pro Pro Pro Met Val Met Pro Pro Phe His Pro Gly Met Gly<br>                  485                     490                   495 | 1488 |
| ttc cca cct cct ggt aat ggc tac ttc cct cct tat ggt gta atc cca<br>Phe Pro Pro Pro Gly Asn Gly Tyr Phe Pro Pro Tyr Gly Val Ile Pro<br>                  500                     505                   510 | 1536 |
| gcc atg atg aac cct tat ggt cca ggc caa caa caa caa caa caa cca<br>Ala Met Met Asn Pro Tyr Gly Pro Gly Gln Gln Gln Gln Gln Gln Pro<br>515                       520                     525 | 1584 |
| caa gcc aat gaa caa acg aat cag ttt ggg tat tct ggg aat ctt cag<br>Gln Ala Asn Glu Gln Thr Asn Gln Phe Gly Tyr Ser Gly Asn Leu Gln<br>530                       535                     540 | 1632 |
| aac aac acc cat caa gaa agc tcc gtt aat gaa gct gct cct cca cag<br>Asn Asn Thr His Gln Glu Ser Ser Val Asn Glu Ala Ala Pro Pro Gln<br>545                       550                     555                560 | 1680 |
| gaa cca cta aca aag tct tat ccg cgg gct aga aag agc agg caa gtg<br>Glu Pro Leu Thr Lys Ser Tyr Pro Arg Ala Arg Lys Ser Arg Gln Val<br>                      565                     570                   575 | 1728 |
| agc aca gca agc agt gca agt ggg cga gag gga atc tcc ggt agc act<br>Ser Thr Ala Ser Ser Ala Ser Gly Arg Glu Gly Ile Ser Gly Ser Thr<br>                  580                     585                   590 | 1776 |
| tcc ttt cgt cca ttc tca gcc gtt gat gag gat aac aac gat aac aac<br>Ser Phe Arg Pro Phe Ser Ala Val Asp Glu Asp Asn Asn Asp Asn Asn<br>                595                     600                   605 | 1824 |

-continued

```
aac gac gca cct gat caa atg atg aca acc acc acg acc acg aca aga    1872
Asn Asp Ala Pro Asp Gln Met Met Thr Thr Thr Thr Thr Thr Thr Arg
610                 615                 620 aca act gtt act cag aca aca aga gat gga gga gaa gtg acg aga gtg    1920
Thr Thr Val Thr Gln Thr Thr Arg Asp Gly Gly Glu Val Thr Arg Val
625                 630                 635                 640 ata aag ggg ttc ctc aca atg cga agc tcg cta gtg aga a              1960
Ile Lys Gly Phe Leu Thr Met Arg Ser Ser Leu Val Arg
                645                 650

<210> SEQ ID NO 13
<211> LENGTH: 653
<212> TYPE: PRT
<213> ORGANISM: Cardamine oligosperma

<400> SEQUENCE: 13

Met Lys Arg Gly Lys Asp Asp Glu Lys Ile Leu Glu Pro Met Phe Pro
1               5                   10                  15

Arg Leu His Val Asn Asp Ala Asp Lys Gly Gly Pro Arg Ala Pro Pro
            20                  25                  30

Arg Asn Lys Met Ala Leu Tyr Glu Gln Leu Ser Ile Pro Ser Gln Arg
        35                  40                  45

Phe Gly Asp His Gly Asn Leu Ser Leu Ser Ser Arg Ser Asn Asn Thr
    50                  55                  60

Ser Thr Leu Val His Pro Gly Pro Ser Asn Gln Gln Ser Cys Gly Val
65                  70                  75                  80

Glu Arg Asn Leu Ser Val Gln His Leu Asp Ser Ser Ala Ala Val His
                85                  90                  95

Val Thr Glu Asn Phe Val Ser Gln Met Pro Phe Met Glu Asn Met Arg
            100                 105                 110

Ser Leu Ala Lys His Asp Gln Arg Lys Thr Val Arg Glu Glu Asp Asp
        115                 120                 125

Phe Ala Val Pro Val Phe Val Asn Ser Arg Arg Phe Gln Ser His Gly
    130                 135                 140

Ser Thr Lys Ser Gly Ile Val Ile Glu Lys His Thr Thr Leu Ala Thr
145                 150                 155                 160

Cys Ser Lys Leu Val Arg Asp Lys Val Lys Met Asn Ala Lys Ser Gly
                165                 170                 175

Gly Phe Ile Asp Leu Ser Ser Thr Glu Glu Val Asp Leu Glu Lys Ser
            180                 185                 190

Ala Ser Ser Tyr Asp Arg Val Asn Asp Cys Asn Ser Ser Leu Arg Gln
        195                 200                 205

Glu Ser Arg Asn Lys Leu Tyr Arg Asp Gly Gly Glu Ala His Met Lys
    210                 215                 220

Asp Thr Ala Asn Arg Val Glu Ser His Leu Val Thr Glu Ser His Ser
225                 230                 235                 240

Glu Glu Gly His Gly Ser Pro Asp Asp Asp Asn Gly His Glu Tyr
                245                 250                 255

Cys Arg Ser Arg Gly Gly Val Ser Leu Gln Gln Ile Asn Glu Glu Ala
            260                 265                 270

Ser Asp Asp Val Ser Asp Asn Ser Met Val Asp Ser Ile Ser Ser Ile
        275                 280                 285

Asp Val Ser Pro Asp Val Val Gly Ala Leu Gly Gln Lys Arg Phe
    290                 295                 300
```

```
Trp Arg Ala Arg Lys Ala Ile Thr Asn Gln Gln Arg Val Phe Ala Val
305                 310                 315                 320

Gln Leu Phe Glu Leu His Arg Leu Ile Lys Val Gln Arg Leu Ile Ala
            325                 330                 335

Ala Ser Pro Asp Ile Val Leu Asp Glu Ile Asn Tyr Leu Gly Lys Val
            340                 345                 350

Ser Ala Lys Ser Tyr Pro Val Lys Lys Leu Val Pro Ser Glu Phe Ile
        355                 360                 365

Val Lys Pro Pro Leu Pro Gln Val Val Asn Lys Gln His Arg Ser
370                 375                 380

Asp Ser Glu Lys Thr Asp Gln His Lys Met Glu Cys Ser Ala Glu Asn
385                 390                 395                 400

Val Val Gly Arg Leu Ser Asn Gln Gly His His Asn His Gln Pro
            405                 410                 415

Ser Asn Tyr Met Pro Phe Pro Ser Asn Pro Ala Ser Pro Ala Val
            420                 425                 430

Asn Gly Cys Cys Tyr Pro Pro Gln Pro Pro Ser Gly Asn Gln Gln
            435                 440                 445

Trp Leu Ile Pro Val Met Ser Pro Ser Glu Gly Leu Ile Tyr Lys Pro
450                 455                 460

His Pro Gly Met Gly His Thr Gly His Tyr Gly Gly Tyr Tyr Gly His
465                 470                 475                 480

Phe Met Pro Pro Pro Met Val Met Pro Pro Phe His Pro Gly Met Gly
            485                 490                 495

Phe Pro Pro Pro Gly Asn Gly Tyr Phe Pro Pro Tyr Gly Val Ile Pro
            500                 505                 510

Ala Met Met Asn Pro Tyr Gly Pro Gly Gln Gln Gln Gln Gln Pro
            515                 520                 525

Gln Ala Asn Glu Gln Thr Asn Gln Phe Gly Tyr Ser Gly Asn Leu Gln
530                 535                 540

Asn Asn Thr His Gln Glu Ser Ser Val Asn Glu Ala Ala Pro Pro Gln
545                 550                 555                 560

Glu Pro Leu Thr Lys Ser Tyr Pro Arg Ala Arg Lys Ser Arg Gln Val
            565                 570                 575

Ser Thr Ala Ser Ser Ala Ser Gly Arg Glu Gly Ile Ser Gly Ser Thr
            580                 585                 590

Ser Phe Arg Pro Phe Ser Ala Val Asp Glu Asp Asn Asn Asp Asn Asn
            595                 600                 605

Asn Asp Ala Pro Asp Gln Met Met Thr Thr Thr Thr Thr Thr Arg
610                 615                 620

Thr Thr Val Thr Gln Thr Thr Arg Asp Gly Gly Glu Val Thr Arg Val
625                 630                 635                 640

Ile Lys Gly Phe Leu Thr Met Arg Ser Ser Leu Val Arg
            645                 650

<210> SEQ ID NO 14
<211> LENGTH: 3617
<212> TYPE: DNA
<213> ORGANISM: Cardamine oligosperma
<220> FEATURE:
<221> NAME/KEY: 5'UTR
<222> LOCATION: (1)..(306)
<220> FEATURE:
<221> NAME/KEY: exon
<222> LOCATION: (307)..(531)
<220> FEATURE:
```

-continued

```
<221> NAME/KEY: Intron
<222> LOCATION: (532)..(818)
<220> FEATURE:
<221> NAME/KEY: exon
<222> LOCATION: (819)..(1531)
<220> FEATURE:
<221> NAME/KEY: unsure
<222> LOCATION: (1404)..(1406)
<223> OTHER INFORMATION: encoded amino acid is unsure due to nucleotide
      uncertainty
<220> FEATURE:
<221> NAME/KEY: unsure
<222> LOCATION: (1406)..(1406)
<223> OTHER INFORMATION: K = g or t/u
<220> FEATURE:
<221> NAME/KEY: Unsure
<222> LOCATION: (1409)..(1412)
<223> OTHER INFORMATION: encoded amino acid is unsure due to nucleotide
      uncertainty
<220> FEATURE:
<221> NAME/KEY: unsure
<222> LOCATION: (1412)..(1412)
<223> OTHER INFORMATION: W = a or t/u
<220> FEATURE:
<221> NAME/KEY: unsure
<222> LOCATION: (1419)..(1419)
<223> OTHER INFORMATION: R = a or c
<220> FEATURE:
<221> NAME/KEY: unsure
<222> LOCATION: (1419)..(1421)
<223> OTHER INFORMATION: encoded amino acid is unsure due to nucleotide
      uncertainty
<220> FEATURE:
<221> NAME/KEY: Intron
<222> LOCATION: (1532)..(2509)
<220> FEATURE:
<221> NAME/KEY: exon
<222> LOCATION: (2510)..(2561)
<220> FEATURE:
<221> NAME/KEY: Intron
<222> LOCATION: (2562)..(2645)
<220> FEATURE:
<221> NAME/KEY: exon
<222> LOCATION: (2646)..(3615)
<223> OTHER INFORMATION: partial

<400> SEQUENCE: 14
tacttgattt accatctctc ttaatttatc agctcgtgga gctctcatat ccttcgtttg      60
atttcagttc actcggtttt aaaactttgt tttctctgat tggggagatc taccgtagtc     120
ggtggtcaat tagtgggttt tgttttgagt ttcatttgat ttgtgggttt agttttttga     180
agcttattgt tacgaaattt tgggtctttt tcaattttag gtcaaataat tggggaaaag     240
ttgagaaatc gtgtgaaatt aggttatttg ggttgagaaa ttttgaagca agtttgtga      300 gttgtg atg aag aga ggg aaa gat gat gag aag ata ctg gaa cct atg        348
       Met Lys Arg Gly Lys Asp Asp Glu Lys Ile Leu Glu Pro Met
       1               5                  10 ttt cct aga ctt cat gtg aat gat gca gat aaa gga gga cct aga gct      396
Phe Pro Arg Leu His Val Asn Asp Ala Asp Lys Gly Gly Pro Arg Ala
15                  20                  25                  30 cct cct aga aac aag atg gct ctt tat gag cag ctt agt atc cct tct      444
Pro Pro Arg Asn Lys Met Ala Leu Tyr Glu Gln Leu Ser Ile Pro Ser
                35                  40                  45 gag agg ttt ggt gat cat gga aat ttg tct ctg agt tct cgt agt aac      492
Glu Arg Phe Gly Asp His Gly Asn Leu Ser Leu Ser Ser Arg Ser Asn
            50                  55                  60 aac aca agt act ttg gtt cac cct gga cca tct aat cag gtatggagtt       541
Asn Thr Ser Thr Leu Val His Pro Gly Pro Ser Asn Gln
65                  70                  75
```

-continued

```
gtggaaattg atgttatata gcttgcaaga gagtagtagg agttgattgt tcaatgtttt    601
cagttgtttt ttagctcatt ttagcttctt ttgttcatgg attgaactca cttgtagata    661
tcggaatata gtggatgtat atctattcta gtgtggaaga tttttttatgt ttgaaagttt    721 tatggatgct tcttgtgatt ggcctgaaca ttctggttac tgtattcaac ttgataagga    781
cattggaaat aatcgttttt ggtgctcttt cctgcag cag tct tgt ggt gtg gaa    836
                                          Gln Ser Cys Gly Val Glu
                                                            80 cga aac tta tct gtc cag cat ctt gat tct tca gct gca gtc cat gta    884
Arg Asn Leu Ser Val Gln His Leu Asp Ser Ser Ala Ala Val His Val
            85                  90                  95 act gag aat ttt gtc tcc caa atg ccc ttc atg gaa aat atg aga tct    932
Thr Glu Asn Phe Val Ser Gln Met Pro Phe Met Glu Asn Met Arg Ser
100                 105                 110 ttg gca aag cat gat cag agg aaa aca gta aga gag gaa gat gac ttt    980
Leu Ala Lys His Asp Gln Arg Lys Thr Val Arg Glu Glu Asp Asp Phe
        115                 120                 125 gca gtt cca gtg ttt gtt aac tca aga aga ttc cag agt cat ggt agt    1028
Ala Val Pro Val Phe Val Asn Ser Arg Arg Phe Gln Ser His Gly Ser
130                 135                 140                 145 acc aag agt ggg att gtg att gaa aaa cac acg aca ttg gct act tgt    1076
Thr Lys Ser Gly Ile Val Ile Glu Lys His Thr Thr Leu Ala Thr Cys
                150                 155                 160 tca aaa ctt gtt aga gat aag gtg aag atg aac gca aag tca ggt ggc    1124
Ser Lys Leu Val Arg Asp Lys Val Lys Met Asn Ala Lys Ser Gly Gly
            165                 170                 175 ttt ata gat tta tca tca aca gag gaa gtg gat ctc gaa aaa tca gca    1172
Phe Ile Asp Leu Ser Ser Thr Glu Glu Val Asp Leu Glu Lys Ser Ala
        180                 185                 190 tca agt tat gac aga gta aat gat tgt aat tct tcc ttg aga caa gag    1220
Ser Ser Tyr Asp Arg Val Asn Asp Cys Asn Ser Ser Leu Arg Gln Glu
195                 200                 205 tct aga aat aag tta tac cga gat ggt ggc gaa gct cat atg aag gac    1268
Ser Arg Asn Lys Leu Tyr Arg Asp Gly Gly Glu Ala His Met Lys Asp
210                 215                 220                 225 act gct aat aga gtt gaa tct cac ttg gta acg gaa agt cat tct gag    1316
Thr Ala Asn Arg Val Glu Ser His Leu Val Thr Glu Ser His Ser Glu
                230                 235                 240 gag ggt cat ggc agt cct gat gat gat gac aac ggt cat gaa tac tgc    1364
Glu Gly His Gly Ser Pro Asp Asp Asp Asp Asn Gly His Glu Tyr Cys
            245                 250                 255 aga agc aga gga ggc gtc tct cta cag cag ata aat gaa gak gca agw    1412
Arg Ser Arg Gly Gly Val Ser Leu Gln Gln Ile Asn Glu Xaa Ala Xaa
        260                 265                 270 gat gac rtt tct gat aat tcg atg gtg gat tct ata tcc agc ata gat    1460
Asp Asp Xaa Ser Asp Asn Ser Met Val Asp Ser Ile Ser Ser Ile Asp
275                 280                 285 gtt tct cct gat gat gtt gtg gga gca tta ggt caa aaa cgt ttc tgg    1508
Val Ser Pro Asp Asp Val Val Gly Ala Leu Gly Gln Lys Arg Phe Trp
                290                 295                 300                 305 agg gca agg aag gct att acc aa gtaagttcac tagttttttt ttacggttta    1561
Arg Ala Arg Lys Ala Ile Thr Asn
            310 gttaactttg ttatttattt tccgctcttt ctatccatct ctttctttga taccgacttt    1621 gctacttgca agaagttaat gctgaagcat agttacctaa ttagactgaa gctttcctct    1681 gctgtttttt ggacactttc ttttagtttc tttgctttttc catgcatact gatacaatgg    1741
```

-continued

```
atatataact cggtttatat tgtgtctcaa tttgggagaa acgatttcgg gttttttggct      1801 tgagacatga tggtactata gtggagaagc cccccttga ttcctcgtaa aatggtcctg        1861
ttatatgtta gttgacgagc cctcggtagc atattaacgc gttggatcat gttatagcag      1921
ggagggacat tctctgttga cgtacattgt acaaggtgcc cgccgagaca gttcatggct      1981
ttatactctt gtcttctttg catctgcttg ttggaacatg tccctgtctc ggtttggtat      2041
tgcttttatt ctgcactttc gtcttgggca ttttccttc ttgtcattca aggggttgaa       2101
ccaggtaggg gaacttgttt tcgaggaccc tgggatctaa attttagtta accgtacata      2161
gaacctagtt atgagtctta tgacagtgca gaattatagt tgcttttgc tactgcttaa       2221 taggatcctt agagtggttg tgaactacgg ttttttctat ggattttaga ctctaggtgt      2281
tcttatcgct acgataaggt atcacgatac atgaccaact catataacaa gcttttctca     2341
gcttttcgtt gagggtaagc tagaaatcta ttaacccatc ctttgcttaa cccattcttg     2401
catttaattt cttttttgtgt tattgcttct gttttccctt cgtatttctt cattttacta   2461
ttcgattagc tggtcatatt ccttatgaaa ttccgtttct cattacag t caa caa        2516
                                                        Gln Gln
                                                           315 aga gta ttt gct gtt caa cta ttt gag ttg cac aga ctg att aag             2561
Arg Val Phe Ala Val Gln Leu Phe Glu Leu His Arg Leu Ile Lys
        320                 325                 330 gtaaagtaat tcagaaaact tctcctataa atatttttgc tgaaacaaac gtcttcatct      2621
gtgctttgtt tctgtaatac tcag gtt caa aga ctt att gct gca tca ccg         2672
                          Val Gln Arg Leu Ile Ala Ala Ser Pro
                                              335 gat atc gtg ctc gac gaa atc aat tac ctt gga aaa gtt tct gct aaa        2720
Asp Ile Val Leu Asp Glu Ile Asn Tyr Leu Gly Lys Val Ser Ala Lys
340                 345                 350                 355 agc tat cca gtg aag aag ctc gtt cca tca gaa ttt atc gta aag cct        2768
Ser Tyr Pro Val Lys Lys Leu Val Pro Ser Glu Phe Ile Val Lys Pro
            360                 365                 370 cct cta cca caa gtt gtc gtc aac aaa cag cac agg agc gac tcc gaa        2816
Pro Leu Pro Gln Val Val Val Asn Lys Gln His Arg Ser Asp Ser Glu
        375                 380                 385 aag act gac caa cat aaa atg gaa tgc tca gct gag aat gtt gtt ggt        2864
Lys Thr Asp Gln His Lys Met Glu Cys Ser Ala Glu Asn Val Val Gly
        390                 395                 400 agg ttg tca aac caa gga cat cat cat aat cat caa cct tcc aac tac        2912
Arg Leu Ser Asn Gln Gly His His His Asn His Gln Pro Ser Asn Tyr
    405                 410                 415 atg cct ttt cca agc aac cca ccc gct tca cca gct gta aac gga tgt        2960
Met Pro Phe Pro Ser Asn Pro Pro Ala Ser Pro Ala Val Asn Gly Cys
420                 425                 430                 435 tgc tat cct cct cag cct cct cct tca gga aac cag caa tgg tta atc        3008
Cys Tyr Pro Pro Gln Pro Pro Pro Ser Gly Asn Gln Gln Trp Leu Ile
            440                 445                 450 cct gtt atg tct cct tct gaa gga ctt ata tac aag cct cat cct ggt        3056
Pro Val Met Ser Pro Ser Glu Gly Leu Ile Tyr Lys Pro His Pro Gly
        455                 460                 465 atg gga cac acg ggg cac tac gga gga tat tat ggt cat ttt atg cct        3104
Met Gly His Thr Gly His Tyr Gly Gly Tyr Tyr Gly His Phe Met Pro
        470                 475                 480 ccg ccg atg gta atg cct ccg ttt cat ccg ggc atg gga ttc cca cct        3152
Pro Pro Met Val Met Pro Pro Phe His Pro Gly Met Gly Phe Pro Pro
    485                 490                 495
```

```
cct ggt aat ggc tac ttc cct cct tat ggt gta atc cca gcc atg atg      3200
Pro Gly Asn Gly Tyr Phe Pro Pro Tyr Gly Val Ile Pro Ala Met Met
500                 505                 510                 515 aac cct tat ggt cca ggc caa caa caa caa caa cca caa gcc aat          3248
Asn Pro Tyr Gly Pro Gly Gln Gln Gln Gln Gln Pro Gln Ala Asn
            520                 525                 530 gaa caa acg aat cag ttt ggg tat tct ggg aat ctt cag aac aac acc      3296
Glu Gln Thr Asn Gln Phe Gly Tyr Ser Gly Asn Leu Gln Asn Asn Thr
            535                 540                 545 cat caa gaa agc tcc gtt aat gaa gct gct cct cca cag gaa cca cta      3344
His Gln Glu Ser Ser Val Asn Glu Ala Ala Pro Pro Gln Glu Pro Leu
        550                 555                 560 aca aag tct tat ccg cgg gct aga aag agc agg caa gtg agc aca gca      3392
Thr Lys Ser Tyr Pro Arg Ala Arg Lys Ser Arg Gln Val Ser Thr Ala
        565                 570                 575 agc agt gca agt ggg cga gag gga atc tcc ggt agc act tcc ttt cgt      3440
Ser Ser Ala Ser Gly Arg Glu Gly Ile Ser Gly Ser Thr Ser Phe Arg
580                 585                 590                 595 cca ttc tca gcc gtt gat gag gat aac aac gat aac aac aac gac gca      3488
Pro Phe Ser Ala Val Asp Glu Asp Asn Asn Asp Asn Asn Asn Asp Ala
                600                 605                 610 cct gat caa atg atg aca acc acc acg acc acg aca aga aca act gtt      3536
Pro Asp Gln Met Met Thr Thr Thr Thr Thr Thr Arg Thr Thr Val
            615                 620                 625 act cag aca aca aga gat gga gga gaa gtg acg aga gtg ata aag gtg      3584
Thr Gln Thr Thr Arg Asp Gly Gly Glu Val Thr Arg Val Ile Lys Val
            630                 635                 640 gtt cct cac aat gcg aag ctc gct agt gag a at                         3617
Val Pro His Asn Ala Lys Leu Ala Ser Glu
        645                 650

<210> SEQ ID NO 15
<211> LENGTH: 430
<212> TYPE: DNA
<213> ORGANISM: Pisum sativum
<220> FEATURE:
<221> NAME/KEY: exon
<222> LOCATION: (2)..(13)
<223> OTHER INFORMATION: partial
<220> FEATURE:
<221> NAME/KEY: Intron
<222> LOCATION: (14)..(94)
<223> OTHER INFORMATION: partial
<220> FEATURE:
<221> NAME/KEY: exon
<222> LOCATION: (95)..(430)
<223> OTHER INFORMATION: partial

<400> SEQUENCE: 15 t aga ctg ata aag gtaaattatc tttgacattg atcagtgctc tcacacaccc        53
  Arg Leu Ile Lys
  1 ttgagtctta ctgtaatgat taattctttt tacttaagca g gtc caa caa cta att   109
                                              Val Gln Gln Leu Ile
                                                              5 gcc gga tcg cca gat ctt ttg ttt gat gat ggt gct ttt ctg gga aag     157
Ala Gly Ser Pro Asp Leu Leu Phe Asp Asp Gly Ala Phe Leu Gly Lys
10              15                  20                  25 tct ctt cca gat gga tct act cct aaa aaa ctc tca ttg gaa tat gtt     205
Ser Leu Pro Asp Gly Ser Thr Pro Lys Lys Leu Ser Leu Glu Tyr Val
            30                  35                  40
```

-continued

```
gta aaa gct cgg cta caa aat ctt aag cgc aaa gtt gat tct gaa aag    253
Val Lys Ala Arg Leu Gln Asn Leu Lys Arg Lys Val Asp Ser Glu Lys
         45                  50                  55 ata aat caa aac atg gaa tgt tct gca gag aat gct gtt ggt aaa aca    301
Ile Asn Gln Asn Met Glu Cys Ser Ala Glu Asn Ala Val Gly Lys Thr
         60                  65                  70 tct att tcg tcc gtg aaa aat acg agc cac ctt tct agt tcc atg cct    349
Ser Ile Ser Ser Val Lys Asn Thr Ser His Leu Ser Ser Ser Met Pro
     75                  80                  85 ttt gcc gga aat cca cac caa gga aat gtg gca gct gat aat ggg atg    397
Phe Ala Gly Asn Pro His Gln Gly Asn Val Ala Ala Asp Asn Gly Met
 90                  95                 100                 105 ggt ccc tgg tgt ttc aat cag tca cct ggg cat                        430
Gly Pro Trp Cys Phe Asn Gln Ser Pro Gly His
                 110                 115
```

<210> SEQ ID NO 16
<211> LENGTH: 116
<212> TYPE: PRT
<213> ORGANISM: Pisum sativum

<400> SEQUENCE: 16

Arg Leu Ile Lys Val Gln Gln Leu Ile Ala Gly Ser Pro Asp Leu Leu
1               5                   10                  15

Phe Asp Asp Gly Ala Phe Leu Gly Lys Ser Leu Pro Asp Gly Ser Thr
             20                  25                  30

Pro Lys Lys Leu Ser Leu Glu Tyr Val Val Lys Ala Arg Leu Gln Asn
         35                  40                  45

Leu Lys Arg Lys Val Asp Ser Glu Lys Ile Asn Gln Asn Met Glu Cys
 50                  55                  60

Ser Ala Glu Asn Ala Val Gly Lys Thr Ser Ile Ser Ser Val Lys Asn
65                  70                  75                  80

Thr Ser His Leu Ser Ser Ser Met Pro Phe Ala Gly Asn Pro His Gln
             85                  90                  95

Gly Asn Val Ala Ala Asp Asn Gly Met Gly Pro Trp Cys Phe Asn Gln
            100                 105                 110

Ser Pro Gly His
        115

<210> SEQ ID NO 17
<211> LENGTH: 74
<212> TYPE: PRT
<213> ORGANISM: Broccoli/Cauliflower

<400> SEQUENCE: 17

Arg Leu Ile Met Val Gln Lys Met Val Ala Lys Ser Pro Asn Leu Val
1               5                   10                  15

Leu Lys Asn Lys Ile Asn Gly Gly Ser Lys Phe Lys Lys Pro Asn Thr
             20                  25                  30

Glu Asn Gln Lys Pro Val Thr Glu Ala Tyr Pro Glu His Met Lys Pro
         35                  40                  45

Lys Ile Pro Leu Pro Phe Ile Ser Lys Glu Leu Met Thr Pro Ile Trp
     50                  55                  60

Gln Gln Gln Leu Leu Pro Pro Gln Glu Asn
65                   70

<210> SEQ ID NO 18
<211> LENGTH: 555

```
<212> TYPE: DNA
<213> ORGANISM: Glycine max

<400> SEQUENCE: 18
acgcgtccga gcacctctca gtgctacttt catgaatccc gcctatcaat tcccagcttc      60
tcatccagta gttggggttt caccgtttgt ccctccggcc agtcacacct acttcgctcc     120
ctttggcatg ccggtaatga atcaagcaac atcaggatca gccgttgaac aggtgaacca     180
gtttgctgca caaggttctc atggtcaaaa tggtcattca tctgtagagg gagccgattt     240
taacactcat cataaccaaa gctcatctaa cttgccagtt cagaagaatg gagctaggtt     300
acatgttaaa aaatctcagg ccctgaagga gagagggtta caagggagca caagaagcag     360
tcctagtgaa atggcacagg gaatcagagc acggaaaatt gctgacgaa gtgatgcacg     420 tctctttctc ttcacgctga tgaaaccaga cagcaaacac aagccatcaa agttgtaccc     480
cataaccgga aatccgcgac ggaatcagca gctagaattg ttcaatccat tcaagaagag     540
agaaaacagc atgat                                                    555

<210> SEQ ID NO 19
<211> LENGTH: 185
<212> TYPE: PRT
<213> ORGANISM: Glycine max

<400> SEQUENCE: 19

Arg Val Arg Ala Pro Leu Ser Ala Thr Phe Met Asn Pro Ala Tyr Gln
1               5                   10                  15

Phe Pro Ala Ser His Pro Val Val Gly Val Ser Pro Phe Val Pro Pro
                20                  25                  30

Ala Ser His Thr Tyr Phe Ala Pro Phe Gly Met Pro Val Met Asn Gln
            35                  40                  45

Ala Thr Ser Gly Ser Ala Val Glu Gln Val Asn Gln Phe Ala Ala Gln
        50                  55                  60

Gly Ser His Gly Gln Asn Gly His Ser Ser Val Glu Gly Ala Asp Phe
65                  70                  75                  80

Asn Thr His His Asn Gln Ser Ser Ser Asn Leu Pro Val Gln Lys Asn
                85                  90                  95

Gly Ala Arg Leu His Val Lys Lys Ser Gln Ala Leu Lys Glu Arg Gly
            100                 105                 110

Leu Gln Gly Ser Thr Arg Ser Ser Pro Ser Glu Met Ala Gln Gly Ile
        115                 120                 125

Arg Ala Arg Lys Ile Ala Asp Gly Ser Asp Ala Gln Ser Leu Ser Leu
    130                 135                 140

His Ala Asp Glu Thr Arg Gln Gln Thr Gln Ala Ile Lys Val Val Pro
145                 150                 155                 160

His Asn Arg Lys Ser Ala Thr Glu Ser Ala Ala Arg Ile Val Gln Ser
                165                 170                 175

Ile Gln Glu Glu Arg Lys Gln His Asp
            180                 185

<210> SEQ ID NO 20
<211> LENGTH: 577
<212> TYPE: DNA
<213> ORGANISM: Lycopersicon esculentum

<400> SEQUENCE: 20
tccattttca cacagtcgtt tgatcttttg ccgactcttc ccttgttttt ttttctcaac      60
```

-continued

```
tgtaatctct ttcttcatat tattgtgctt accaacaagg cctgttacat gatcacagaa      120
aaatataata gtaattttgt gaaattatac atcttttttg cttctgtgtg cttcagaaat      180
ctcttgattt ctatgtaaag attgtgtttt gggtatttgg gtcggtagaa ttcttgtttt      240
tttaggtggg gtttgcttgg ttttcttcaa ttttgattgg ttttgttgaa aagttcagaa      300
atttgatgta attgtacgga tttctttgaa ttttggaagt tgaatgtatg gtaaagtttc      360 gttttttgg tttaatttaa tgaatgttgg agattgggtg aacctgttga gaagctatta      420
aagggaagaa atgaagagag gaaagggtga agagaagttg atgggaccta tgtttccaag      480
gcttcatgtt aatgatacag aaaagggagg tccaaaagca cctccaagaa acaaaatggc      540
tctttatgag cagctcagta ttccttctca gagattc                              577
```

```
<210> SEQ ID NO 21
<211> LENGTH: 582
<212> TYPE: DNA
<213> ORGANISM: Lycopersicon esculentum
<220> FEATURE:
<221> NAME/KEY: 5'UTR
<222> LOCATION: (1)..(43)
<220> FEATURE:
<221> NAME/KEY: exon
<222> LOCATION: (44)..(582)

<400> SEQUENCE: 21
```

```
attattcgtg agttttggag gctaactact gaggtagagg aag atg aaa aga ggt        55
                                             Met Lys Arg Gly
                                              1 aca ggt gaa gag aaa gtt atg ggg cct atg ttt cca agg ctt aat gtt      103
Thr Gly Glu Glu Lys Val Met Gly Pro Met Phe Pro Arg Leu Asn Val
 5              10                  15                  20 aat gat aca gaa aaa gga ggt cca aga gca cct cca agg aac aag atg      151
Asn Asp Thr Glu Lys Gly Gly Pro Arg Ala Pro Pro Arg Asn Lys Met
             25                  30                  35 gct ctt tat gaa caa ctg agt atc cct tcc caa cga tac aac cct ggt      199
Ala Leu Tyr Glu Gln Leu Ser Ile Pro Ser Gln Arg Tyr Asn Pro Gly
         40                  45                  50 gat ttg cct cat aac agt agt aac agt gca aat ttg gtc ctt cct cac      247
Asp Leu Pro His Asn Ser Ser Asn Ser Ala Asn Leu Val Leu Pro His
     55                  60                  65 cca agc cag gag aat gaa cac gaa aga ggt gta tta ttc tct aga caa      295
Pro Ser Gln Glu Asn Glu His Glu Arg Gly Val Leu Phe Ser Arg Gln
 70                  75                  80 ctt cct gca tta aga cat cca gtt gaa aag cca tat gga cgt agt tct      343
Leu Pro Ala Leu Arg His Pro Val Glu Lys Pro Tyr Gly Arg Ser Ser
85                  90                  95                 100 ggt tca aat act cca ttg cgg gaa gtt aag tct aaa agg cag aca gaa      391
Gly Ser Asn Thr Pro Leu Arg Glu Val Lys Ser Lys Arg Gln Thr Glu
                105                 110                 115 aag gaa gat ttt aga gtt ccc act ttt gat aac tcc aag gag cgt gca      439
Lys Glu Asp Phe Arg Val Pro Thr Phe Asp Asn Ser Lys Glu Arg Ala
                120                 125                 130 gta aac aca gag gac tat tct aaa ggt acc tca gat ata gat aag cga      487
Val Asn Thr Glu Asp Tyr Ser Lys Gly Thr Ser Asp Ile Asp Lys Arg
            135                 140                 145 gac agt act ttg aag cgg act gat caa ctc tcc cat gtc aca ccg aga      535
Asp Ser Thr Leu Lys Arg Thr Asp Gln Leu Ser His Val Thr Pro Arg
        150                 155                 160 gag aat ctt gtt aat acc ttt ggt gaa tca cat aag acc aat ata gt       582
Glu Asn Leu Val Asn Thr Phe Gly Glu Ser His Lys Thr Asn Ile
165                 170                 175
```

<210> SEQ ID NO 22
<211> LENGTH: 1347
<212> TYPE: DNA
<213> ORGANISM: Lycopersicon esculentum
<220> FEATURE:
<221> NAME/KEY: exon
<222> LOCATION: (2)..(1171)
<220> FEATURE:
<221> NAME/KEY: 3'UTR
<222> LOCATION: (1172)..(1347)

<400> SEQUENCE: 22

```
t ttg gac cga ggt gac gac tta tct gag act tcc aga gtg gaa tct att       49
  Leu Asp Arg Gly Asp Asp Leu Ser Glu Thr Ser Arg Val Glu Ser Ile
  1               5                  10                  15 tct gga aca gac atc tct cct gat gac att gta gga ata att ggc tta         97
Ser Gly Thr Asp Ile Ser Pro Asp Asp Ile Val Gly Ile Ile Gly Leu
             20                  25                  30 aag cgt ttc tgg aaa gcc aga aga gca att gtc aac cag caa aga gtg        145
Lys Arg Phe Trp Lys Ala Arg Arg Ala Ile Val Asn Gln Gln Arg Val
         35                  40                  45 ttt gca atc caa gtg ttc gag ttg cat cga cta ata aag gta caa agg        193
Phe Ala Ile Gln Val Phe Glu Leu His Arg Leu Ile Lys Val Gln Arg
     50                  55                  60 ctc att gcc ggg tca cca aat agt tcg ctc gaa gat cct gct tat tta        241
Leu Ile Ala Gly Ser Pro Asn Ser Ser Leu Glu Asp Pro Ala Tyr Leu
 65                  70                  75                  80 ggc aaa cct tta aag agt tca tcg atc aaa aga ctt cca ttg gac tgt        289
Gly Lys Pro Leu Lys Ser Ser Ser Ile Lys Arg Leu Pro Leu Asp Cys
                 85                  90                  95 att gtt aga gaa tct caa agt gtt ctg aag cgc aag cat gat tct gag        337
Ile Val Arg Glu Ser Gln Ser Val Leu Lys Arg Lys His Asp Ser Glu
            100                 105                 110 aag cct cac ttc agg atg gaa cac act gcc gaa agc aat gtg gga aag        385
Lys Pro His Phe Arg Met Glu His Thr Ala Glu Ser Asn Val Gly Lys
        115                 120                 125 gca tct ctc tct act gtg caa aat ggt agt caa ctc tct agc cac aaa        433
Ala Ser Leu Ser Thr Val Gln Asn Gly Ser Gln Leu Ser Ser His Lys
    130                 135                 140 cca ttt tca gga act cca ctg cct aca cct gta aca aat gat tct aat        481
Pro Phe Ser Gly Thr Pro Leu Pro Thr Pro Val Thr Asn Asp Ser Asn
145                 150                 155                 160 gcg ggt cct tgg tgc ttc caa caa cct tcc ggg cac caa tgg ttg atc        529
Ala Gly Pro Trp Cys Phe Gln Gln Pro Ser Gly His Gln Trp Leu Ile
                165                 170                 175 cca gtg atg tct cct tct gag gga ctt gta tac aag cca ttt tct gga        577
Pro Val Met Ser Pro Ser Glu Gly Leu Val Tyr Lys Pro Phe Ser Gly
            180                 185                 190 cct gga ttc acg agt cct att tgt gga agt ggg cct tca gga tcg agt        625
Pro Gly Phe Thr Ser Pro Ile Cys Gly Ser Gly Pro Ser Gly Ser Ser
        195                 200                 205 cca aca atg ggg aac ttt ttt gct cca aca tat gga gtt cct gct cct        673
Pro Thr Met Gly Asn Phe Phe Ala Pro Thr Tyr Gly Val Pro Ala Pro
    210                 215                 220 aat cct cac tat caa ggt atg gga gtt cct ttt gca cct ccg act ggt        721
Asn Pro His Tyr Gln Gly Met Gly Val Pro Phe Ala Pro Pro Thr Gly
225                 230                 235                 240 cat ggt tac ttt cgg caa tat ggc atg cca gct atg aat cca cca att        769
His Gly Tyr Phe Arg Gln Tyr Gly Met Pro Ala Met Asn Pro Pro Ile
                245                 250                 255
```

| | | | | | | | | | | | | | | | |
|---|---|---|---|---|---|---|---|---|---|---|---|---|---|---|---|
| tca | tca | act | gct | agt | gaa | gaa | tcg | aac | cag | tat | acc | atg | cct | ggt | tta | 817 |
| Ser | Ser | Thr | Ala | Ser | Glu | Glu | Ser | Asn | Gln | Tyr | Thr | Met | Pro | Gly | Leu |
| | | | 260 | | | | | 265 | | | | | 270 | | |

| | | | | | | | | | | | | | | | |
|---|---|---|---|---|---|---|---|---|---|---|---|---|---|---|---|
| caa | cac | cag | ttt | tct | gga | gta | gtt | gat | gac | gtt | caa | cat | tca | aca | tca | 865 |
| Gln | His | Gln | Phe | Ser | Gly | Val | Val | Asp | Asp | Val | Gln | His | Ser | Thr | Ser |
| | | 275 | | | | | 280 | | | | | 285 | | | |

| | | | | | | | | | | | | | | | |
|---|---|---|---|---|---|---|---|---|---|---|---|---|---|---|---|
| gga | ctc | agt | aat | gtt | cta | aat | cag | aag | aaa | gaa | aat | gtc | ccg | gat | gtt | 913 |
| Gly | Leu | Ser | Asn | Val | Leu | Asn | Gln | Lys | Lys | Glu | Asn | Val | Pro | Asp | Val |
| | 290 | | | | | 295 | | | | | 300 | | | | |

| | | | | | | | | | | | | | | | |
|---|---|---|---|---|---|---|---|---|---|---|---|---|---|---|---|
| gta | agg | tat | caa | tcc | aca | aaa | gat | aat | gag | gta | caa | gcc | agc | agt | gca | 961 |
| Val | Arg | Tyr | Gln | Ser | Thr | Lys | Asp | Asn | Glu | Val | Gln | Ala | Ser | Ser | Ala |
| 305 | | | | | 310 | | | | | 315 | | | | | 320 |

| | | | | | | | | | | | | | | | |
|---|---|---|---|---|---|---|---|---|---|---|---|---|---|---|---|
| agt | agt | cct | att | gag | aca | gca | gga | aga | aac | atg | ctc | tct | ctt | ttt | ccc | 1009 |
| Ser | Ser | Pro | Ile | Glu | Thr | Ala | Gly | Arg | Asn | Met | Leu | Ser | Leu | Phe | Pro |
| | | | | 325 | | | | | 330 | | | | | 335 | |

| | | | | | | | | | | | | | | | |
|---|---|---|---|---|---|---|---|---|---|---|---|---|---|---|---|
| acg | tct | cca | gtt | act | gac | aac | cgt | gat | ggt | agc | cct | cag | gct | tgt | gtg | 1057 |
| Thr | Ser | Pro | Val | Thr | Asp | Asn | Arg | Asp | Gly | Ser | Pro | Gln | Ala | Cys | Val |
| | | | 340 | | | | | 345 | | | | | 350 | | |

| | | | | | | | | | | | | | | | |
|---|---|---|---|---|---|---|---|---|---|---|---|---|---|---|---|
| cct | gat | aat | cca | gcc | aga | gtt | atc | aag | gtt | gta | cct | cac | aat | gca | agg | 1105 |
| Pro | Asp | Asn | Pro | Ala | Arg | Val | Ile | Lys | Val | Val | Pro | His | Asn | Ala | Arg |
| | | 355 | | | | | 360 | | | | | 365 | | | |

| | | | | | | | | | | | | | | | |
|---|---|---|---|---|---|---|---|---|---|---|---|---|---|---|---|
| tct | gct | aca | gaa | tcc | gta | gct | cgg | ata | ttt | cag | tct | ata | caa | caa | gag | 1153 |
| Ser | Ala | Thr | Glu | Ser | Val | Ala | Arg | Ile | Phe | Gln | Ser | Ile | Gln | Gln | Glu |
| | 370 | | | | | 375 | | | | | 380 | | | | |

| | | | | | | |
|---|---|---|---|---|---|---|
| aga | aat | aat | atg | act | tag | gtttaacaca tctataagta gcttaccttg | 1201 |
| Arg | Asn | Asn | Met | Thr | | |
| 385 | | | | | | | tgaatatgac catttgctca tcctggcaaa atgtagtagt ttcagtcaat ttgttgtatc   1261 tttcttttct acagaaagta tgtaatagct gtattttaat ttggttgctg tagataagca   1321 tacctgcaaa aaaaaaaaaa aaaaac   1347

<210> SEQ ID NO 23
<211> LENGTH: 389
<212> TYPE: PRT
<213> ORGANISM: Lycopersicon esculentum
<400> SEQUENCE: 23

Leu Asp Arg Gly Asp Asp Leu Ser Glu Thr Ser Arg Val Glu Ser Ile
1               5                   10                  15

Ser Gly Thr Asp Ile Ser Pro Asp Ile Val Gly Ile Ile Gly Leu
            20                  25                  30

Lys Arg Phe Trp Lys Ala Arg Arg Ala Ile Val Asn Gln Gln Arg Val
        35                  40                  45

Phe Ala Ile Gln Val Phe Glu Leu His Arg Leu Ile Lys Val Gln Arg
    50                  55                  60

Leu Ile Ala Gly Ser Pro Asn Ser Ser Leu Glu Asp Pro Ala Tyr Leu
65                  70                  75                  80

Gly Lys Pro Leu Lys Ser Ser Ile Lys Arg Leu Pro Leu Asp Cys
                85                  90                  95

Ile Val Arg Glu Ser Gln Ser Val Leu Lys Arg Lys His Asp Ser Glu
            100                 105                 110

Lys Pro His Phe Arg Met Glu His Thr Ala Glu Ser Asn Val Gly Lys
        115                 120                 125

Ala Ser Leu Ser Thr Val Gln Asn Gly Ser Gln Leu Ser Ser His Lys
    130                 135                 140

Pro Phe Ser Gly Thr Pro Leu Pro Thr Pro Val Thr Asn Asp Ser Asn
145                 150                 155                 160

```
Ala Gly Pro Trp Cys Phe Gln Gln Pro Ser Gly His Gln Trp Leu Ile
                165                 170                 175

Pro Val Met Ser Pro Ser Glu Gly Leu Val Tyr Lys Pro Phe Ser Gly
            180                 185                 190

Pro Gly Phe Thr Ser Pro Ile Cys Gly Ser Gly Pro Ser Gly Ser Ser
        195                 200                 205

Pro Thr Met Gly Asn Phe Ala Pro Thr Tyr Gly Val Pro Ala Pro
    210                 215                 220

Asn Pro His Tyr Gln Gly Met Gly Val Pro Phe Ala Pro Pro Thr Gly
225                 230                 235                 240

His Gly Tyr Phe Arg Gln Tyr Gly Met Pro Ala Met Asn Pro Pro Ile
                245                 250                 255

Ser Ser Thr Ala Ser Glu Glu Ser Asn Gln Tyr Thr Met Pro Gly Leu
            260                 265                 270

Gln His Gln Phe Ser Gly Val Val Asp Asp Val Gln His Ser Thr Ser
        275                 280                 285

Gly Leu Ser Asn Val Leu Asn Gln Lys Lys Glu Asn Val Pro Asp Val
    290                 295                 300

Val Arg Tyr Gln Ser Thr Lys Asp Asn Glu Val Gln Ala Ser Ser Ala
305                 310                 315                 320

Ser Ser Pro Ile Glu Thr Ala Gly Arg Asn Met Leu Ser Leu Phe Pro
                325                 330                 335

Thr Ser Pro Val Thr Asp Asn Arg Asp Gly Ser Pro Gln Ala Cys Val
            340                 345                 350

Pro Asp Asn Pro Ala Arg Val Ile Lys Val Val Pro His Asn Ala Arg
        355                 360                 365

Ser Ala Thr Glu Ser Val Ala Arg Ile Phe Gln Ser Ile Gln Gln Glu
    370                 375                 380

Arg Asn Asn Met Thr
385

<210> SEQ ID NO 24
<211> LENGTH: 179
<212> TYPE: PRT
<213> ORGANISM: Lycopersicon esculentum

<400> SEQUENCE: 24

Met Lys Arg Gly Thr Gly Glu Glu Lys Val Met Gly Pro Met Phe Pro
1               5                   10                  15

Arg Leu Asn Val Asn Asp Thr Glu Lys Gly Gly Pro Arg Ala Pro Pro
            20                  25                  30

Arg Asn Lys Met Ala Leu Tyr Glu Gln Leu Ser Ile Pro Ser Gln Arg
        35                  40                  45

Tyr Asn Pro Gly Asp Leu Pro His Asn Ser Ser Asn Ser Ala Asn Leu
    50                  55                  60

Val Leu Pro His Pro Ser Gln Glu Asn Glu His Glu Arg Gly Val Leu
65                  70                  75                  80

Phe Ser Arg Gln Leu Pro Ala Leu Arg His Pro Val Glu Lys Pro Tyr
                85                  90                  95

Gly Arg Ser Ser Gly Ser Asn Thr Pro Leu Arg Glu Val Lys Ser Lys
            100                 105                 110

Arg Gln Thr Glu Lys Glu Asp Phe Arg Val Pro Thr Phe Asp Asn Ser
        115                 120                 125
```

-continued

```
Lys Glu Arg Ala Val Asn Thr Glu Asp Tyr Ser Lys Gly Thr Ser Asp
    130                 135                 140

Ile Asp Lys Arg Asp Ser Thr Leu Lys Arg Thr Asp Gln Leu Ser His
145                 150                 155                 160

Val Thr Pro Arg Glu Asn Leu Val Asn Thr Phe Gly Glu Ser His Lys
                165                 170                 175

Thr Asn Ile

<210> SEQ ID NO 25
<211> LENGTH: 49
<212> TYPE: PRT
<213> ORGANISM: Lycopersicon esculentum

<400> SEQUENCE: 25

Met Lys Arg Gly Lys Gly Glu Glu Lys Leu Met Gly Pro Met Phe Pro
1               5                   10                  15

Arg Leu His Val Asn Asp Thr Glu Lys Gly Gly Pro Lys Ala Pro Pro
                20                  25                  30

Arg Asn Lys Met Ala Leu Tyr Glu Gln Leu Ser Ile Pro Ser Gln Arg
        35                  40                  45

Phe

<210> SEQ ID NO 26
<211> LENGTH: 4478
<212> TYPE: DNA
<213> ORGANISM: Oryza sativa
<220> FEATURE:
<221> NAME/KEY: exon
<222> LOCATION: (1)..(261)
<220> FEATURE:
<221> NAME/KEY: Intron
<222> LOCATION: (262)..(1659)
<220> FEATURE:
<221> NAME/KEY: exon
<222> LOCATION: (1660)..(2645)
<220> FEATURE:
<221> NAME/KEY: Intron
<222> LOCATION: (2646)..(3329)
<220> FEATURE:
<221> NAME/KEY: exon
<222> LOCATION: (3330)..(3381)
<220> FEATURE:
<221> NAME/KEY: Intron
<222> LOCATION: (3382)..(3494)
<220> FEATURE:
<221> NAME/KEY: exon
<222> LOCATION: (3495)..(4478)

<400> SEQUENCE: 26 atg gcg acg agg gga gga ggc gga gga gga gga ggg aag gag gcg aag      48
Met Ala Thr Arg Gly Gly Gly Gly Gly Gly Gly Lys Glu Ala Lys
1               5                   10                  15 ggg aag gtg atg ggc ccg ctg ttc ccg cgg ctc cac gtc aac gac gcg      96
Gly Lys Val Met Gly Pro Leu Phe Pro Arg Leu His Val Asn Asp Ala
                20                  25                  30 gcc aag ggc gga ggc ccg cgg gcg ccg ccc cgg aac aag atg gcg ctc     144
Ala Lys Gly Gly Gly Pro Arg Ala Pro Pro Arg Asn Lys Met Ala Leu
        35                  40                  45 tac gag cag ttc acc gtg ccc tcg cat cgc ttc agc ggc gga gga ggc     192
Tyr Glu Gln Phe Thr Val Pro Ser His Arg Phe Ser Gly Gly Gly Gly
    50                  55                  60 ggc ggc gga gta gga ggc agc ccc gcg cac tcg acg tcg gcg gcg agc     240
Gly Gly Gly Val Gly Gly Ser Pro Ala His Ser Thr Ser Ala Ala Ser
65                  70                  75                  80
```

-continued

```
cag agc cag agc cag agc cag gtgactcgac gtcctgcccg tatgatcgat        291
Gln Ser Gln Ser Gln Ser Gln
                85 tcgattgggg gtagtgtgtg cgactgctaa attggtacta gtaggcgaca attctgtgca    351 aatggagcta aacgccttgc aaatcgaatc gaattagaag cctaaattgg taggcaataa    411 ttctgtgcaa tggagctaaa cttccttgca atcgaatag aactaaaagc tgggaagata     471 atttcgaggc acaaatggtg ccctcgacgt cgacgagcta ggtcagaggg ggcgtttcac    531 gccttaccct ttgtagttat ctcggttggg atagatgaat tgatgggcga atttagtgca    591 acggagctaa acacatggaa aaattggata agattaaggc cgagaagccc agtttgaggc    651 acaaatgcca tgttcctttt gtgctgatta atctatcatg ccgtcgacat gtgattcaat    711 tacttgcaaa tatagtcata caattgtggt aggagtaaca tgcttgcacg ttgtcatagt    771 gtcattattg atctttctcc gtgctgataa ctcacttgtg ttgaaggcga aagagcagaa    831 caaaaccatt atatgcagtt tacatcagct cttccggtaa agttttggag acggggcata    891 agttccttgc aaacaatatc ggatattata gcttattgca aattgtatat ggccagatat    951 gctatgattg tgtttgctga ggtctggtgt ttgtaatata caaacaaaaa ggtccacatg    1011 tgaaactgca tgtagcgcag gtggcaaaga gtagccgtag tgctgctcaa cgtactgtgt    1071 tctattctcc ctgacgtgct caccttcctt aaatcattga cactaggttc ctccttagtg    1131 tcttgcattt ttgcctgccg aaaaaaaaag gtccacgtga agggaatga taaaaatggt     1191 ggttgatatg ctttgattgt caggcacacg ttcaacctgt atgtgataaa atcaacggt     1251 tttctaatac tgttttcagc aaggatttag gagtggaaaa tattctttag aacaaatctg    1311 caatagcctc ccacaacaca tccaactacc ttttgataat gggatagtta tagacatgaa    1371 gtgcgaatgg caaagtcca agtcatagat ttccaaatga agaaatgtga acaaaataag     1431 aaagaaagaa gtccatttgc agtattatgt ctcttttgcc cttctttggg tcgaaaataa    1491 aataaaaaat cgagatctta ccatgagata cttaatctcc caccactttt tctaattcaa    1551 catgggaagtt cttggatagt ttaaatacgc ttcctaccaa ttagcgtgga atcctcgcaa   1611 tttttcacta aatctagtag tactgaaatg gattttattt tcttccag gtt tat gga    1668
                                                    Val Tyr Gly
                                                            90 cgt gac agt tct ctg ttc cag ccg ttc aat gtg cct tcc aat cga cct     1716
Arg Asp Ser Ser Leu Phe Gln Pro Phe Asn Val Pro Ser Asn Arg Pro
            95                 100                 105 ggc cat tct act gaa aag atc aat tca gat aag atc aac aag aag att     1764
Gly His Ser Thr Glu Lys Ile Asn Ser Asp Lys Ile Asn Lys Lys Ile
        110                 115                 120 agt ggt tca aga aaa gaa ctg ggg atg tta tcc tct cag act aag ggc     1812
Ser Gly Ser Arg Lys Glu Leu Gly Met Leu Ser Ser Gln Thr Lys Gly
    125                 130                 135 atg gat att tat gct tca aga tca act gct gag gca cca caa aga aga     1860
Met Asp Ile Tyr Ala Ser Arg Ser Thr Ala Glu Ala Pro Gln Arg Arg
140                 145                 150 gca gaa aat aca ata aag agt tct tcg gga aag aga ttg gcc gat gat     1908
Ala Glu Asn Thr Ile Lys Ser Ser Ser Gly Lys Arg Leu Ala Asp Asp
155                 160                 165                 170 gat gaa ttt atg gtt cct tct gtc ttc aat tcc aga ttt cct caa tat     1956
Asp Glu Phe Met Val Pro Ser Val Phe Asn Ser Arg Phe Pro Gln Tyr
            175                 180                 185
```

```
agt act caa gag aat gca ggg gtt caa gac caa tca aca ccc ctt gtt    2004
Ser Thr Gln Glu Asn Ala Gly Val Gln Asp Gln Ser Thr Pro Leu Val
        190                 195                 200 gct gca aat cca cac aaa agc cct tca aca gtg tcc aaa tca tcc aca    2052
Ala Ala Asn Pro His Lys Ser Pro Ser Thr Val Ser Lys Ser Ser Thr
                205                 210                 215 aag tgt tat aac act gtt agc aag aaa ttg gag aga atc cat gtt tct    2100
Lys Cys Tyr Asn Thr Val Ser Lys Lys Leu Glu Arg Ile His Val Ser
220                 225                 230 gat gtg aaa tca agg acc cct ttg aaa gac aag gag atg gaa gca gca    2148
Asp Val Lys Ser Arg Thr Pro Leu Lys Asp Lys Glu Met Glu Ala Ala
235                 240                 245                 250 cag aca tcc aaa aac gtg gaa gtt gaa aaa agt tca tcc ttt cat gct    2196
Gln Thr Ser Lys Asn Val Glu Val Glu Lys Ser Ser Ser Phe His Ala
                255                 260                 265 tcc aaa gat atg ttt gaa agc agg cat gct aaa gta tat cct aag atg    2244
Ser Lys Asp Met Phe Glu Ser Arg His Ala Lys Val Tyr Pro Lys Met
            270                 275                 280 gat aag acg ggc att ata aat gat tct gat gag cca cat ggt gga aat    2292
Asp Lys Thr Gly Ile Ile Asn Asp Ser Asp Glu Pro His Gly Gly Asn
        285                 290                 295 agt ggg cat caa gcg aca agc aga aat gga ggt tcc atg aaa ttt cag    2340
Ser Gly His Gln Ala Thr Ser Arg Asn Gly Gly Ser Met Lys Phe Gln
    300                 305                 310 aac cct cca atg aga aga aat gaa att tcc tct aat cca tct tct gaa    2388
Asn Pro Pro Met Arg Arg Asn Glu Ile Ser Ser Asn Pro Ser Ser Glu
315                 320                 325                 330 aat act gat agg cat tat aat tta ccg caa gga ggc ata gag gaa aca    2436
Asn Thr Asp Arg His Tyr Asn Leu Pro Gln Gly Gly Ile Glu Glu Thr
                335                 340                 345 ggt aca aag aga aaa agg ttg cta gaa caa cac gat gca gag aaa agt    2484
Gly Thr Lys Arg Lys Arg Leu Leu Glu Gln His Asp Ala Glu Lys Ser
            350                 355                 360 gat gat gtg tca agg ttg cta gaa caa cac gat gca gag aac att gat    2532
Asp Asp Val Ser Arg Leu Leu Glu Gln His Asp Ala Glu Asn Ile Asp
        365                 370                 375 gat gtg tct gat tcc tcg gtg gag tgt ata act ggt tgg gag att tct    2580
Asp Val Ser Asp Ser Ser Val Glu Cys Ile Thr Gly Trp Glu Ile Ser
    380                 385                 390 cca gat aaa att gtt gga gcc att ggt aca aag cat ttc tgg aaa gca    2628
Pro Asp Lys Ile Val Gly Ala Ile Gly Thr Lys His Phe Trp Lys Ala
395                 400                 405                 410 aga cgt gct att atg aa  gtaagtaaaa ctatccttt gagcttagtt           2675
Arg Arg Ala Ile Met Asn
                415 tggcccactc aaactagact tgtttgcagc tctaattacg tataggtagc tttgatgaat    2735 aaaatttgtt ttgtttccct tgctttactg ttatttgctc ttaatttgcg gttgatctta    2795 atcatcttag acagaaaaac atgatgacta tctcgtttgt ttttggttta tttcatattt    2855 gaatgccaat agatgtcagc tccagatgat atttcaaata cctcatgcat ggaaactgtg    2915 catacttatg ccaaattttg ggcttacaag tcagcatgtc tacaaatttc tttggcagaa    2975 ttaatatata tctagttcaa catttgctga tttgtaattg gattagttgt ctgcagaatg    3035 ccggcatgtt ttattttcct ttcaactagg tcaatcagtt ttgttgttgt ctgttgttct    3095 tgtccaccta cacctgtact actgaaatgt tctcttttgg agatgtcaat gaaaatttta    3155 atctatagtg gtttcaattt tattttcatt ttagtcaaga agaatggcat aatctcattt    3215
```

-continued

| | |
|---|---|
| aaaaagattg taaaagtgtc cctgttaaag tgatattgta ggtattgctt taccaagcta | 3275 |
| ctgtatgatt cccttattg ttttacactc taatcttctt taaactctat gcag t caa<br>                                                                                                        Gln | 3333 |
| cag agg gtg ttt gct gtc cag gtt ttt gag ctg cat aag ttg gta aaa<br>Gln Arg Val Phe Ala Val Gln Val Phe Glu Leu His Lys Leu Val Lys<br>                420                      425                        430 | 3381 |
| gtgagtctag caaatttctc ttccttctag ccactcttaa gcaggttaat tcgtggatag | 3441 |
| gattttgtcc ataatctgtt tataacccac acttgtattt gacttacaat cag gtg<br>                                                                                           Val | 3497 |
| cag aag ttg att gca gca tcg cca cat gta ctt att gaa agt gat cct<br>Gln Lys Leu Ile Ala Ala Ser Pro His Val Leu Ile Glu Ser Asp Pro<br>435                      440                      445                      450 | 3545 |
| tgc ctt ggc aat gcc ttg ttg ggt agc aag aac aag ctg gtg gaa gaa<br>Cys Leu Gly Asn Ala Leu Leu Gly Ser Lys Asn Lys Leu Val Glu Glu<br>                                455                      460                      465 | 3593 |
| aac ctg aaa gca caa cct ctt tta gtc gca acc atc gat gac gtg gag<br>Asn Leu Lys Ala Gln Pro Leu Leu Val Ala Thr Ile Asp Asp Val Glu<br>                470                      475                      480 | 3641 |
| cca agt cta cag caa ccg gag gta tca aaa gaa aac act gaa gac agc<br>Pro Ser Leu Gln Gln Pro Glu Val Ser Lys Glu Asn Thr Glu Asp Ser<br>                      485                      490                      495 | 3689 |
| cca ccc tcc cct cat gat act ggg ctt ggc agt ggt caa cgt gat caa<br>Pro Pro Ser Pro His Asp Thr Gly Leu Gly Ser Gly Gln Arg Asp Gln<br>500                      505                      510 | 3737 |
| gct gca aca aat ggc gtc tct aaa agc aat cgt cga gct aca cct gtt<br>Ala Ala Thr Asn Gly Val Ser Lys Ser Asn Arg Arg Ala Thr Pro Val<br>515                      520                      525                      530 | 3785 |
| gct tct gat aac aaa caa aat aac tgg ggc gtt caa ctt caa cca cct<br>Ala Ser Asp Asn Lys Gln Asn Asn Trp Gly Val Gln Leu Gln Pro Pro<br>                                535                      540                      545 | 3833 |
| caa aat caa tgg ctt gtc cct gtc atg tct cct ttg gaa ggc ctt gtc<br>Gln Asn Gln Trp Leu Val Pro Val Met Ser Pro Leu Glu Gly Leu Val<br>                550                      555                      560 | 3881 |
| tat aag cct tat tct ggt ccg tgc cct cca gct ggt agc ata ttg gcc<br>Tyr Lys Pro Tyr Ser Gly Pro Cys Pro Pro Ala Gly Ser Ile Leu Ala<br>                      565                      570                      575 | 3929 |
| ccg ttt tat gcc aac tgt act cct ttg agt ctt cca tca aca gct gga<br>Pro Phe Tyr Ala Asn Cys Thr Pro Leu Ser Leu Pro Ser Thr Ala Gly<br>580                      585                      590 | 3977 |
| gat ttc atg aac tcg gca tac ggt gtt cct atg cct cat cag cca caa<br>Asp Phe Met Asn Ser Ala Tyr Gly Val Pro Met Pro His Gln Pro Gln<br>595                      600                      605                      610 | 4025 |
| cat atg ggt gct cct ggc cct cct tcc atg cct atg aac tac ttc ccg<br>His Met Gly Ala Pro Gly Pro Pro Ser Met Pro Met Asn Tyr Phe Pro<br>                                615                      620                      625 | 4073 |
| cct ttc agc ata cca gtg atg aac cca act gca ccg gca cct gta gtc<br>Pro Phe Ser Ile Pro Val Met Asn Pro Thr Ala Pro Ala Pro Val Val<br>                          630                      635                      640 | 4121 |
| gaa caa ggg aga cat cct tcg atg cca cag cct tat ggg aac ttt gag<br>Glu Gln Gly Arg His Pro Ser Met Pro Gln Pro Tyr Gly Asn Phe Glu<br>                      645                      650                      655 | 4169 |
| cag cag tcg tgg atc tca tgt aac atg tca cat cca agt ggc att tgg<br>Gln Gln Ser Trp Ile Ser Cys Asn Met Ser His Pro Ser Gly Ile Trp<br>                660                      665                      670 | 4217 |
| aga ttt cat gcc tca aga gat agc gag gca cag gcc agc agc gct agc<br>Arg Phe His Ala Ser Arg Asp Ser Glu Ala Gln Ala Ser Ser Ala Ser<br>675                      680                      685                      690 | 4265 |

```
agt cct ttt gac agg ttc caa tgc agt gga agt ggt cct gta tcc gcc    4313
Ser Pro Phe Asp Arg Phe Gln Cys Ser Gly Ser Gly Pro Val Ser Ala
            695                 700                 705 ttc ccc aca gta tca gct cag aac aac cag cct cag ccc tca tat agc    4361
Phe Pro Thr Val Ser Ala Gln Asn Asn Gln Pro Gln Pro Ser Tyr Ser
            710                 715                 720 agc cgg gac aac cag acc aat gtt atc aag gtt gtt cca cat aat tca    4409
Ser Arg Asp Asn Gln Thr Asn Val Ile Lys Val Val Pro His Asn Ser
            725                 730                 735 cga act gct tca gag tca gca gca cgg att ttc cgg tca ata caa atg    4457
Arg Thr Ala Ser Glu Ser Ala Ala Arg Ile Phe Arg Ser Ile Gln Met
            740                 745                 750 gaa cgg caa cga gat gat tga                                        4478
Glu Arg Gln Arg Asp Asp
755                 760

<210> SEQ ID NO 27
<211> LENGTH: 760
<212> TYPE: PRT
<213> ORGANISM: Oryza sativa

<400> SEQUENCE: 27

Met Ala Thr Arg Gly Gly Gly Gly Gly Gly Lys Glu Ala Lys
1               5                   10                  15

Gly Lys Val Met Gly Pro Leu Phe Pro Arg Leu His Val Asn Asp Ala
                20                  25                  30

Ala Lys Gly Gly Gly Pro Arg Ala Pro Arg Asn Lys Met Ala Leu
            35                  40                  45

Tyr Glu Gln Phe Thr Val Pro Ser His Arg Phe Ser Gly Gly Gly
    50                  55                  60

Gly Gly Gly Val Gly Gly Ser Pro Ala His Ser Thr Ser Ala Ala Ser
65                  70                  75                  80

Gln Ser Gln Ser Gln Ser Gln Val Tyr Gly Arg Asp Ser Ser Leu Phe
                85                  90                  95

Gln Pro Phe Asn Val Pro Ser Asn Arg Pro Gly His Ser Thr Glu Lys
            100                 105                 110

Ile Asn Ser Asp Lys Ile Asn Lys Lys Ile Ser Gly Ser Arg Lys Glu
        115                 120                 125

Leu Gly Met Leu Ser Ser Gln Thr Lys Gly Met Asp Ile Tyr Ala Ser
    130                 135                 140

Arg Ser Thr Ala Glu Ala Pro Gln Arg Arg Ala Glu Asn Thr Ile Lys
145                 150                 155                 160

Ser Ser Ser Gly Lys Arg Leu Ala Asp Asp Asp Glu Phe Met Val Pro
                165                 170                 175

Ser Val Phe Asn Ser Arg Phe Pro Gln Tyr Ser Thr Gln Glu Asn Ala
            180                 185                 190

Gly Val Gln Asp Gln Ser Thr Pro Leu Val Ala Ala Asn Pro His Lys
        195                 200                 205

Ser Pro Ser Thr Val Ser Lys Ser Ser Thr Lys Cys Tyr Asn Thr Val
    210                 215                 220

Ser Lys Lys Leu Glu Arg Ile His Val Ser Asp Val Lys Ser Arg Thr
225                 230                 235                 240

Pro Leu Lys Asp Lys Glu Met Glu Ala Ala Gln Thr Ser Lys Asn Val
                245                 250                 255

Glu Val Glu Lys Ser Ser Ser Phe His Ala Ser Lys Asp Met Phe Glu
            260                 265                 270
```

-continued

```
Ser Arg His Ala Lys Val Tyr Pro Lys Met Asp Lys Thr Gly Ile Ile
        275                 280                 285
Asn Asp Ser Asp Glu Pro His Gly Gly Asn Ser Gly His Gln Ala Thr
    290                 295                 300
Ser Arg Asn Gly Gly Ser Met Lys Phe Gln Asn Pro Pro Met Arg Arg
305                 310                 315                 320
Asn Glu Ile Ser Ser Asn Pro Ser Ser Glu Asn Thr Asp Arg His Tyr
                325                 330                 335
Asn Leu Pro Gln Gly Gly Ile Glu Glu Thr Gly Thr Lys Arg Lys Arg
            340                 345                 350
Leu Leu Glu Gln His Asp Ala Glu Lys Ser Asp Asp Val Ser Arg Leu
        355                 360                 365
Leu Glu Gln His Asp Ala Glu Asn Ile Asp Asp Val Ser Asp Ser Ser
    370                 375                 380
Val Glu Cys Ile Thr Gly Trp Glu Ile Ser Pro Asp Lys Ile Val Gly
385                 390                 395                 400
Ala Ile Gly Thr Lys His Phe Trp Lys Ala Arg Arg Ala Ile Met Asn
                405                 410                 415
Gln Gln Arg Val Phe Ala Val Gln Val Phe Glu Leu His Lys Leu Val
            420                 425                 430
Lys Val Gln Lys Leu Ile Ala Ala Ser Pro His Val Leu Ile Glu Ser
        435                 440                 445
Asp Pro Cys Leu Gly Asn Ala Leu Leu Gly Ser Lys Asn Lys Leu Val
    450                 455                 460
Glu Glu Asn Leu Lys Ala Gln Pro Leu Leu Val Ala Thr Ile Asp Asp
465                 470                 475                 480
Val Glu Pro Ser Leu Gln Pro Glu Val Ser Lys Glu Asn Thr Glu
                485                 490                 495
Asp Ser Pro Pro Ser Pro His Asp Thr Gly Leu Gly Ser Gly Gln Arg
            500                 505                 510
Asp Gln Ala Ala Thr Asn Gly Val Ser Lys Ser Asn Arg Arg Ala Thr
        515                 520                 525
Pro Val Ala Ser Asp Asn Lys Gln Asn Asn Trp Gly Val Gln Leu Gln
    530                 535                 540
Pro Pro Gln Asn Gln Trp Leu Val Pro Val Met Ser Pro Leu Glu Gly
545                 550                 555                 560
Leu Val Tyr Lys Pro Tyr Ser Gly Pro Cys Pro Pro Ala Gly Ser Ile
                565                 570                 575
Leu Ala Pro Phe Tyr Ala Asn Cys Thr Pro Leu Ser Leu Pro Ser Thr
            580                 585                 590
Ala Gly Asp Phe Met Asn Ser Ala Tyr Gly Val Pro Met Pro His Gln
        595                 600                 605
Pro Gln His Met Gly Ala Pro Gly Pro Ser Met Pro Met Asn Tyr
    610                 615                 620
Phe Pro Pro Phe Ser Ile Pro Val Met Asn Pro Thr Ala Pro Ala Pro
625                 630                 635                 640
Val Val Glu Gln Gly Arg His Pro Ser Met Pro Gln Pro Tyr Gly Asn
                645                 650                 655
Phe Glu Gln Gln Ser Trp Ile Ser Cys Asn Met Ser His Pro Ser Gly
            660                 665                 670
Ile Trp Arg Phe His Ala Ser Arg Asp Ser Glu Ala Gln Ala Ser Ser
        675                 680                 685
```

```
Ala Ser Ser Pro Phe Asp Arg Phe Gln Cys Ser Gly Ser Gly Pro Val
    690             695                 700
Ser Ala Phe Pro Thr Val Ser Ala Gln Asn Asn Gln Pro Gln Pro Ser
705             710                 715                 720
Tyr Ser Ser Arg Asp Asn Gln Thr Asn Val Ile Lys Val Val Pro His
                725                 730                 735
Asn Ser Arg Thr Ala Ser Glu Ser Ala Ala Arg Ile Phe Arg Ser Ile
            740                 745                 750
Gln Met Glu Arg Gln Arg Asp Asp
        755                 760

<210> SEQ ID NO 28
<211> LENGTH: 938
<212> TYPE: DNA
<213> ORGANISM: Zea mays

<400> SEQUENCE: 28
gacgtggagc aaaacgatga tctgtctgat tcctctgttg aatctttgcc tggaatggag      60
atttctccag atgatgttgt cagtgctatt ggtcccaagc attttggaa agcgagaaga      120 gctattgtca atcagcagag ggtatttgct gttcaagtat tcgagctgca taggttgatc      180
aaagtgcaga agttgatcgc tgcatctcca catgtactta ttgaggggga tccttgcctt      240
ggcaaatcct tggcggtgag cmagaaaagg ctgaagtcag tggctgattc ccgtwatgtc      300
cccgtttgaa ggacttgtct acaagcctta tcccgggsca ytgccctccg gtggaagtct      360
tttggcgccc ccatttttg ccagctaccc cacctcttcc tcctcacag ctgggggga       420 tttcatgagt tcggcatgtg gagccaggct gatgagtgcc cctgtgtact tcccgtcttt      480
cagcatgcct gcagtgtcag ggtctgcagt tgagcaagtg agccatgttg cagcgtcgca      540
gcataaacgg aactcgtgta gtgaagcggt gttggcatca agggacagcg aggtgcaagg      600
cagtagtgct agcagtccgg catcttctga acagcagct caacccaggg tcattagggt       660
tgttccccac acggcacgca cggcttcaga gtcggcagca aggattttcc gctcaataca      720
gatggagagg aaacaaaacg acccgtgact ggcagataaa aatgaaagaa cggagggagt      780
agactaattt tttgaccgat aattataatg atcgccgtaa attggctggc ccgcccgcct      840 tatgttttttt gttcagtgta aatatgctgt gtctgtcaga atgatatggc atctgtagct      900
attttggttc tgtcagaatc atgttgattg gaattaaa                            938

<210> SEQ ID NO 29
<211> LENGTH: 248
<212> TYPE: PRT
<213> ORGANISM: Zea mays
<220> FEATURE:
<221> NAME/KEY: UNSURE
<222> LOCATION: (88)..(88)
<220> FEATURE:
<221> NAME/KEY: unsure
<222> LOCATION: (98)..(98)
<223> OTHER INFORMATION: amino acid not confirmed, based on nucleic acid
      sequence
<220> FEATURE:
<221> NAME/KEY: unsure
<222> LOCATION: (113)..(113)
<223> OTHER INFORMATION: amino acid not confirmed, based on nucleic acid
      sequence
<220> FEATURE:
<221> NAME/KEY: unsure
<222> LOCATION: (114)..(114)
<223> OTHER INFORMATION: amino acid not confirmed, based on nucleic acid
      sequence
```

-continued

<400> SEQUENCE: 29

| | | | | | | | | | | | | | | | |
|---|---|---|---|---|---|---|---|---|---|---|---|---|---|---|---|
| Asp | Val | Glu | Gln | Asn | Asp | Leu | Ser | Asp | Ser | Val | Glu | Ser | Leu | | |
| 1 | | | | 5 | | | | | 10 | | | | | 15 | |

Pro Gly Met Glu Ile Ser Pro Asp Asp Val Val Ser Ala Ile Gly Pro
            20                  25                  30

Lys His Phe Trp Lys Ala Arg Arg Ala Ile Val Asn Gln Gln Arg Val
                35                  40                  45

Phe Ala Val Gln Val Phe Glu Leu His Arg Leu Ile Lys Val Gln Lys
    50                  55                  60

Leu Ile Ala Ala Ser Pro His Val Leu Ile Glu Gly Asp Pro Cys Leu
65                  70                  75                  80

Gly Lys Ser Leu Ala Val Ser Xaa Lys Arg Leu Ser Gln Trp Leu Ile
                85                  90                  95

Pro Xaa Met Ser Pro Phe Glu Gly Leu Val Tyr Lys Pro Tyr Pro Gly
            100                 105                 110

Xaa Xaa Pro Ser Gly Gly Ser Leu Leu Ala Pro Pro Phe Phe Ala Ser
            115                 120                 125

Tyr Pro Thr Ser Ser Ser Thr Ala Gly Gly Asp Phe Met Ser Ser
    130                 135                 140

Ala Cys Gly Ala Arg Leu Met Ser Ala Pro Val Tyr Phe Pro Ser Phe
145                 150                 155                 160

Ser Met Pro Ala Val Ser Gly Ser Ala Val Glu Gln Val Ser His Val
                165                 170                 175

Ala Ala Ser Gln His Lys Arg Asn Ser Cys Ser Glu Ala Val Leu Ala
            180                 185                 190

Ser Arg Asp Ser Glu Val Gln Gly Ser Ser Ala Ser Ser Pro Ala Ser
            195                 200                 205

Ser Glu Thr Ala Ala Gln Pro Arg Val Ile Arg Val Val Pro His Thr
    210                 215                 220

Ala Arg Thr Ala Ser Glu Ser Ala Ala Arg Ile Phe Arg Ser Ile Gln
225                 230                 235                 240

Met Glu Arg Lys Gln Asn Asp Pro
                245

<210> SEQ ID NO 30
<211> LENGTH: 625
<212> TYPE: DNA
<213> ORGANISM: Zea mays
<220> FEATURE:
<221> NAME/KEY: exon
<222> LOCATION: (1)..(570)
<220> FEATURE:
<221> NAME/KEY: 3'UTR
<222> LOCATION: (571)..(625)

<400> SEQUENCE: 30

| gca | cga | ggg | cac | atg | gtc | cct | cct | ggc | gcc | cct | gcc | atg | cat | atg | aac | 48 |
|---|---|---|---|---|---|---|---|---|---|---|---|---|---|---|---|---|
| Ala | Arg | Gly | His | Met | Val | Pro | Pro | Gly | Ala | Pro | Ala | Met | His | Met | Asn | |
| 1 | | | | 5 | | | | | 10 | | | | | 15 | | |

| tac | ttc | ccg | cct | ttc | agt | atg | cca | gtg | atg | aat | cca | gga | aca | cca | gca | 96 |
|---|---|---|---|---|---|---|---|---|---|---|---|---|---|---|---|---|
| Tyr | Phe | Pro | Pro | Phe | Ser | Met | Pro | Val | Met | Asn | Pro | Gly | Thr | Pro | Ala | |
| | | | 20 | | | | | 25 | | | | | 30 | | | |

| tct | gca | gtg | gag | caa | ggg | agc | cat | gct | gct | gcg | cca | cag | cct | cat | ggg | 144 |
|---|---|---|---|---|---|---|---|---|---|---|---|---|---|---|---|---|
| Ser | Ala | Val | Glu | Gln | Gly | Ser | His | Ala | Ala | Ala | Pro | Gln | Pro | His | Gly | |
| | | 35 | | | | | 40 | | | | | 45 | | | | |

| cac | atg | gac | cag | cag | tcg | ctg | atc | tca | tgt | aac | atg | tca | cac | ccg | agt | 192 |
|---|---|---|---|---|---|---|---|---|---|---|---|---|---|---|---|---|
| His | Met | Asp | Gln | Gln | Ser | Leu | Ile | Ser | Cys | Asn | Met | Ser | His | Pro | Ser | |
| | 50 | | | | | 55 | | | | | 60 | | | | | |

```
ggc gtt tgg agg ttt ctt gca tca agg gac agc gag cca cag gcc agc      240
Gly Val Trp Arg Phe Leu Ala Ser Arg Asp Ser Glu Pro Gln Ala Ser
65                  70                  75                  80 agc gcc acc agc cct ttc gac agg ctc caa gtc caa ggt gat gga agt      288
Ser Ala Thr Ser Pro Phe Asp Arg Leu Gln Val Gln Gly Asp Gly Ser
                85                  90                  95 gct ccg ttg tca ttc ttt ccc acg gct tca gct ccg aat gtc cag cct      336
Ala Pro Leu Ser Phe Phe Pro Thr Ala Ser Ala Pro Asn Val Gln Pro
            100                 105                 110 ccg ccc tca tct gga ggc cgg gac cgg gac cag cag aac cat gta atc      384
Pro Pro Ser Ser Gly Gly Arg Asp Arg Asp Gln Gln Asn His Val Ile
        115                 120                 125 agg gtt gtt ccg cgt aac gca cag act gct tca gtc ccg aaa gcc caa      432
Arg Val Val Pro Arg Asn Ala Gln Thr Ala Ser Val Pro Lys Ala Gln
130                 135                 140 cct cag ccg tca tcc gga ggc cgg gac caa aag aac cat gta atc agg      480
Pro Gln Pro Ser Ser Gly Gly Arg Asp Gln Lys Asn His Val Ile Arg
145                 150                 155                 160 gtt gtt ccg cat aac gcg cag act gct tcg gag tca gca gcg tgg atc      528
Val Val Pro His Asn Ala Gln Thr Ala Ser Glu Ser Ala Ala Trp Ile
                165                 170                 175 ttc cgg tca ata caa atg gag agg aac caa aat gat tcg tag              570
Phe Arg Ser Ile Gln Met Glu Arg Asn Gln Asn Asp Ser
            180                 185 ctggttacca tatactttcg tgtcatccga tggcagctta gtgcagcatt gcagt         625

<210> SEQ ID NO 31
<211> LENGTH: 189
<212> TYPE: PRT
<213> ORGANISM: Zea mays

<400> SEQUENCE: 31

Ala Arg Gly His Met Val Pro Pro Gly Ala Pro Ala Met His Met Asn
1               5                   10                  15

Tyr Phe Pro Pro Phe Ser Met Pro Val Met Asn Pro Gly Thr Pro Ala
                20                  25                  30

Ser Ala Val Glu Gln Gly Ser His Ala Ala Pro Gln Pro His Gly
            35                  40                  45

His Met Asp Gln Gln Ser Leu Ile Ser Cys Asn Met Ser His Pro Ser
        50                  55                  60

Gly Val Trp Arg Phe Leu Ala Ser Arg Asp Ser Glu Pro Gln Ala Ser
65                  70                  75                  80

Ser Ala Thr Ser Pro Phe Asp Arg Leu Gln Val Gln Gly Asp Gly Ser
                85                  90                  95

Ala Pro Leu Ser Phe Phe Pro Thr Ala Ser Ala Pro Asn Val Gln Pro
            100                 105                 110

Pro Pro Ser Ser Gly Gly Arg Asp Arg Asp Gln Gln Asn His Val Ile
        115                 120                 125

Arg Val Val Pro Arg Asn Ala Gln Thr Ala Ser Val Pro Lys Ala Gln
130                 135                 140

Pro Gln Pro Ser Ser Gly Gly Arg Asp Gln Lys Asn His Val Ile Arg
145                 150                 155                 160

Val Val Pro His Asn Ala Gln Thr Ala Ser Glu Ser Ala Ala Trp Ile
                165                 170                 175

Phe Arg Ser Ile Gln Met Glu Arg Asn Gln Asn Asp Ser
            180                 185
```

```
<210> SEQ ID NO 32
<211> LENGTH: 2794
<212> TYPE: DNA
<213> ORGANISM: Arabidopsis thaliana
<220> FEATURE:
<221> NAME/KEY: 5'UTR
<222> LOCATION: (1)..(476)
<220> FEATURE:
<221> NAME/KEY: exon
<222> LOCATION: (479)..(706)
<220> FEATURE:
<221> NAME/KEY: Intron
<222> LOCATION: (707)..(833)
<220> FEATURE:
<221> NAME/KEY: exon
<222> LOCATION: (834)..(1384)
<220> FEATURE:
<221> NAME/KEY: Intron
<222> LOCATION: (1385)..(1471)
<220> FEATURE:
<221> NAME/KEY: exon
<222> LOCATION: (1472)..(1523)
<220> FEATURE:
<221> NAME/KEY: Intron
<222> LOCATION: (1524)..(1591)
<220> FEATURE:
<221> NAME/KEY: exon
<222> LOCATION: (1592)..(2383)
<220> FEATURE:
<221> NAME/KEY: 3'UTR
<222> LOCATION: (2384)..(2794)

<400> SEQUENCE: 32
taaaagaccg agtcacccga acatctccac cttcacgcca ttctcctacc actcggacct      60
aaccaaccaa taccttccac gtcatgtaca atccgagttc ccgtgagata gggatcttta    120
cttgaagcaa ccagacatga ccgcagagtc acacacacac acacccctaa gcttttttgtc   180 gtcccctcgt atggaatcca ttgtgggacg acacaaaaat atcttctttt gcttctctgc    240
tttcttcttc ttcttcttaa aatttgtttc tttcaggtgg atttgatctc catctacgta    300
aaacaaaaac aaagtttata atcttttttgg attttgggat tgatctaaag tgagatttcg   360
atcttggcac taggttttgc aaggttacct aacaatttct ggttctgatt tcatttcttt   420
aggttacgtg taagggaagg aattgttaat agggtttgtt tgtgagcgta gggaaaag     478 atg gga gga atg aaa gat gaa gca aag agg ata aca att cct cca ttg      526
Met Gly Gly Met Lys Asp Glu Ala Lys Arg Ile Thr Ile Pro Pro Leu
1               5                   10                  15 ttt cca agg gtt cat gtc aat gat act gga aga gga ggc ctg tct caa      574
Phe Pro Arg Val His Val Asn Asp Thr Gly Arg Gly Gly Leu Ser Gln
                20                  25                  30 caa ttt gat ggc aaa aca atg tct ctc gtc tct tct aaa cgt ccc aat      622
Gln Phe Asp Gly Lys Thr Met Ser Leu Val Ser Ser Lys Arg Pro Asn
            35                  40                  45 ctt cct tct ccg acc aac aac ata tct gat tct ctt tcc act ttc tct      670
Leu Pro Ser Pro Thr Asn Asn Ile Ser Asp Ser Leu Ser Thr Phe Ser
        50                  55                  60 ttg tct ctt cct cca cca cca aac aat gcc cgt ctc gtgagtcctt           716
Leu Ser Leu Pro Pro Pro Pro Asn Asn Ala Arg Leu
65                  70                  75 ttaattcact cattcaactt tcttggtttt gtgtgtctgc agatttatat acaagaatgg    776
tgacaatgca tatttagatt atcactttat gacttgttga atacttttt gtaacag        833 att gat gga cct gaa aag aat cag ttt tca cca atc tac aac aca aag      881
Ile Asp Gly Pro Glu Lys Asn Gln Phe Ser Pro Ile Tyr Asn Thr Lys
                80                  85                  90
```

-continued

```
ttt gag ggg aag ctg aat aaa aaa ggc ata aat tat aca agt cct aaa        929
Phe Glu Gly Lys Leu Asn Lys Lys Gly Ile Asn Tyr Thr Ser Pro Lys
         95                 100                 105 gga tca tca gtt act aat act aag cct agt tca ata aaa caa aat gag        977
Gly Ser Ser Val Thr Asn Thr Lys Pro Ser Ser Ile Lys Gln Asn Glu
    110                 115                 120 tac ctc aag aac ctt acc agc ttg gat tct att aag tct cct att gtt       1025
Tyr Leu Lys Asn Leu Thr Ser Leu Asp Ser Ile Lys Ser Pro Ile Val
125                 130                 135                 140 ata cac tca gaa ata gat cca caa gca aac aca gat ttg tca ctc caa       1073
Ile His Ser Glu Ile Asp Pro Gln Ala Asn Thr Asp Leu Ser Leu Gln
                145                 150                 155 ttt tgt act agc ggt agc agt aaa ccc gga gga gag gct gtt gtt ggt       1121
Phe Cys Thr Ser Gly Ser Ser Lys Pro Gly Gly Glu Ala Val Val Gly
            160                 165                 170 tct aag atc ctt ttg tca gaa cgt ttg gaa gat gaa aac cag aat ggg       1169
Ser Lys Ile Leu Leu Ser Glu Arg Leu Glu Asp Glu Asn Gln Asn Gly
        175                 180                 185 tct ccc aat gtg atg aaa act caa tca tat aga aga aac ttt gct gag       1217
Ser Pro Asn Val Met Lys Thr Gln Ser Tyr Arg Arg Asn Phe Ala Glu
    190                 195                 200 ttt aac aat gaa act caa aag aag ccc aaa act ctg cct cgg cgt gaa       1265
Phe Asn Asn Glu Thr Gln Lys Lys Pro Lys Thr Leu Pro Arg Arg Glu
205                 210                 215                 220 caa gtt gct tca aac tgc tct gca ata gag tct ttg tct ggt ata agt       1313
Gln Val Ala Ser Asn Cys Ser Ala Ile Glu Ser Leu Ser Gly Ile Ser
                225                 230                 235 gca tct tct tat gat att gcc aga gtg att ggt gaa aag agg ttt tgg       1361
Ala Ser Ser Tyr Asp Ile Ala Arg Val Ile Gly Glu Lys Arg Phe Trp
            240                 245                 250 aag atg aga aca tat atg atc aa gtttgtatcc tcctctcact tttcttatga      1414
Lys Met Arg Thr Tyr Met Ile Asn
        255                 260 tcccaacttc ataactttgc cgtatttctt actattttt attgttgata ttttcag t      1472 cag caa aag atc ttt gcc ggg caa gta ttt gag ctc cat aga ctg ata       1520
Gln Gln Lys Ile Phe Ala Gly Gln Val Phe Glu Leu His Arg Leu Ile
                265                 270                 275 atg gtaagctttt aataaccta ttgtttctgg tttgctttct atgcttcaga            1573
Met ttacttaata tgatgcag gtt caa aag atg gtt gcg aag tcg cca aac ttg       1624
                 Val Gln Lys Met Val Ala Lys Ser Pro Asn Leu
                             280                 285 ttt ctt gaa agt aag ctt aat ggt gtc aaa cat ggt aca atg agg tca       1672
Phe Leu Glu Ser Lys Leu Asn Gly Val Lys His Gly Thr Met Arg Ser
    290                 295                 300 tca cat cag ctt gca atg gcg gct tca aag gtt aga aag cca aac act       1720
Ser His Gln Leu Ala Met Ala Ala Ser Lys Val Arg Lys Pro Asn Thr
305                 310                 315                 320 gag aat cac aaa cct gta cct gaa gaa tat cca gag cat atg aaa cca       1768
Glu Asn His Lys Pro Val Pro Glu Glu Tyr Pro Glu His Met Lys Pro
                325                 330                 335 aag ctt cct cta cct tcc ata agc aaa gaa ctc gtg act cct att tgg       1816
Lys Leu Pro Leu Pro Ser Ile Ser Lys Glu Leu Val Thr Pro Ile Trp
            340                 345                 350 cca caa cag cta ctt cct cct cct gga aac caa tgg tta gtt cct gta       1864
Pro Gln Gln Leu Leu Pro Pro Pro Gly Asn Gln Trp Leu Val Pro Val
        355                 360                 365
```

-continued

```
ata act gat tca gac ggt ctg gtc tat aaa cca ttt cca gga cca tgt    1912
Ile Thr Asp Ser Asp Gly Leu Val Tyr Lys Pro Phe Pro Gly Pro Cys
        370                 375                 380 cct cct tct tct tca gcc ttc atg gtt cca gtt tat ggc caa gat tca    1960
Pro Pro Ser Ser Ser Ala Phe Met Val Pro Val Tyr Gly Gln Asp Ser
385                 390                 395                 400 ctc gag aca cca ttc agg ttc cct gtt tct tct cca ttc agc cac agc    2008
Leu Glu Thr Pro Phe Arg Phe Pro Val Ser Ser Pro Phe Ser His Ser
            405                 410                 415 tac ttc cca cct cct aac gcg agg aca aca gtt gac caa aca aac ccg    2056
Tyr Phe Pro Pro Pro Asn Ala Arg Thr Thr Val Asp Gln Thr Asn Pro
        420                 425                 430 ttt ggt cag ttt caa aga tgg tct aac aca tca agc cac atg aca caa    2104
Phe Gly Gln Phe Gln Arg Trp Ser Asn Thr Ser Ser His Met Thr Gln
    435                 440                 445 gcc att cca ttt tct tta aag aag tct cag gaa tct aat gac agt gac    2152
Ala Ile Pro Phe Ser Leu Lys Lys Ser Gln Glu Ser Asn Asp Ser Asp
450                 455                 460 ata cat gga agc aca gct tca agt cca cca gag aag cat aaa ctt gaa    2200
Ile His Gly Ser Thr Ala Ser Ser Pro Pro Glu Lys His Lys Leu Glu
465                 470                 475                 480 gtg ctt cct ctg ttt cct aca gag cct acc cat caa act gat gag tac    2248
Val Leu Pro Leu Phe Pro Thr Glu Pro Thr His Gln Thr Asp Glu Tyr
            485                 490                 495 aag cag aaa cag caa ccg atg ctt cgc gcc att aaa gcc gtt cct cat    2296
Lys Gln Lys Gln Gln Pro Met Leu Arg Ala Ile Lys Ala Val Pro His
        500                 505                 510 aat tca aca tct gcc tct gaa tct gct gca agg atc ttc cgt ttc att    2344
Asn Ser Thr Ser Ala Ser Glu Ser Ala Ala Arg Ile Phe Arg Phe Ile
    515                 520                 525 cag gaa gaa agg agg gac tca gat cat atg att agt tag ttcttttata    2393
Gln Glu Glu Arg Arg Asp Ser Asp His Met Ile Ser
530                 535                 540 tttgaaaccc ttccacattc ttttgctctc attgcttctt catctagctt agattttcag    2453
tatattctat ttactcttct tatgaagatg taaatcaaat actatcacta tacattaaac    2513
atacacacac ttatacacac atcttacatt gttcttgtat tgacaaacag ctaataaaag    2573
atagactttt gtgcttctat tccagttttg aggagtttaa acattggaac aagaagagtt    2633
ctttagccat tgaagtatct atattatcaa tgtggaagga gacaataagg atcagagttg    2693
tgtccatgct atacgaagct acactcaagt tcaagaacat tcagaacaa aaaccaagaa    2753 caaaagaag acaagagatc cattaattag aacccaagaa c                        2794

<210> SEQ ID NO 33
<211> LENGTH: 540
<212> TYPE: PRT
<213> ORGANISM: Arabidopsis thaliana

<400> SEQUENCE: 33

Met Gly Gly Met Lys Asp Glu Ala Lys Arg Ile Thr Ile Pro Pro Leu
1               5                   10                  15

Phe Pro Arg Val His Val Asn Asp Thr Gly Arg Gly Gly Leu Ser Gln
            20                  25                  30

Gln Phe Asp Gly Lys Thr Met Ser Leu Val Ser Ser Lys Arg Pro Asn
        35                  40                  45

Leu Pro Ser Pro Thr Asn Asn Ile Ser Asp Ser Leu Ser Thr Phe Ser
    50                  55                  60
```

```
Leu Ser Leu Pro Pro Pro Asn Asn Ala Arg Leu Ile Asp Gly Pro
 65                  70                  75                  80

Glu Lys Asn Gln Phe Ser Pro Ile Tyr Asn Thr Lys Phe Glu Gly Lys
                 85                  90                  95

Leu Asn Lys Lys Gly Ile Asn Tyr Thr Ser Pro Lys Gly Ser Ser Val
            100                 105                 110

Thr Asn Thr Lys Pro Ser Ser Ile Lys Gln Asn Glu Tyr Leu Lys Asn
            115                 120                 125

Leu Thr Ser Leu Asp Ser Ile Lys Ser Pro Ile Val Ile His Ser Glu
    130                 135                 140

Ile Asp Pro Gln Ala Asn Thr Asp Leu Ser Leu Gln Phe Cys Thr Ser
145                 150                 155                 160

Gly Ser Ser Lys Pro Gly Gly Glu Ala Val Val Gly Ser Lys Ile Leu
                165                 170                 175

Leu Ser Glu Arg Leu Glu Asp Glu Asn Gln Asn Gly Ser Pro Asn Val
            180                 185                 190

Met Lys Thr Gln Ser Tyr Arg Arg Asn Phe Ala Glu Phe Asn Asn Glu
            195                 200                 205

Thr Gln Lys Lys Pro Lys Thr Leu Pro Arg Arg Glu Gln Val Ala Ser
    210                 215                 220

Asn Cys Ser Ala Ile Glu Ser Leu Ser Gly Ile Ser Ala Ser Ser Tyr
225                 230                 235                 240

Asp Ile Ala Arg Val Ile Gly Glu Lys Arg Phe Trp Lys Met Arg Thr
                245                 250                 255

Tyr Met Ile Asn Gln Gln Lys Ile Phe Ala Gly Gln Val Phe Glu Leu
            260                 265                 270

His Arg Leu Ile Met Val Gln Lys Met Val Ala Lys Ser Pro Asn Leu
            275                 280                 285

Phe Leu Glu Ser Lys Leu Asn Gly Val Lys His Gly Thr Met Arg Ser
    290                 295                 300

Ser His Gln Leu Ala Met Ala Ala Ser Lys Val Arg Lys Pro Asn Thr
305                 310                 315                 320

Glu Asn His Lys Pro Val Pro Glu Glu Tyr Pro Glu His Met Lys Pro
                325                 330                 335

Lys Leu Pro Leu Pro Ser Ile Ser Lys Glu Leu Val Thr Pro Ile Trp
            340                 345                 350

Pro Gln Gln Leu Leu Pro Pro Gly Asn Gln Trp Leu Val Pro Val
            355                 360                 365

Ile Thr Asp Ser Asp Gly Leu Val Tyr Lys Pro Phe Pro Gly Pro Cys
    370                 375                 380

Pro Pro Ser Ser Ser Ala Phe Met Val Pro Val Tyr Gly Gln Asp Ser
385                 390                 395                 400

Leu Glu Thr Pro Phe Arg Phe Pro Val Ser Ser Pro Phe Ser His Ser
                405                 410                 415

Tyr Phe Pro Pro Pro Asn Ala Arg Thr Thr Val Asp Gln Thr Asn Pro
            420                 425                 430

Phe Gly Gln Phe Gln Arg Trp Ser Asn Thr Ser Ser His Met Thr Gln
            435                 440                 445

Ala Ile Pro Phe Ser Leu Lys Lys Ser Gln Glu Ser Asn Asp Ser Asp
    450                 455                 460

Ile His Gly Ser Thr Ala Ser Ser Pro Pro Glu Lys His Lys Leu Glu
465                 470                 475                 480
```

```
Val Leu Pro Leu Phe Pro Thr Glu Pro Thr His Gln Thr Asp Glu Tyr
            485                 490                 495

Lys Gln Lys Gln Gln Pro Met Leu Arg Ala Ile Lys Ala Val Pro His
        500                 505                 510

Asn Ser Thr Ser Ala Ser Glu Ser Ala Ala Arg Ile Phe Arg Phe Ile
        515                 520                 525

Gln Glu Glu Arg Arg Asp Ser Asp His Met Ile Ser
    530                 535                 540

<210> SEQ ID NO 34
<211> LENGTH: 4221
<212> TYPE: DNA
<213> ORGANISM: Arabidopsis thaliana
<220> FEATURE:
<221> NAME/KEY: 5'UTR
<222> LOCATION: (1)..(425)
<220> FEATURE:
<221> NAME/KEY: exon
<222> LOCATION: (426)..(644)
<220> FEATURE:
<221> NAME/KEY: Intron
<222> LOCATION: (645)..(1006)
<220> FEATURE:
<221> NAME/KEY: exon
<222> LOCATION: (1007)..(1803)
<220> FEATURE:
<221> NAME/KEY: Intron
<222> LOCATION: (1804)..(2983)
<220> FEATURE:
<221> NAME/KEY: exon
<222> LOCATION: (2984)..(3035)
<220> FEATURE:
<221> NAME/KEY: Intron
<222> LOCATION: (3036)..(3125)
<220> FEATURE:
<221> NAME/KEY: exon
<222> LOCATION: (3126)..(4145)
<220> FEATURE:
<221> NAME/KEY: 3'UTR
<222> LOCATION: (4146)..(4221)

<400> SEQUENCE: 34
tatctttggg ggctccactt ttcctatctc tttttgcccc tttcctctct ctgttcacaa      60
gtcatcttct tccttcctct gaatcttgtt ccttttttgct ctctctactt gattcaccca    120 ctctgttttct cgattagtac gttgaaaact cacttkggtt ttgtttgatt cctctttagt   180
ctgtttttcg atttcgttttt ctctgattgg tttggtggtg agatctctat cgtagtttgt   240
cctttgggtt aagatatttc atttgattgg tgggtttgtt ttattgaagc ttattgttgt   300
gaaagttgga gtctttctca gttttttaggt tgaattatta agagaaaggg aagattttg    360 gtgtgaagtt aggttatttg gggtttgaga agtttgcaag tgaaaaaggt tgtgaattgt   420 gagtg atg aag aga ggg aaa gat gag gag aag ata ttg gaa cct atg ttt    470
      Met Lys Arg Gly Lys Asp Glu Glu Lys Ile Leu Glu Pro Met Phe
      1               5                   10                  15 cct cgg ctt cat gtg aat gat gca gat aaa gga ggg cct aga gct cct    518
Pro Arg Leu His Val Asn Asp Ala Asp Lys Gly Gly Pro Arg Ala Pro
            20                  25                  30 cct aga aac aag atg gct ctt tat gag cag ctt agt att cct tct cag    566
Pro Arg Asn Lys Met Ala Leu Tyr Glu Gln Leu Ser Ile Pro Ser Gln
        35                  40                  45 agg ttt ggt gat cat gga acg atg aat tct cgt agt aac aac aca agc    614
Arg Phe Gly Asp His Gly Thr Met Asn Ser Arg Ser Asn Asn Thr Ser
    50                  55                  60
```

```
act ttg gtt cat cct gga cca tct agt cag gtattgtttt gattttgatc        664
Thr Leu Val His Pro Gly Pro Ser Ser Gln
     65                  70 attgtatagg ctcttgatgt tattagttgt atgagtttgg atgttatata gcctgaaaga    724
gaaagtagga cattggttga tctatgtttc aattgttatc agatcatagt atcttctttt    784
tgcttatgga ttgagctttt aggattgaat tctcctgtat atatgagagt cttgtagaca    844
caagtttatc taagtgtggt ttatttctta aaactaacat tcttgttgtg cctgattctt    904
tttatgttct gaagttcgat gaaagtttct tgtgattgcc ctgagcattc agactattgc    964
aaggacatga gaaataatcc tttttaccc tcttcaatgc ag cct tgt ggt gtg       1018
                                             Pro Cys Gly Val
                                                  75 gaa aga aac tta tct gtc cag cat ctt gat tct tca gcc gca aac caa     1066
Glu Arg Asn Leu Ser Val Gln His Leu Asp Ser Ser Ala Ala Asn Gln
         80                  85                  90 gca act gag aag ttt gtc tcc caa atg tcc ttc atg gaa aat gtg aga     1114
Ala Thr Glu Lys Phe Val Ser Gln Met Ser Phe Met Glu Asn Val Arg
 95                 100                 105 tct tcg gca cag cat gat cag agg aaa atg gtg aga gag gaa gaa gat     1162
Ser Ser Ala Gln His Asp Gln Arg Lys Met Val Arg Glu Glu Glu Asp
110                 115                 120                 125 ttt gca gtt cca gta tat att aac tca aga aga tct cag tct cat ggc     1210
Phe Ala Val Pro Val Tyr Ile Asn Ser Arg Arg Ser Gln Ser His Gly
                130                 135                 140 aga acc aag agt ggt att gag aag gaa aaa cac acc cca atg gtg gca     1258
Arg Thr Lys Ser Gly Ile Glu Lys Glu Lys His Thr Pro Met Val Ala
            145                 150                 155 cct agc tct cat cac tcc att cga ttt caa gaa gtg aat cag aca ggc     1306
Pro Ser Ser His His Ser Ile Arg Phe Gln Glu Val Asn Gln Thr Gly
        160                 165                 170 tca aag caa aac gta tgt ttg gct act tgt tca aaa cct gaa gtt agg     1354
Ser Lys Gln Asn Val Cys Leu Ala Thr Cys Ser Lys Pro Glu Val Arg
    175                 180                 185 gat cag gtc aag gcg aat gca agg tca ggt ggc ttt gta atc tct tta     1402
Asp Gln Val Lys Ala Asn Ala Arg Ser Gly Gly Phe Val Ile Ser Leu
190                 195                 200                 205 gat gta tca gtc aca gag gag att gat ctc gaa aaa tca gca tca agt     1450
Asp Val Ser Val Thr Glu Glu Ile Asp Leu Glu Lys Ser Ala Ser Ser
                210                 215                 220 cat gat aga gta aat gat tat aat gct tcc ttg aga caa gag tct aga     1498
His Asp Arg Val Asn Asp Tyr Asn Ala Ser Leu Arg Gln Glu Ser Arg
            225                 230                 235 aat cgg tta tac cga gat ggt ggc aaa act cgt ctg aag gac act gat     1546
Asn Arg Leu Tyr Arg Asp Gly Gly Lys Thr Arg Leu Lys Asp Thr Asp
        240                 245                 250 aat gga gct gaa tct cac ttg gca acg gaa aat cat tca caa gag ggt     1594
Asn Gly Ala Glu Ser His Leu Ala Thr Glu Asn His Ser Gln Glu Gly
    255                 260                 265 cat ggc agt cct gaa gac att gat aat gat cgt gaa tac agc aaa agc     1642
His Gly Ser Pro Glu Asp Ile Asp Asn Asp Arg Glu Tyr Ser Lys Ser
270                 275                 280                 285 aga gca tgc gcc tct ctg cag cag ata aat gaa gag gca agt gat gac     1690
Arg Ala Cys Ala Ser Leu Gln Gln Ile Asn Glu Glu Ala Ser Asp Asp
                290                 295                 300 gtt tct gat gat tcg atg gtg gat tct ata tcc agc ata gat gtc tct     1738
Val Ser Asp Asp Ser Met Val Asp Ser Ile Ser Ser Ile Asp Val Ser
            305                 310                 315
```

```
ccc gat gat gtt gtg ggt ata tta ggt caa aaa cgt ttc tgg aga gca    1786
Pro Asp Asp Val Val Gly Ile Leu Gly Gln Lys Arg Phe Trp Arg Ala
        320                 325                 330 agg aaa gcc att gcc aa gtaagttcac tagaaattta cagtttggtt            1833
Arg Lys Ala Ile Ala Asn
        335 atttattctc cgctctttct atttatctcc ttctttgata ccaacatttt ttgcttgaaa   1893 gaagttaata tttaagcatt gttccgtagt cttactgaag cttttcctc tgttgttttt   1953 tgctatttc attgaggact gtggtagggc atatttcact atcaccaaat ttcaaatttc   2013 tagaacactc tccttcatat ttttttcat gattaatgct gcaattgatt gctgatatac   2073 atatatgact ataactcagt ttcatattct gtctcatttt gggagaaaga gatttcaggt   2133 ttatgcttga gaagtgatgg ttctatagtt gagaggcccc tgattcatct aaaatggtcc   2193 tattatgtgt ttagttgtag agtcctcggt agaatattaa cgcgtttaac acgttggatc   2253 atgttatagc agggagggac attctctgtt gacctatatt gtgcaaggtg cccgccgatg   2313 gctttattac tataccttct ttgcatctgg ttgttggaac atgtccctgt ctcggtttgg   2373 tattgctttt attctgcact gtcgtcttgg gcatttccc tacttgtcat tcaaggggtt    2433 gaaccaggta gggaaatgtt tttccgagga ccccaggatc taaattttag ttaaccatac   2493 gtaaagttag ttttgagtct tatgacgatg cagaattata gtttcttctt actactgctt   2553 aagaggatcc ttagtgtggt tgtgaactac agagttttta tgattgtagg cttcatgact   2613 taacttttaa ggttcaatgt actctaatcc atatggtaag gtatcggatt cacgaccaat   2673 gcaaataata agattttat ttcttgcttc ttgttaaata tctgacatct cattttgcag    2733 aggataagct gcgctgtaag ctagatttca ataagcccgt cctttgcatt gttatctatg   2793 ctttaatatg tcattggacc cattgatttg gtttcttct atctttttg attggctatg     2853 tattcttgtt tcttttttcc tatctcattt cgatcgtatt gttccattag ctgttcaacc   2913 taaactatgt ctctctttgt tgaacttttg atggataatc ttcttaatgt gactctgttt   2973 ctcattacag t caa caa aga gta ttt gct gtt caa cta ttt gag ttg cac   3023
              Gln Gln Arg Val Phe Ala Val Gln Leu Phe Glu Leu His
                      340                 345                 350 aga ctg att aag gtaaagtcat tcagaaactt ctcatatgtt tccatgagta         3075
Arg Leu Ile Lys
    355 tttgttctt ctcgagctga aacaaacctc ttcaactgtg taataatcag gtt caa       3131
                                                        Val Gln aaa ctt att gct gca tca ccg gat ctc ttg ctc gat gag atc agt ttt    3179
Lys Leu Ile Ala Ala Ser Pro Asp Leu Leu Leu Asp Glu Ile Ser Phe
        360                 365                 370 ctt gga aaa gtt tct gct aaa agc tat cca gtg aag aag ctc ctt cca   3227
Leu Gly Lys Val Ser Ala Lys Ser Tyr Pro Val Lys Lys Leu Leu Pro
375                 380                 385                 390 tca gaa ttt ctg gta aag cct cct cta cca cat gtt gtc gtc aaa caa   3275
Ser Glu Phe Leu Val Lys Pro Pro Leu Pro His Val Val Val Lys Gln
                395                 400                 405 agg ggt gac tcg gag aag act gac caa cat aaa atg gaa agc tca gct   3323
Arg Gly Asp Ser Glu Lys Thr Asp Gln His Lys Met Glu Ser Ser Ala
        410                 415                 420 gag aac gta gtt ggg agg ttg tca aat caa ggt cat cat caa caa tcc   3371
Glu Asn Val Val Gly Arg Leu Ser Asn Gln Gly His His Gln Gln Ser
425                 430                 435
```

| | | | | | | | | | | | | |
|---|---|---|---|---|---|---|---|---|---|---|---|---|
| aac | tac | atg | cct | ttt | gca | aac | aac | cca | ccg | gct | tca | ccg | gct | cca | aat | 3419 |
| Asn | Tyr | Met | Pro | Phe | Ala | Asn | Asn | Pro | Pro | Ala | Ser | Pro | Ala | Pro | Asn | |
| | 440 | | | | | 445 | | | | | 450 | | | | | |

```
aac tac atg cct ttt gca aac aac cca ccg gct tca ccg gct cca aat      3419
Asn Tyr Met Pro Phe Ala Asn Asn Pro Pro Ala Ser Pro Ala Pro Asn
        440                 445                 450 gga tat tgc ttt cct cct cag cct cct cct tca gga aat cat cag caa      3467
Gly Tyr Cys Phe Pro Pro Gln Pro Pro Pro Ser Gly Asn His Gln Gln
455                 460                 465                 470 tgg ttg atc cct gta atg tct ccc tcg gaa gga ctg ata tac aag cct      3515
Trp Leu Ile Pro Val Met Ser Pro Ser Glu Gly Leu Ile Tyr Lys Pro
                475                 480                 485 cac cca ggt atg gca cac acg ggg cat tat gga gga tat tat ggt cat      3563
His Pro Gly Met Ala His Thr Gly His Tyr Gly Gly Tyr Tyr Gly His
        490                 495                 500 tat atg cct aca cca atg gta atg cct caa tat cac ccc ggc atg gga      3611
Tyr Met Pro Thr Pro Met Val Met Pro Gln Tyr His Pro Gly Met Gly
        505                 510                 515 ttc cca cct cct ggt aat ggc tac ttc cct cca tat gga atg atg ccc      3659
Phe Pro Pro Pro Gly Asn Gly Tyr Phe Pro Pro Tyr Gly Met Met Pro
520                 525                 530 acc ata atg aac cca tat tgt tca agc caa caa caa caa caa caa          3707
Thr Ile Met Asn Pro Tyr Cys Ser Ser Gln Gln Gln Gln Gln Gln
535                 540                 545                 550 ccc aat gag caa atg aac cag ttt gga cat cct gga aat ctt cag aac      3755
Pro Asn Glu Gln Met Asn Gln Phe Gly His Pro Gly Asn Leu Gln Asn
                555                 560                 565 acc caa caa caa caa cag aga tct gat aat gaa cct gct cca cag caa      3803
Thr Gln Gln Gln Gln Gln Arg Ser Asp Asn Glu Pro Ala Pro Gln Gln
        570                 575                 580 cag caa cag cca aca aag tct tat ccg cga gca aga aag agc agg caa      3851
Gln Gln Gln Pro Thr Lys Ser Tyr Pro Arg Ala Arg Lys Ser Arg Gln
585                 590                 595 ggg agc aca gga agc agt cca agt ggg cca cag gga atc tct ggt agc      3899
Gly Ser Thr Gly Ser Ser Pro Ser Gly Pro Gln Gly Ile Ser Gly Ser
600                 605                 610 aag tcc ttt cgg cca ttc gca gcc gtt gat gag gac agc aac atc aac      3947
Lys Ser Phe Arg Pro Phe Ala Ala Val Asp Glu Asp Ser Asn Ile Asn
615                 620                 625                 630 aat gca cct gag caa acg atg aca aca acc aca acg aca aga aca          3995
Asn Ala Pro Glu Gln Thr Met Thr Thr Thr Thr Thr Thr Arg Thr
                635                 640                 645 act gtt act cag aca aca aga gat ggg gga gga gtg acg aga gtg ata      4043
Thr Val Thr Gln Thr Thr Arg Asp Gly Gly Gly Val Thr Arg Val Ile
        650                 655                 660 aag gtg gta cct cac aac gca aag ctc gcg agt gag aat gct gcc aga      4091
Lys Val Val Pro His Asn Ala Lys Leu Ala Ser Glu Asn Ala Ala Arg
        665                 670                 675 att ttc cag tca ata caa gaa gaa cgt aaa cgc tat gac tcc tct aag      4139
Ile Phe Gln Ser Ile Gln Glu Glu Arg Lys Arg Tyr Asp Ser Ser Lys
680                 685                 690 cct taa tcctctctat gcgtattgta cttgatatgt attttacaaa attagaaaaa      4195
Pro
695 ttgtgataga tgttatcctc aatata                                         4221
```

<210> SEQ ID NO 35
<211> LENGTH: 695
<212> TYPE: PRT
<213> ORGANISM: Arabidopsis thaliana

<400> SEQUENCE: 35

-continued

```
Met Lys Arg Gly Lys Asp Glu Glu Lys Ile Leu Glu Pro Met Phe Pro
1               5                   10                  15

Arg Leu His Val Asn Asp Ala Asp Lys Gly Gly Pro Arg Ala Pro Pro
            20                  25                  30

Arg Asn Lys Met Ala Leu Tyr Glu Gln Leu Ser Ile Pro Ser Gln Arg
        35                  40                  45

Phe Gly Asp His Gly Thr Met Asn Ser Arg Ser Asn Asn Thr Ser Thr
    50                  55                  60

Leu Val His Pro Gly Pro Ser Ser Gln Pro Cys Gly Val Glu Arg Asn
65                  70                  75                  80

Leu Ser Val Gln His Leu Asp Ser Ser Ala Ala Asn Gln Ala Thr Glu
                85                  90                  95

Lys Phe Val Ser Gln Met Ser Phe Met Glu Asn Val Arg Ser Ser Ala
            100                 105                 110

Gln His Asp Gln Arg Lys Met Val Arg Glu Glu Asp Phe Ala Val
    115                 120                 125

Pro Val Tyr Ile Asn Ser Arg Ser Gln Ser His Gly Arg Thr Lys
130                 135                 140

Ser Gly Ile Glu Lys Glu Lys His Thr Pro Met Val Ala Pro Ser Ser
145                 150                 155                 160

His His Ser Ile Arg Phe Gln Glu Val Asn Gln Thr Gly Ser Lys Gln
                165                 170                 175

Asn Val Cys Leu Ala Thr Cys Ser Lys Pro Glu Val Arg Asp Gln Val
            180                 185                 190

Lys Ala Asn Ala Arg Ser Gly Gly Phe Val Ile Ser Leu Asp Val Ser
        195                 200                 205

Val Thr Glu Glu Ile Asp Leu Glu Lys Ser Ala Ser Ser His Asp Arg
    210                 215                 220

Val Asn Asp Tyr Asn Ala Ser Leu Arg Gln Glu Ser Arg Asn Arg Leu
225                 230                 235                 240

Tyr Arg Asp Gly Gly Lys Thr Arg Leu Lys Asp Thr Asp Asn Gly Ala
                245                 250                 255

Glu Ser His Leu Ala Thr Glu Asn His Ser Gln Glu Gly His Gly Ser
            260                 265                 270

Pro Glu Asp Ile Asp Asn Asp Arg Glu Tyr Ser Lys Ser Arg Ala Cys
        275                 280                 285

Ala Ser Leu Gln Gln Ile Asn Glu Glu Ala Ser Asp Val Ser Asp
    290                 295                 300

Asp Ser Met Val Asp Ser Ile Ser Ser Ile Asp Val Ser Pro Asp Asp
305                 310                 315                 320

Val Val Gly Ile Leu Gly Gln Lys Arg Phe Trp Arg Ala Arg Lys Ala
                325                 330                 335

Ile Ala Asn Gln Gln Arg Val Phe Ala Val Gln Leu Phe Glu Leu His
            340                 345                 350

Arg Leu Ile Lys Val Gln Lys Leu Ile Ala Ala Ser Pro Asp Leu Leu
        355                 360                 365

Leu Asp Glu Ile Ser Phe Leu Gly Lys Val Ser Ala Lys Ser Tyr Pro
    370                 375                 380

Val Lys Lys Leu Leu Pro Ser Glu Phe Leu Lys Pro Pro Leu Pro
385                 390                 395                 400

His Val Val Val Lys Gln Arg Gly Asp Ser Glu Lys Thr Asp Gln His
                405                 410                 415
```

```
Lys Met Glu Ser Ser Ala Glu Asn Val Val Gly Arg Leu Ser Asn Gln
            420                 425                 430

Gly His His Gln Gln Ser Asn Tyr Met Pro Phe Ala Asn Asn Pro Pro
            435                 440                 445

Ala Ser Pro Ala Pro Asn Gly Tyr Cys Phe Pro Pro Gln Pro Pro Pro
            450                 455                 460

Ser Gly Asn His Gln Gln Trp Leu Ile Pro Val Met Ser Pro Ser Glu
465                 470                 475                 480

Gly Leu Ile Tyr Lys Pro His Pro Gly Met Ala His Thr Gly His Tyr
            485                 490                 495

Gly Gly Tyr Tyr Gly His Tyr Met Pro Thr Pro Met Val Met Pro Gln
            500                 505                 510

Tyr His Pro Gly Met Gly Phe Pro Pro Gly Asn Gly Tyr Phe Pro
            515                 520                 525

Pro Tyr Gly Met Met Pro Thr Ile Met Asn Pro Tyr Cys Ser Ser Gln
            530                 535                 540

Gln Gln Gln Gln Gln Gln Pro Asn Glu Gln Met Asn Gln Phe Gly His
545                 550                 555                 560

Pro Gly Asn Leu Gln Asn Thr Gln Gln Gln Gln Arg Ser Asp Asn
            565                 570                 575

Glu Pro Ala Pro Gln Gln Gln Gln Pro Thr Lys Ser Tyr Pro Arg
            580                 585                 590

Ala Arg Lys Ser Arg Gln Gly Ser Thr Gly Ser Ser Pro Ser Gly Pro
            595                 600                 605

Gln Gly Ile Ser Gly Ser Lys Ser Phe Arg Pro Phe Ala Ala Val Asp
            610                 615                 620

Glu Asp Ser Asn Ile Asn Asn Ala Pro Glu Gln Thr Met Thr Thr Thr
625                 630                 635                 640

Thr Thr Thr Thr Arg Thr Thr Val Thr Gln Thr Thr Arg Asp Gly Gly
                    645                 650                 655

Gly Val Thr Arg Val Ile Lys Val Val Pro His Asn Ala Lys Leu Ala
            660                 665                 670

Ser Glu Asn Ala Ala Arg Ile Phe Gln Ser Ile Gln Glu Glu Arg Lys
            675                 680                 685

Arg Tyr Asp Ser Ser Lys Pro
            690                 695

<210> SEQ ID NO 36
<211> LENGTH: 510
<212> TYPE: DNA
<213> ORGANISM: Medicago truncatula
<220> FEATURE:
<221> NAME/KEY: 5'UTR
<222> LOCATION: (1)..(382)
<220> FEATURE:
<221> NAME/KEY: exon
<222> LOCATION: (383)..(508)
<220> FEATURE:
<221> NAME/KEY: misc_feature
<222> LOCATION: (414)..(414)
<223> OTHER INFORMATION: n = any nucleic acid
<220> FEATURE:
<221> NAME/KEY: misc_feature
<222> LOCATION: (427)..(427)
<223> OTHER INFORMATION: n = any nucleic acid

<400> SEQUENCE: 36
atccctaaac accctttctc tctaatccct aattttctc ctatctttct cttacaattt    60
```

```
gatttccttc ccatcataac ccctttttttg ctccgaattt ctcggttttt tgtttaaacc      120
aatttcctcc atcgattttg ataaattttt ttaatactac aaactataag caagatcaag      180 tatgaattt atgtttttct gatacccagt tgggaaaagt ttagattttg tgaattagtt       240
gtgttaatta gtgattagta tagttctgtg tatatgctat aatcactttt tatttttttgg    300 agttcaggat tataaactga ttctgttctt tgagtgtaat tattgatttg gttgatccat     360
agctgtatta ggaaggttaa gg atg aag aga ggg aat gat gat gag aaa gtg     412
                         Met Lys Arg Gly Asn Asp Asp Glu Lys Val
                         1               5                   10 ang ggg ccg tta ttn cct agg tta cat gtt ggt gat aca gag aag gga      460
Xaa Gly Pro Leu Xaa Pro Arg Leu His Val Gly Asp Thr Glu Lys Gly
            15                  20                  25 ggg cca aga gca cct cct agg aat aaa ttg gct ctc tat gag caa ttt      508
Gly Pro Arg Ala Pro Pro Arg Asn Lys Leu Ala Leu Tyr Glu Gln Phe
        30                  35                  40 aa                                                                    510
```

<210> SEQ ID NO 37
<211> LENGTH: 42
<212> TYPE: PRT
<213> ORGANISM: Medicago truncatula
<220> FEATURE:
<221> NAME/KEY: misc_feature
<222> LOCATION: (11)..(11)
<223> OTHER INFORMATION: Xaa = uncertain amino acid residue

<400> SEQUENCE: 37

```
Met Lys Arg Gly Asn Asp Asp Glu Lys Val Xaa Gly Pro Leu Phe Pro
1               5                   10                  15

Arg Leu His Val Gly Asp Thr Glu Lys Gly Gly Pro Arg Ala Pro Pro
            20                  25                  30

Arg Asn Lys Leu Ala Leu Tyr Glu Gln Phe
        35                  40
```

<210> SEQ ID NO 38
<211> LENGTH: 652
<212> TYPE: DNA
<213> ORGANISM: Medicago truncatula
<220> FEATURE:
<221> NAME/KEY: exon
<222> LOCATION: (2)..(106)
<220> FEATURE:
<221> NAME/KEY: misc_feature
<222> LOCATION: (7)..(7)
<223> OTHER INFORMATION: n = any nucleic acid
<220> FEATURE:
<221> NAME/KEY: 3'UTR
<222> LOCATION: (107)..(652)

<400> SEQUENCE: 38

```
c cga gtn atc aaa gtg gtg cct cat aac cga aga tcg gca act gaa tct    49
  Arg Val Ile Lys Val Val Pro His Asn Arg Arg Ser Ala Thr Glu Ser
  1               5                   10                  15 gca gct aga att ttc caa tca att caa gaa gag aga aaa caa tat gac       97
Ala Ala Arg Ile Phe Gln Ser Ile Gln Glu Glu Arg Lys Gln Tyr Asp
            20                  25                  30 aca ctc tag tgctgtttat tctcatggag gatccattca agtgtaaggt              146
Thr Leu gtctagttcc tgtactttct gcacgtgtgg catcgtgtaa aggtatatta tattatatat    206 atttttttgtt ttgaccttct tattttcagc acagtggtat gtagatatgt ctggcatatc   266
```

-continued

```
aaaattggtc aaaacatgat ctattgtacg ttatcctctt aagtacttgt acgtttctca      326
caggaatcga atcacaggaa aaagttagta gttctcagct ccgctcccct tgcttgggag      386 gaggttttg atcctatgta ctacttggct ttaaaattgg tgattgtcag tgttgggttt       446
tattctagtt ctattttgt tatttaatgt atgacaaatt ctatcttaaa caatttcgta       506
gcttgtgagg gggtgttaaa gtcttacaag gaagaggcat tgttagttat tggtcgagtc      566
aggaacttgt gaccaacaat tagttatcat cattattatt taaattata atcattcttt       626 tttttttttt tttgagcaaa attata                                          652
```

```
<210> SEQ ID NO 39
<211> LENGTH: 34
<212> TYPE: PRT
<213> ORGANISM: Medicago truncatula

<400> SEQUENCE: 39
```

Arg Val Ile Lys Val Val Pro His Asn Arg Arg Ser Ala Thr Glu Ser
1               5                   10                  15

Ala Ala Arg Ile Phe Gln Ser Ile Gln Glu Glu Arg Lys Gln Tyr Asp
            20                  25                  30

Thr Leu

```
<210> SEQ ID NO 40
<211> LENGTH: 368
<212> TYPE: DNA
<213> ORGANISM: Pisum sativum
<220> FEATURE:
<221> NAME/KEY: exon
<222> LOCATION: (1)..(12)
<220> FEATURE:
<221> NAME/KEY: Intron
<222> LOCATION: (13)..(92)
<220> FEATURE:
<221> NAME/KEY: exon
<222> LOCATION: (93)..(368)

<400> SEQUENCE: 40
``` cag act gat aaa ggtaaaatgg tcttactgag taattcaccc cctcaaagtt           52
Gln Thr Asp Lys
1 caaacatgtt catgccaagt aattcattta atttaaacag gtt caa cat ctg att       107
                                              Val Gln His Leu Ile
                                                          5 gct gaa tca tca aat ctt ttg ccc gat act gct gct gtt ttg gga aaa       155
Ala Glu Ser Ser Asn Leu Leu Pro Asp Thr Ala Ala Val Leu Gly Lys
10                  15                  20                  25 cct ctt ctg cag gga tct aat tct aaa agc ctt tca ttt gaa gaa gtt       203
Pro Leu Leu Gln Gly Ser Asn Ser Lys Ser Leu Ser Phe Glu Glu Val
                30                  35                  40 gtt gaa cct cag gca caa aat cat aaa cag caa gac cat tct gaa aac       251
Val Glu Pro Gln Ala Gln Asn His Lys Gln Gln Asp His Ser Glu Asn
            45                  50                  55 caa aac cat aaa ttg gat tat tct act gaa aat gga gtt ggg aaa aca       299
Gln Asn His Lys Leu Asp Tyr Ser Thr Glu Asn Gly Val Gly Lys Thr
        60                  65                  70 tcc tta tca tcc caa aaa tca aac cag gca aat gct ggt tca cag tgt       347
Ser Leu Ser Ser Gln Lys Ser Asn Gln Ala Asn Ala Gly Ser Gln Cys
75                  80                  85 ttt aat caa tca cct gga cat                                            368
Phe Asn Gln Ser Pro Gly His
90                  95

<210> SEQ ID NO 41
<211> LENGTH: 96
<212> TYPE: PRT
<213> ORGANISM: Pisum sativum

<400> SEQUENCE: 41

```
Arg Leu Ile Lys Val Gln His Leu Ile Ala Glu Ser Ser Asn Leu Leu
1               5                   10                  15

Pro Asp Thr Ala Ala Val Leu Gly Lys Pro Leu Leu Gln Gly Ser Asn
            20                  25                  30

Ser Lys Ser Leu Ser Phe Glu Glu Val Val Glu Pro Gln Ala Gln Asn
        35                  40                  45

His Lys Gln Gln Asp His Ser Glu Asn Gln Asn His Lys Leu Asp Tyr
    50                  55                  60

Ser Thr Glu Asn Gly Val Gly Lys Thr Ser Leu Ser Ser Gln Lys Ser
65                  70                  75                  80

Asn Gln Ala Asn Ala Gly Ser Gln Cys Phe Asn Gln Ser Pro Gly His
                85                  90                  95
```

<210> SEQ ID NO 42
<211> LENGTH: 523
<212> TYPE: DNA
<213> ORGANISM: Pisum sativum
<220> FEATURE:
<221> NAME/KEY: exon
<222> LOCATION: (2)..(523)
<223> OTHER INFORMATION: Partial

<400> SEQUENCE: 42

```
a tat ccc ggg cct gga ttt aca gga aca aat ttt gga gga tgt ggg ccc      49
  Tyr Pro Gly Pro Gly Phe Thr Gly Thr Asn Phe Gly Gly Cys Gly Pro
  1               5                   10                  15 tac gcg gct gct cct tcg ggt ggc act ttt atg aat cct tcc tat gga        97
Tyr Ala Ala Ala Pro Ser Gly Gly Thr Phe Met Asn Pro Ser Tyr Gly
            20                  25                  30 atc ccg cct cca cca gag act cct cca ggc agt caa gct tac ttc cct       145
Ile Pro Pro Pro Pro Glu Thr Pro Pro Gly Ser Gln Ala Tyr Phe Pro
        35                  40                  45 ccc tac ggt ggc atg cca gtt atg aaa gct gca gct tca gag tca gct       193
Pro Tyr Gly Gly Met Pro Val Met Lys Ala Ala Ala Ser Glu Ser Ala
    50                  55                  60 gtt gaa cat gtg aac caa ttc tcc gca cgc ggg caa agt cgt cgt tta       241
Val Glu His Val Asn Gln Phe Ser Ala Arg Gly Gln Ser Arg Arg Leu
65                  70                  75                  80 tct gaa gat gaa gct gat tgt aac aaa cac aat caa agc tca tac gat       289
Ser Glu Asp Glu Ala Asp Cys Asn Lys His Asn Gln Ser Ser Tyr Asp
                85                  90                  95 tta cca gtt cag aga aat gga gct aca tca cat gtc atg tat cat cag       337
Leu Pro Val Gln Arg Asn Gly Ala Thr Ser His Val Met Tyr His Gln
                100                 105                 110 aga tcc aag gag ttt gag gtg cag atg agt aca gca agt agt cct agc       385
Arg Ser Lys Glu Phe Glu Val Gln Met Ser Thr Ala Ser Ser Pro Ser
            115                 120                 125 gaa atg gca caa gaa atg agc acg gga caa gtt gcc gaa ggg aga gat       433
Glu Met Ala Gln Glu Met Ser Thr Gly Gln Val Ala Glu Gly Arg Asp
        130                 135                 140 gta cta cct ctt ttc cct atg gtt cca gta gaa cca gag agt gta cct       481
Val Leu Pro Leu Phe Pro Met Val Pro Val Glu Pro Glu Ser Val Pro
145                 150                 155                 160
```

```
cat tct ctc gaa aca gga caa aaa act cga gtt atc aaa gtg      523
His Ser Leu Glu Thr Gly Gln Lys Thr Arg Val Ile Lys Val
            165                 170
```

<210> SEQ ID NO 43
<211> LENGTH: 174
<212> TYPE: PRT
<213> ORGANISM: Pisum sativum

<400> SEQUENCE: 43

```
Tyr Pro Gly Pro Gly Phe Thr Gly Thr Asn Phe Gly Gly Cys Gly Pro
1               5                   10                  15

Tyr Ala Ala Ala Pro Ser Gly Gly Thr Phe Met Asn Pro Ser Tyr Gly
            20                  25                  30

Ile Pro Pro Pro Glu Thr Pro Gly Ser Gln Ala Tyr Phe Pro
        35                  40                  45

Pro Tyr Gly Gly Met Pro Val Met Lys Ala Ala Ser Glu Ser Ala
    50                  55                  60

Val Glu His Val Asn Gln Phe Ser Ala Arg Gly Gln Ser Arg Arg Leu
65              70                  75                  80

Ser Glu Asp Glu Ala Asp Cys Asn Lys His Asn Gln Ser Ser Tyr Asp
                85                  90                  95

Leu Pro Val Gln Arg Asn Gly Ala Thr Ser His Val Met Tyr His Gln
                100                 105                 110

Arg Ser Lys Glu Phe Glu Val Gln Met Ser Thr Ala Ser Ser Pro Ser
            115                 120                 125

Glu Met Ala Gln Glu Met Ser Thr Gly Gln Val Ala Glu Gly Arg Asp
        130                 135                 140

Val Leu Pro Leu Phe Pro Met Val Pro Val Glu Pro Glu Ser Val Pro
145                 150                 155                 160

His Ser Leu Glu Thr Gly Gln Lys Thr Arg Val Ile Lys Val
                165                 170
```

<210> SEQ ID NO 44
<211> LENGTH: 395
<212> TYPE: DNA
<213> ORGANISM: Glycine max
<220> FEATURE:
<221> NAME/KEY: Intron
<222> LOCATION: (1)..(301)
<223> OTHER INFORMATION: partial
<220> FEATURE:
<221> NAME/KEY: exon
<222> LOCATION: (302)..(395)
<223> OTHER INFORMATION: partial

<400> SEQUENCE: 44

```
ttatgtcttg ttaatatgtc gagtcctcct gaaaaaacca tgttaagatt tgtatgatga    60
tatgatataa attgtagaac ggaagatatt ccgcttaact gctaaccggt tttgtgatgt   120
gatcggagcc tctgattttg gtagttagtg gtttatatat cggtgcttcc atgttccaac   180
atgattatag atagctccaa acgcttaata tttccctttt atttcaactg tatatttctc   240
aagtcctaat aggacgagta ttgtgcaatt ttcttgatcc aactcctgtt cctctctaca   300 g tca aca gag agt gtt tgc tgt cca agt gtt tga gtt gca tag act gat  349
  Ser Thr Glu Ser Val Cys Cys Pro Ser Val     Val Ala     Thr Asp
  1               5                   10 aaa ggt cca aca gct aat tgc tgg atc acc aga tat ttt gct tga a     395
Lys Gly Pro Thr Ala Asn Cys Trp Ile Thr Arg Tyr Phe Ala
15                  20                  25
```

<210> SEQ ID NO 45
<211> LENGTH: 31
<212> TYPE: PRT
<213> ORGANISM: Glycine max

<400> SEQUENCE: 45

Gln Gln Arg Val Phe Ala Val Gln Val Phe Glu Leu His Arg Leu Ile
1               5                   10                  15

Lys Val Gln Gln Leu Ile Ala Gly Ser Pro Asp Ile Leu Leu Glu
            20                  25                  30

<210> SEQ ID NO 46
<211> LENGTH: 477
<212> TYPE: DNA
<213> ORGANISM: Xanthium
<220> FEATURE:
<221> NAME/KEY: exon
<222> LOCATION: (2)..(13)
<223> OTHER INFORMATION: partial
<220> FEATURE:
<221> NAME/KEY: Intron
<222> LOCATION: (14)..(144)
<223> OTHER INFORMATION: partial
<220> FEATURE:
<221> NAME/KEY: exon
<222> LOCATION: (145)..(477)
<223> OTHER INFORMATION: partial

<400> SEQUENCE: 46

```
t cga cta ata rag gtaaagcaac tccaaaggct gaatctcttg tagcaatttg          53
  Arg Leu Ile Xaa
  1 gggggagggt gtgaaataga aaatatgatc tatatactgt ttttcgattc attactacgc    113 tgctcatgca ttttcctgt tatttttaaca g gtc cag aag ctc att gcc gag       165
                                   Val Gln Lys Leu Ile Ala Glu
                                    5                  10 tca cca aac agt atg ctt gaa gat gct gct tat tta ggc aaa cca tta     213
Ser Pro Asn Ser Met Leu Glu Asp Ala Ala Tyr Leu Gly Lys Pro Leu
            15                  20                  25 aag agt tcg tct ggt aaa aga ctg cca ttg gag tgt att att aga gaa     261
Lys Ser Ser Ser Gly Lys Arg Leu Pro Leu Glu Cys Ile Ile Arg Glu
            30                  35                  40 tct caa agt gtt ccg aag cgc aag aat gat tct gag aag cct aac ttc     309
Ser Gln Ser Val Pro Lys Arg Lys Asn Asp Ser Glu Lys Pro Asn Phe
        45                  50                  55 agg atg gaa tgc tct gct gaa aac act gtg ggg aag gca tct ctt tct     357
Arg Met Glu Cys Ser Ala Glu Asn Thr Val Gly Lys Ala Ser Leu Ser
60                  65                  70                  75 tct gtg caa aac agt agc cag ctc tct agc cac aga cca ttt tca gga     405
Ser Val Gln Asn Ser Ser Gln Leu Ser Ser His Arg Pro Phe Ser Gly
                80                  85                  90 aat ccc cca cca acg cct gtg aca aac gat gct aac acg agt ccc tgg     453
Asn Pro Pro Pro Thr Pro Val Thr Asn Asp Ala Asn Thr Ser Pro Trp
            95                  100                 105 tgc ttt caa caa cct ccg ggg cac                                      477
Cys Phe Gln Gln Pro Pro Gly His
        110                 115
```

<210> SEQ ID NO 47
<211> LENGTH: 115
<212> TYPE: PRT
<213> ORGANISM: Xanthium
<220> FEATURE:

```
<221> NAME/KEY: misc_feature
<222> LOCATION: (4)..(4)
<223> OTHER INFORMATION: Xaa = uncertain amino acid residue

<400> SEQUENCE: 47

Arg Leu Ile Xaa Val Gln Lys Leu Ile Ala Glu Ser Pro Asn Ser Met
1               5                   10                  15

Leu Glu Asp Ala Ala Tyr Leu Gly Lys Pro Leu Lys Ser Ser Ser Gly
            20                  25                  30

Lys Arg Leu Pro Leu Glu Cys Ile Ile Arg Glu Ser Gln Ser Val Pro
        35                  40                  45

Lys Arg Lys Asn Asp Ser Glu Lys Pro Asn Phe Arg Met Glu Cys Ser
50                  55                  60

Ala Glu Asn Thr Val Gly Lys Ala Ser Leu Ser Ser Val Gln Asn Ser
65                  70                  75                  80

Ser Gln Leu Ser Ser His Arg Pro Phe Ser Gly Asn Pro Pro Thr
            85                  90                  95

Pro Val Thr Asn Asp Ala Asn Thr Ser Pro Trp Cys Phe Gln Gln Pro
            100                 105                 110

Pro Gly His
        115

<210> SEQ ID NO 48
<211> LENGTH: 433
<212> TYPE: DNA
<213> ORGANISM: Xanthium
<220> FEATURE:
<221> NAME/KEY: exon
<222> LOCATION: (2)..(13)
<223> OTHER INFORMATION: partial
<220> FEATURE:
<221> NAME/KEY: Intron
<222> LOCATION: (14)..(127)
<223> OTHER INFORMATION: partial
<220> FEATURE:
<221> NAME/KEY: exon
<222> LOCATION: (128)..(433)
<223> OTHER INFORMATION: partial

<400> SEQUENCE: 48 t mga cta ctc rag gtaaagcaac tgtagagact gaataacttc aattatcagc        53
  Xaa Leu Leu Xaa
  1 tttgagattt tgcattccct gttttccct ggacttggta ttttgctcaa attttctgt     113 ttgttactca ttag gtc cag aaa ctg ata gct agt tcg cca aat agt ata      163
               Val Gln Lys Leu Ile Ala Ser Ser Pro Asn Ser Ile
                5                   10                  15 ctc gaa gat ggt tct tct tta ggc aaa cct tta aag agg ttg tct act      211
Leu Glu Asp Gly Ser Ser Leu Gly Lys Pro Leu Lys Arg Leu Ser Thr
            20                  25                  30 aaa aga ctt gca ttg gag tat aat gtc aaa gca cct gaa aat gtt tcg      259
Lys Arg Leu Ala Leu Glu Tyr Asn Val Lys Ala Pro Glu Asn Val Ser
        35                  40                  45 aaa cag aag aat gat tct gag aag cct aac tct agg atg gaa tcc aat      307
Lys Gln Lys Asn Asp Ser Glu Lys Pro Asn Ser Arg Met Glu Ser Asn
50                  55                  60 gcc gaa aat gat gta gga gag aca tct ctt tct tgc cgc aga cca ctt      355
Ala Glu Asn Asp Val Gly Glu Thr Ser Leu Ser Cys Arg Arg Pro Leu
65                  70                  75                  80 tca gaa acc ccg tca cca aca cca gta aaa cac gtt tcc cac atg ggt      403
Ser Glu Thr Pro Ser Pro Thr Pro Val Lys His Val Ser His Met Gly
            85                  90                  95
```

```
ccg tgg ctc ttc aat caa cct tcg gga cac                           433
Pro Trp Leu Phe Asn Gln Pro Ser Gly His
        100                     105
```

<210> SEQ ID NO 49
<211> LENGTH: 106
<212> TYPE: PRT
<213> ORGANISM: Xanthium
<220> FEATURE:
<221> NAME/KEY: misc_feature
<222> LOCATION: (4)..(4)
<223> OTHER INFORMATION: Xaa = uncertain amino acid residue

<400> SEQUENCE: 49

```
Arg Leu Leu Xaa Val Gln Lys Leu Ile Ala Ser Ser Pro Asn Ser Ile
1               5                   10                  15

Leu Glu Asp Gly Ser Ser Leu Gly Lys Pro Leu Lys Arg Leu Ser Thr
            20                  25                  30

Lys Arg Leu Ala Leu Glu Tyr Asn Val Lys Ala Pro Glu Asn Val Ser
        35                  40                  45

Lys Gln Lys Asn Asp Ser Glu Lys Pro Asn Ser Arg Met Glu Ser Asn
    50                  55                  60

Ala Glu Asn Asp Val Gly Glu Thr Ser Leu Ser Cys Arg Arg Pro Leu
65                  70                  75                  80

Ser Glu Thr Pro Ser Pro Thr Pro Val Lys His Val Ser His Met Gly
                85                  90                  95

Pro Trp Leu Phe Asn Gln Pro Ser Gly His
            100                 105
```

<210> SEQ ID NO 50
<211> LENGTH: 526
<212> TYPE: DNA
<213> ORGANISM: Xanthium
<220> FEATURE:
<221> NAME/KEY: exon
<222> LOCATION: (2)..(526)
<223> OTHER INFORMATION: partial

<400> SEQUENCE: 50

```
a cat cct gga cct gca ttc atg agt cca gta tat ggc ggt tgt gga ccc    49
  His Pro Gly Pro Ala Phe Met Ser Pro Val Tyr Gly Gly Cys Gly Pro
  1               5                   10                  15 ccg att cca atg acg gga aac ttt tta gct ccg gca tac tat caa gga      97
Pro Ile Pro Met Thr Gly Asn Phe Leu Ala Pro Ala Tyr Tyr Gln Gly
            20                  25                  30 acg gga gct cct ttc gca cct caa cct agt cat ggc tac ttt cct ccg     145
Thr Gly Ala Pro Phe Ala Pro Gln Pro Ser His Gly Tyr Phe Pro Pro
        35                  40                  45 ttt gac atg cca gtt atg aat cca gta atc cca tct cca gct att gat     193
Phe Asp Met Pro Val Met Asn Pro Val Ile Pro Ser Pro Ala Ile Asp
    50                  55                  60 caa ccg gac cag gtt gct gca acg ggt ttt caa ggt ctg tta tcg aga     241
Gln Pro Asp Gln Val Ala Ala Thr Gly Phe Gln Gly Leu Leu Ser Arg
65                  70                  75                  80 gat cag gaa gtt aat ttt cac att caa caa cag aac tca agt aat gtt     289
Asp Gln Glu Val Asn Phe His Ile Gln Gln Gln Asn Ser Ser Asn Val
                85                  90                  95 gcg aga gag aat aat gta gcc gcg cca aag gtt gtg aga ttg tat ccc     337
Ala Arg Glu Asn Asn Val Ala Ala Pro Lys Val Val Arg Leu Tyr Pro
            100                 105                 110
```

```
tct aga gat tct gag ttg caa gcc agc act gca agt agt cca agg gaa        385
Ser Arg Asp Ser Glu Leu Gln Ala Ser Thr Ala Ser Ser Pro Arg Glu
        115                 120                 125 aga ggt cat gga tta gac gtg ggc aac tcc acc gga gga aga agc gtg        433
Arg Gly His Gly Leu Asp Val Gly Asn Ser Thr Gly Gly Arg Ser Val
    130                 135                 140 ttt cct ctg ttc cca act ttt cct gct att agc aac ccc gct agt agc        481
Phe Pro Leu Phe Pro Thr Phe Pro Ala Ile Ser Asn Pro Ala Ser Ser
145                 150                 155                 160 tcc cag cct cat ttt cct agt cat acg gct aga gtt atc aaa gtt            526
Ser Gln Pro His Phe Pro Ser His Thr Ala Arg Val Ile Lys Val
                165                 170                 175

<210> SEQ ID NO 51
<211> LENGTH: 175
<212> TYPE: PRT
<213> ORGANISM: Xanthium

<400> SEQUENCE: 51

His Pro Gly Pro Ala Phe Met Ser Pro Val Tyr Gly Gly Cys Gly Pro
1               5                   10                  15

Pro Ile Pro Met Thr Gly Asn Phe Leu Ala Pro Ala Tyr Tyr Gln Gly
            20                  25                  30

Thr Gly Ala Pro Phe Ala Pro Gln Pro Ser His Gly Tyr Phe Pro Pro
        35                  40                  45

Phe Asp Met Pro Val Met Asn Pro Val Ile Pro Ser Pro Ala Ile Asp
    50                  55                  60

Gln Pro Asp Gln Val Ala Ala Thr Gly Phe Gln Gly Leu Leu Ser Arg
65                  70                  75                  80

Asp Gln Glu Val Asn Phe His Ile Gln Gln Gln Asn Ser Ser Asn Val
                85                  90                  95

Ala Arg Glu Asn Asn Val Ala Ala Pro Lys Val Val Arg Leu Tyr Pro
            100                 105                 110

Ser Arg Asp Ser Glu Leu Gln Ala Ser Thr Ala Ser Ser Pro Arg Glu
        115                 120                 125

Arg Gly His Gly Leu Asp Val Gly Asn Ser Thr Gly Gly Arg Ser Val
    130                 135                 140

Phe Pro Leu Phe Pro Thr Phe Pro Ala Ile Ser Asn Pro Ala Ser Ser
145                 150                 155                 160

Ser Gln Pro His Phe Pro Ser His Thr Ala Arg Val Ile Lys Val
                165                 170                 175

<210> SEQ ID NO 52
<211> LENGTH: 532
<212> TYPE: DNA
<213> ORGANISM: poplar trees
<220> FEATURE:
<221> NAME/KEY: exon
<222> LOCATION: (2)..(532)
<223> OTHER INFORMATION: partial

<400> SEQUENCE: 52 t tac act gcc cck gga ttc atg gga tcg ggt tgt gga gga tgt gga cct      49
  Tyr Thr Ala Xaa Gly Phe Met Gly Ser Gly Cys Gly Gly Cys Gly Pro
  1               5                   10                  15 ttt ggg cca att ccc ttg aca gac aac ttt atg act tca gct tat gcg       97
Phe Gly Pro Ile Pro Leu Thr Asp Asn Phe Met Thr Ser Ala Tyr Ala
            20                  25                  30
```

```
att cca aca tct cat tat cat caa ggt att ggg gtc tca cca ggt gct         145
Ile Pro Thr Ser His Tyr His Gln Gly Ile Gly Val Ser Pro Gly Ala
         35                  40                  45 cct cca gtt ggt aat gct tgc ttc gcc cca tat ggc atg cca gga atg         193
Pro Pro Val Gly Asn Ala Cys Phe Ala Pro Tyr Gly Met Pro Gly Met
 50                  55                  60 aac cca gcc atc tca ggt tct gca ggg tct ggt tcc tgt ggt caa act         241
Asn Pro Ala Ile Ser Gly Ser Ala Gly Ser Gly Ser Cys Gly Gln Thr
 65                  70                  75                  80 gct cag ttt cca gga ggc att ttg agc tcg aac atg cca cat caa agc         289
Ala Gln Phe Pro Gly Gly Ile Leu Ser Ser Asn Met Pro His Gln Ser
             85                  90                  95 tca tgt aat gaa cgg act caa aag agt gaa gct gtt tta gaa ggt atg         337
Ser Cys Asn Glu Arg Thr Gln Lys Ser Glu Ala Val Leu Glu Gly Met
        100                 105                 110 aag ctt cgg gca tct aaa aac act tcg gta caa gga agt aca ggt agt         385
Lys Leu Arg Ala Ser Lys Asn Thr Ser Val Gln Gly Ser Thr Gly Ser
        115                 120                 125 agt ccc agt ggc aga gtg caa ggg gtt ggg act gtt caa gcc gct gat         433
Ser Pro Ser Gly Arg Val Gln Gly Val Gly Thr Val Gln Ala Ala Asp
130                 135                 140 gga aga gct gcg ttc cca cct ttc cca gtg act cct cct tgc cct gag         481
Gly Arg Ala Ala Phe Pro Pro Phe Pro Val Thr Pro Pro Cys Pro Glu
145                 150                 155                 160 gga gcc cct cag cat caa gag aca gac cag ctg tcg aaa gtg atc aag         529
Gly Ala Pro Gln His Gln Glu Thr Asp Gln Leu Ser Lys Val Ile Lys
                165                 170                 175 gtt                                                                     532
Val

<210> SEQ ID NO 53
<211> LENGTH: 177
<212> TYPE: PRT
<213> ORGANISM: Poplar trees
<220> FEATURE:
<221> NAME/KEY: misc_feature
<222> LOCATION: (4)..(4)
<223> OTHER INFORMATION: Xaa = uncertain amino acid residue

<400> SEQUENCE: 53

Tyr Thr Ala Xaa Gly Phe Met Gly Ser Gly Cys Gly Cys Gly Pro
  1               5                  10                  15

Phe Gly Pro Ile Pro Leu Thr Asp Asn Phe Met Thr Ser Ala Tyr Ala
             20                  25                  30

Ile Pro Thr Ser His Tyr His Gln Gly Ile Gly Val Ser Pro Gly Ala
         35                  40                  45

Pro Pro Val Gly Asn Ala Cys Phe Ala Pro Tyr Gly Met Pro Gly Met
 50                  55                  60

Asn Pro Ala Ile Ser Gly Ser Ala Gly Ser Gly Ser Cys Gly Gln Thr
 65                  70                  75                  80

Ala Gln Phe Pro Gly Gly Ile Leu Ser Ser Asn Met Pro His Gln Ser
             85                  90                  95

Ser Cys Asn Glu Arg Thr Gln Lys Ser Glu Ala Val Leu Glu Gly Met
        100                 105                 110

Lys Leu Arg Ala Ser Lys Asn Thr Ser Val Gln Gly Ser Thr Gly Ser
        115                 120                 125

Ser Pro Ser Gly Arg Val Gln Gly Val Gly Thr Val Gln Ala Ala Asp
130                 135                 140
```

```
Gly Arg Ala Ala Phe Pro Pro Phe Pro Val Thr Pro Pro Cys Pro Glu
145                 150                 155                 160

Gly Ala Pro Gln His Gln Glu Thr Asp Gln Leu Ser Lys Val Ile Lys
                165                 170                 175

Val

<210> SEQ ID NO 54
<211> LENGTH: 418
<212> TYPE: DNA
<213> ORGANISM: Mimulus sp.
<220> FEATURE:
<221> NAME/KEY: exon
<222> LOCATION: (2)..(418)

<400> SEQUENCE: 54 g tac ccg ttc gtc agc caa ccc tgt gga ggg ggc tgc ggc ccc cct gga      49
  Tyr Pro Phe Val Ser Gln Pro Cys Gly Gly Gly Cys Gly Pro Pro Gly
   1               5                  10                  15 tcg aat cca acg gtg gga aat ttc tca act cca cca ccg cca caa tat      97
Ser Asn Pro Thr Val Gly Asn Phe Ser Thr Pro Pro Pro Pro Gln Tyr
             20                  25                  30 cat cat tta cct tct ttc cct cag ttc ccc ccc cac ggc tac ttc cct      145
His His Leu Pro Ser Phe Pro Gln Phe Pro Pro His Gly Tyr Phe Pro
         35                  40                  45 cct tac tgt gtc ccg att atg gac acg tca gca ttc tcg ggc ccg ccc      193
Pro Tyr Cys Val Pro Ile Met Asp Thr Ser Ala Phe Ser Gly Pro Pro
     50                  55                  60 ccc gaa cag acc ata cga gcc cca gct gct gca ggc cca gct gta caa      241
Pro Glu Gln Thr Ile Arg Ala Pro Ala Ala Ala Gly Pro Ala Val Gln
 65                  70                  75                  80 aaa agc ggg ccc gct tta tgg gat gtc gaa atg caa ggg agc aca gct      289
Lys Ser Gly Pro Ala Leu Trp Asp Val Glu Met Gln Gly Ser Thr Ala
                 85                  90                  95 agt agc ccg agt ggg agg cgt aaa aga gga agc aac ggt gtt gaa ttt      337
Ser Ser Pro Ser Gly Arg Arg Lys Arg Gly Ser Asn Gly Val Glu Phe
            100                 105                 110 gaa aga agg aat atg ctt ccg ctt ttc ccc act acc cca gct gct gtg      385
Glu Arg Arg Asn Met Leu Pro Leu Phe Pro Thr Thr Pro Ala Ala Val
        115                 120                 125 gat gcc ttg aaa cca acg cgg gtg att aag gtt                          418
Asp Ala Leu Lys Pro Thr Arg Val Ile Lys Val
    130                 135

<210> SEQ ID NO 55
<211> LENGTH: 139
<212> TYPE: PRT
<213> ORGANISM: Mimulus sp.

<400> SEQUENCE: 55

Tyr Pro Phe Val Ser Gln Pro Cys Gly Gly Gly Cys Gly Pro Pro Gly
 1               5                  10                  15

Ser Asn Pro Thr Val Gly Asn Phe Ser Thr Pro Pro Pro Pro Gln Tyr
             20                  25                  30

His His Leu Pro Ser Phe Pro Gln Phe Pro Pro His Gly Tyr Phe Pro
         35                  40                  45

Pro Tyr Cys Val Pro Ile Met Asp Thr Ser Ala Phe Ser Gly Pro Pro
     50                  55                  60

Pro Glu Gln Thr Ile Arg Ala Pro Ala Ala Ala Gly Pro Ala Val Gln
 65                  70                  75                  80
```

```
Lys Ser Gly Pro Ala Leu Trp Asp Val Glu Met Gln Gly Ser Thr Ala
                85                  90                  95

Ser Ser Pro Ser Gly Arg Arg Lys Arg Gly Ser Asn Gly Val Glu Phe
            100                 105                 110

Glu Arg Arg Asn Met Leu Pro Leu Phe Pro Thr Thr Pro Ala Ala Val
        115                 120                 125

Asp Ala Leu Lys Pro Thr Arg Val Ile Lys Val
    130                 135

<210> SEQ ID NO 56
<211> LENGTH: 1272
<212> TYPE: DNA
<213> ORGANISM: Zea mays
<220> FEATURE:
<221> NAME/KEY: exon
<222> LOCATION: (3)..(185)
<223> OTHER INFORMATION: partial
<220> FEATURE:
<221> NAME/KEY: Intron
<222> LOCATION: (186)..(295)
<220> FEATURE:
<221> NAME/KEY: exon
<222> LOCATION: (296)..(1066)
<220> FEATURE:
<221> NAME/KEY: 3'UTR
<222> LOCATION: (1067)..(1272)

<400> SEQUENCE: 56 at gac gtg gag caa aac gat gat ctg tct gat tcc tct gtt gaa tct        47
   Asp Val Glu Gln Asn Asp Asp Leu Ser Asp Ser Ser Val Glu Ser
    1               5                  10                  15 ttg cct gga atg gag att tct cca gat gat gtt gtc agt gct att ggt       95
Leu Pro Gly Met Glu Ile Ser Pro Asp Asp Val Val Ser Ala Ile Gly
                20                  25                  30 ccc aag cat ttt tgg aaa gcg aga aga gct att gtc aat cag cag agg      143
Pro Lys His Phe Trp Lys Ala Arg Arg Ala Ile Val Asn Gln Gln Arg
             35                  40                  45 gta ttt gct gtt caa gta ttc gag ctg cat agg ttg atc aaa              185
Val Phe Ala Val Gln Val Phe Glu Leu His Arg Leu Ile Lys
         50                  55                  60 gtgagtctgc ggcaaataaa tataacttct ttgggcccat gcttatgggc aggttaattt    245
aaatttgaaa awttggttta acsgttgttt atgttgactt ttgcaatcag gtg cag      301
                                                       Val Gln aag ttg atc gct gca tct cca cat gta ctt att gag ggg gat cct tgc     349
Lys Leu Ile Ala Ala Ser Pro His Val Leu Ile Glu Gly Asp Pro Cys
 65                  70                  75 ctt ggc aaa tcc ttg gcg gtg agc aag aaa agg ctg gct gga gat gtg     397
Leu Gly Lys Ser Leu Ala Val Ser Lys Lys Arg Leu Ala Gly Asp Val
 80                  85                  90                  95 gaa aca cag ctt gaa tca gct aaa aac gat gat ggc gtg cga cca acg     445
Glu Thr Gln Leu Glu Ser Ala Lys Asn Asp Asp Gly Val Arg Pro Thr
                100                 105                 110 cag cta gag cac tcg aaa gag aag act gaa gcg aac caa cct tca cca     493
Gln Leu Glu His Ser Lys Glu Lys Thr Glu Ala Asn Gln Pro Ser Pro
            115                 120                 125 tct caa gac gaa cag gcc gca act aat ggt gac gtt gct gcc ttg atg     541
Ser Gln Asp Glu Gln Ala Ala Thr Asn Gly Asp Val Ala Ala Leu Met
        130                 135                 140 cat acc cct tcc gac aac aaa cag aag agc tgg tgc att cct gca cct     589
His Thr Pro Ser Asp Asn Lys Gln Lys Ser Trp Cys Ile Pro Ala Pro
    145                 150                 155
```

| | | |
|---|---|---|
| cca agt cag tgg ctg att cct gtw atg tcc ccg tct gaa gga ctt gtc<br>Pro Ser Gln Trp Leu Ile Pro Xaa Met Ser Pro Ser Glu Gly Leu Val<br>160 165 170 175 | | 637 |
| tac aag cct tat acc ggg cac tgc cct ccg gtg gga agt ctt ttg gcg<br>Tyr Lys Pro Tyr Thr Gly His Cys Pro Pro Val Gly Ser Leu Leu Ala<br>180 185 190 | | 685 |
| ccc cca ttt ttt gcc agc tac ccc acc tcc tcc tcc aca gct ggg<br>Pro Pro Phe Phe Ala Ser Tyr Pro Thr Ser Ser Ser Thr Ala Gly<br>195 200 205 | | 733 |
| ggg gat ttc atg agt tcg gca tgt gga gcc agg ctg atg agt gcc cct<br>Gly Asp Phe Met Ser Ser Ala Cys Gly Ala Arg Leu Met Ser Ala Pro<br>210 215 220 | | 781 |
| gtg tac ttc ccg tct ttc agc atg cct gca gtg tca ggg tct gca gtt<br>Val Tyr Phe Pro Ser Phe Ser Met Pro Ala Val Ser Gly Ser Ala Val<br>225 230 235 | | 829 |
| gag caa gtg agc cat gtt gca gcg tcg cag cat aaa cgg aac tcg tgt<br>Glu Gln Val Ser His Val Ala Ala Ser Gln His Lys Arg Asn Ser Cys<br>240 245 250 255 | | 877 |
| agt gaa gcg gtg ttg gca tca agg gac agc gag gtg caa ggc agt agt<br>Ser Glu Ala Val Leu Ala Ser Arg Asp Ser Glu Val Gln Gly Ser Ser<br>260 265 270 | | 925 |
| gct agc agt ccg gca tct tct gaa aca gca gct caa ccc agg gtc att<br>Ala Ser Ser Pro Ala Ser Ser Glu Thr Ala Ala Gln Pro Arg Val Ile<br>275 280 285 | | 973 |
| agg gtt gtt ccc cac acg gca cgc acg gct tca gag tcg gca gca agg<br>Arg Val Val Pro His Thr Ala Arg Thr Ala Ser Glu Ser Ala Ala Arg<br>290 295 300 | | 1021 |
| att ttc cgc tca ata cag atg gag agg aaa caa aac gac ccg tga<br>Ile Phe Arg Ser Ile Gln Met Glu Arg Lys Gln Asn Asp Pro<br>305 310 315 | | 1066 |
| ctggcagata aaaatgaaag aacggaggga gtagactaat ttttgaccg ataattataa | | 1126 |
| tgatcgccgt aaattggctg ccccgcccgc cttatgtttt ttgttcagtg taaatatgct | | 1186 |
| gtgtctgtca gaatgatatg gcatctgtag ctattttggt tctgtcagaa tcatgttgat | | 1246 |
| tggaattaaa aaaaaaaaaa aaaaaa | | 1272 |

<210> SEQ ID NO 57
<211> LENGTH: 317
<212> TYPE: PRT
<213> ORGANISM: Zea mays

<400> SEQUENCE: 57

Asp Val Glu Gln Asn Asp Asp Leu Ser Asp Ser Ser Val Glu Ser Leu
1               5                   10                  15

Pro Gly Met Glu Ile Ser Pro Asp Asp Val Val Ser Ala Ile Gly Pro
            20                  25                  30

Lys His Phe Trp Lys Ala Arg Arg Ala Ile Val Asn Gln Gln Arg Val
        35                  40                  45

Phe Ala Val Gln Val Phe Glu Leu His Arg Leu Ile Lys Val Gln Lys
    50                  55                  60

Leu Ile Ala Ala Ser Pro His Val Leu Ile Glu Gly Asp Pro Cys Leu
65                  70                  75                  80

Gly Lys Ser Leu Ala Val Ser Lys Lys Arg Leu Ala Gly Asp Val Glu
                85                  90                  95

Thr Gln Leu Glu Ser Ala Lys Asn Asp Asp Gly Val Arg Pro Thr Gln
            100                 105                 110

Leu Glu His Ser Lys Glu Lys Thr Glu Ala Asn Gln Pro Ser Pro Ser
        115                 120                 125

```
Gln Asp Glu Gln Ala Ala Thr Asn Gly Asp Val Ala Ala Leu Met His
        130                 135                 140

Thr Pro Ser Asp Asn Lys Gln Lys Ser Trp Cys Ile Pro Ala Pro Pro
145                 150                 155                 160

Ser Gln Trp Leu Ile Pro Val Met Ser Pro Ser Glu Gly Leu Val Tyr
                165                 170                 175

Lys Pro Tyr Thr Gly His Cys Pro Pro Val Gly Ser Leu Leu Ala Pro
            180                 185                 190

Pro Phe Phe Ala Ser Tyr Pro Thr Ser Ser Ser Thr Ala Gly Gly
        195                 200                 205

Asp Phe Met Ser Ser Ala Cys Gly Ala Arg Leu Met Ser Ala Pro Val
    210                 215                 220

Tyr Phe Pro Ser Phe Ser Met Pro Ala Val Ser Gly Ser Ala Val Glu
225                 230                 235                 240

Gln Val Ser His Val Ala Ala Ser Gln His Lys Arg Asn Ser Cys Ser
                245                 250                 255

Glu Ala Val Leu Ala Ser Arg Asp Ser Glu Val Gln Gly Ser Ser Ala
            260                 265                 270

Ser Ser Pro Ala Ser Ser Glu Thr Ala Ala Gln Pro Arg Val Ile Arg
        275                 280                 285

Val Val Pro His Thr Ala Arg Thr Ala Ser Glu Ser Ala Ala Arg Ile
    290                 295                 300

Phe Arg Ser Ile Gln Met Glu Arg Lys Gln Asn Asp Pro
305                 310                 315

<210> SEQ ID NO 58
<211> LENGTH: 1980
<212> TYPE: DNA
<213> ORGANISM: Lycopersicon esculentum
<220> FEATURE:
<221> NAME/KEY: exon
<222> LOCATION: (2)..(1804)
<223> OTHER INFORMATION: portion of exon 1, exon 2, exon 3, and exon 4,
      including stop codon
<220> FEATURE:
<221> NAME/KEY: 3'UTR
<222> LOCATION: (1085)..(1980)
<223> OTHER INFORMATION: partial

<400> SEQUENCE: 58 g cct tct cag aga ttc aac tct ggg gtt ttg cct ctt gat cct aac aat       49
  Pro Ser Gln Arg Phe Asn Ser Gly Val Leu Pro Leu Asp Pro Asn Asn
  1               5                   10                  15 act tca aag atg gcc cct cca tcc tca agc cag ggg agt ggg cat gac        97
Thr Ser Lys Met Ala Pro Pro Ser Ser Ser Gln Gly Ser Gly His Asp
            20                  25                  30 aga agt gga tat ctc cct ata caa cac cct cca tct aga cgt cta gct       145
Arg Ser Gly Tyr Leu Pro Ile Gln His Pro Pro Ser Arg Arg Leu Ala
        35                  40                  45 gat aaa cca cct ggc cac agt tcc gat ccc agt act ctc ttg caa caa       193
Asp Lys Pro Pro Gly His Ser Ser Asp Pro Ser Thr Leu Leu Gln Gln
    50                  55                  60 tat gaa ttg aaa aag aga aca gaa gag gat gac ttt acg gtc ccc atc       241
Tyr Glu Leu Lys Lys Arg Thr Glu Glu Asp Asp Phe Thr Val Pro Ile
65                  70                  75                  80 ttt gtt aat tcc aag ctc ggt cag gcc cat ggg agt cat aat gtg aat       289
Phe Val Asn Ser Lys Leu Gly Gln Ala His Gly Ser His Asn Val Asn
                85                  90                  95
```

```
atg gaa aag ctc tca ccc tct ggt caa ctg ttt tgt cct aat aaa gag    337
Met Glu Lys Leu Ser Pro Ser Gly Gln Leu Phe Cys Pro Asn Lys Glu
        100                 105                 110 ttg gaa gga gtt aca cat cta aca ttg aga caa cag cgc aat agc caa    385
Leu Glu Gly Val Thr His Leu Thr Leu Arg Gln Gln Arg Asn Ser Gln
            115                 120                 125 aac aag gag aat ctc aaa tgt act ctt gct cgt aga gag aaa aca acc    433
Asn Lys Glu Asn Leu Lys Cys Thr Leu Ala Arg Arg Glu Lys Thr Thr
130                 135                 140 tca aac tct gca tcc aag gaa tgc aga ttg gat cct cag gtt ggt tgt    481
Ser Asn Ser Ala Ser Lys Glu Cys Arg Leu Asp Pro Gln Val Gly Cys
145                 150                 155                 160 agt agc ata cct gaa cct gtt aag gga aca tat gat ggc agt tcg tat    529
Ser Ser Ile Pro Glu Pro Val Lys Gly Thr Tyr Asp Gly Ser Ser Tyr
                165                 170                 175 cct agg aaa gaa ttt gta tca taa gag cag tta act gct aat gat ctt    577
Pro Arg Lys Glu Phe Val Ser     Glu Gln Leu Thr Ala Asn Asp Leu
            180                     185                 190 gtt aat gat acg gaa tcc cag gaa gac agg gca cac aaa tca tta caa    625
Val Asn Asp Thr Glu Ser Gln Glu Asp Arg Ala His Lys Ser Leu Gln
                195                 200                 205 aca gga aat ttg gac cga ggt gac gac tta tct gag act tcc aga gtg    673
Thr Gly Asn Leu Asp Arg Gly Asp Asp Leu Ser Glu Thr Ser Arg Val
            210                 215                 220 gaa tct att tct gga aca gac atc tct cct gat gac att gta gga ata    721
Glu Ser Ile Ser Gly Thr Asp Ile Ser Pro Asp Asp Ile Val Gly Ile
225                 230                 235 att ggc tta aag cgt ttc tgg aaa gcc aga aga gca att gtc aac cag    769
Ile Gly Leu Lys Arg Phe Trp Lys Ala Arg Arg Ala Ile Val Asn Gln
240                 245                 250                 255 caa aga gtg ttt gca atc caa gtg ttc gag ttg cat cga cta ata aag    817
Gln Arg Val Phe Ala Ile Gln Val Phe Glu Leu His Arg Leu Ile Lys
                260                 265                 270 gta caa agg ctc att gcc ggg tca cca aat agt tcg ctc gaa gat cct    865
Val Gln Arg Leu Ile Ala Gly Ser Pro Asn Ser Ser Leu Glu Asp Pro
            275                 280                 285 gct tat tta ggc aaa cct tta aag agt tca tcg atc aaa aga ctt cca    913
Ala Tyr Leu Gly Lys Pro Leu Lys Ser Ser Ser Ile Lys Arg Leu Pro
        290                 295                 300 ttg gac tgt att gtt aga gaa tct caa agt gtt ctg aag cgc aag cat    961
Leu Asp Cys Ile Val Arg Glu Ser Gln Ser Val Leu Lys Arg Lys His
305                 310                 315 gat tct gag aag cct cac ttc agg atg gaa cac act gcc gaa agc aat    1009
Asp Ser Glu Lys Pro His Phe Arg Met Glu His Thr Ala Glu Ser Asn
320                 325                 330                 335 gtg gga aag gca tct ctc tct act gtg caa aat ggt agt caa ctc tct    1057
Val Gly Lys Ala Ser Leu Ser Thr Val Gln Asn Gly Ser Gln Leu Ser
            340                 345                 350 agc cac aaa cca ttt tca gga act cca ctg cct aca cct gta aca aat    1105
Ser His Lys Pro Phe Ser Gly Thr Pro Leu Pro Thr Pro Val Thr Asn
        355                 360                 365 gat tct aat gcg ggt cct tgg tgc ttc caa caa cct ccc ggg cac caa    1153
Asp Ser Asn Ala Gly Pro Trp Cys Phe Gln Gln Pro Pro Gly His Gln
370                 375                 380 tgg ttg atc cca gtg atg tct cct tct gag gga ctt gta tac aag cca    1201
Trp Leu Ile Pro Val Met Ser Pro Ser Glu Gly Leu Val Tyr Lys Pro
385                 390                 395
```

```
ttt cct gga cct gga ttc acg agt cct att tgt gga agt ggg cct cca      1249
Phe Pro Gly Pro Gly Phe Thr Ser Pro Ile Cys Gly Ser Gly Pro Pro
400                 405                 410                 415 gga tcg agt cca aca atg ggg aac ttt ttt gct cca aca tat gga gtt      1297
Gly Ser Ser Pro Thr Met Gly Asn Phe Phe Ala Pro Thr Tyr Gly Val
            420                 425                 430 cct gct cct aat cct cac tat caa ggt atg gga gtt cct ttt gca cct      1345
Pro Ala Pro Asn Pro His Tyr Gln Gly Met Gly Val Pro Phe Ala Pro
            435                 440                 445 ccg act ggt cat ggt tac ttt cgg caa tat ggc atg cca gct atg aat      1393
Pro Thr Gly His Gly Tyr Phe Arg Gln Tyr Gly Met Pro Ala Met Asn
            450                 455                 460 cca cca att tca tca act gct agt gaa gaa tcg aac cag tat acc atg      1441
Pro Pro Ile Ser Ser Thr Ala Ser Glu Glu Ser Asn Gln Tyr Thr Met
465                 470                 475 cct ggt tta caa cac cag ttt tct gga gta gtt gat gac gtc aac att      1489
Pro Gly Leu Gln His Gln Phe Ser Gly Val Val Asp Asp Val Asn Ile
480                 485                 490                 495 caa cat cag gac tca agt aat gtt cta aat cag aag aaa gaa aat gtc      1537
Gln His Gln Asp Ser Ser Asn Val Leu Asn Gln Lys Lys Glu Asn Val
            500                 505                 510 ccg gat gtt gta agg tat caa tcc aca aaa gat aat gag gta caa gcc      1585
Pro Asp Val Val Arg Tyr Gln Ser Thr Lys Asp Asn Glu Val Gln Ala
            515                 520                 525 agc agt gca agt agt cct att gag aca gca gga aga aac atg ctc tct      1633
Ser Ser Ala Ser Ser Pro Ile Glu Thr Ala Gly Arg Asn Met Leu Ser
            530                 535                 540 ctt ttt ccc acg tct cca gtt act gac aac cgt gat ggt agc cct cag      1681
Leu Phe Pro Thr Ser Pro Val Thr Asp Asn Arg Asp Gly Ser Pro Gln
545                 550                 555 gct tgt gtg cct gat aat cca gcc aga gtt atc aag gtt gta cct cac      1729
Ala Cys Val Pro Asp Asn Pro Ala Arg Val Ile Lys Val Val Pro His
560                 565                 570                 575 aat gca agg tct gct aca gaa tcc gta gct cgg ata ttt cag tct ata      1777
Asn Ala Arg Ser Ala Thr Glu Ser Val Ala Arg Ile Phe Gln Ser Ile
            580                 585                 590 caa caa gag aga aat aat atg act tag gtttaacaca tctataagta            1824
Gln Gln Glu Arg Asn Asn Met Thr
            595 gcttaccttg tgaatatgac catttgctca tcctggcaaa atgtagtagt ttcagtcaat    1884 ttgttgtatc tttctttcct acagaaagta tgtaatagct gtattttaat ttggttgctg    1944 tagataagca tacctgcaaa aaaaaaaaaa aaaaac                              1980

<210> SEQ ID NO 59
<211> LENGTH: 599
<212> TYPE: PRT
<213> ORGANISM: Lycopersicum esculentum

<400> SEQUENCE: 59

Pro Ser Gln Arg Phe Asn Ser Gly Val Leu Pro Leu Asp Pro Asn Asn
1               5                   10                  15

Thr Ser Lys Met Ala Pro Pro Ser Ser Gln Gly Ser Gly His Asp
            20                  25                  30

Arg Ser Gly Tyr Leu Pro Ile Gln His Pro Pro Ser Arg Arg Leu Ala
            35                  40                  45

Asp Lys Pro Pro Gly His Ser Ser Asp Pro Ser Thr Leu Leu Gln Gln
50                  55                  60
```

-continued

```
Tyr Glu Leu Lys Lys Arg Thr Glu Asp Asp Phe Thr Val Pro Ile
 65              70                  75                  80

Phe Val Asn Ser Lys Leu Gly Gln Ala His Gly Ser His Asn Val Asn
                 85                  90                  95

Met Glu Lys Leu Ser Pro Ser Gly Gln Leu Phe Cys Pro Asn Lys Glu
            100                 105                 110

Leu Glu Gly Val Thr His Leu Thr Leu Arg Gln Gln Arg Asn Ser Gln
            115                 120                 125

Asn Lys Glu Asn Leu Lys Cys Thr Leu Ala Arg Arg Glu Lys Thr Thr
            130                 135                 140

Ser Asn Ser Ala Ser Lys Glu Cys Arg Leu Asp Pro Gln Val Gly Cys
145                 150                 155                 160

Ser Ser Ile Pro Glu Pro Val Lys Gly Thr Tyr Asp Gly Ser Ser Tyr
                165                 170                 175

Pro Arg Lys Glu Phe Val Ser Glu Gln Leu Thr Ala Asn Asp Leu Val
            180                 185                 190

Asn Asp Thr Glu Ser Gln Glu Asp Arg Ala His Lys Ser Leu Gln Thr
            195                 200                 205

Gly Asn Leu Asp Arg Gly Asp Leu Ser Glu Thr Ser Arg Val Glu
    210                 215                 220

Ser Ile Ser Gly Thr Asp Ile Ser Pro Asp Asp Ile Val Gly Ile Ile
225                 230                 235                 240

Gly Leu Lys Arg Phe Trp Lys Ala Arg Arg Ala Ile Val Asn Gln Gln
                245                 250                 255

Arg Val Phe Ala Ile Gln Val Phe Glu Leu His Arg Leu Ile Lys Val
            260                 265                 270

Gln Arg Leu Ile Ala Gly Ser Pro Asn Ser Ser Leu Glu Asp Pro Ala
        275                 280                 285

Tyr Leu Gly Lys Pro Leu Lys Ser Ser Ser Ile Lys Arg Leu Pro Leu
    290                 295                 300

Asp Cys Ile Val Arg Glu Ser Gln Ser Val Leu Lys Arg Lys His Asp
305                 310                 315                 320

Ser Glu Lys Pro His Phe Arg Met Glu His Thr Ala Glu Ser Asn Val
                325                 330                 335

Gly Lys Ala Ser Leu Ser Thr Val Gln Asn Gly Ser Gln Leu Ser Ser
            340                 345                 350

His Lys Pro Phe Ser Gly Thr Pro Leu Pro Thr Pro Val Thr Asn Asp
        355                 360                 365

Ser Asn Ala Gly Pro Trp Cys Phe Gln Gln Pro Pro Gly His Gln Trp
370                 375                 380

Leu Ile Pro Val Met Ser Pro Ser Glu Gly Leu Val Tyr Lys Pro Phe
385                 390                 395                 400

Pro Gly Pro Gly Phe Thr Ser Pro Ile Cys Gly Ser Gly Pro Pro Gly
                405                 410                 415

Ser Ser Pro Thr Met Gly Asn Phe Phe Ala Pro Thr Tyr Gly Val Pro
            420                 425                 430

Ala Pro Asn Pro His Tyr Gln Gly Met Gly Val Pro Phe Ala Pro Pro
            435                 440                 445

Thr Gly His Gly Tyr Phe Arg Gln Tyr Gly Met Pro Ala Met Asn Pro
        450                 455                 460

Pro Ile Ser Ser Thr Ala Ser Glu Glu Ser Asn Gln Tyr Thr Met Pro
465                 470                 475                 480
```

```
Gly Leu Gln His Gln Phe Ser Gly Val Asp Asp Val Asn Ile Gln
            485                 490                 495

His Gln Asp Ser Ser Asn Val Leu Asn Gln Lys Lys Glu Asn Val Pro
            500                 505                 510

Asp Val Val Arg Tyr Gln Ser Thr Lys Asp Asn Glu Val Gln Ala Ser
            515                 520                 525

Ser Ala Ser Ser Pro Ile Glu Thr Ala Gly Arg Asn Met Leu Ser Leu
            530                 535                 540

Phe Pro Thr Ser Pro Val Thr Asp Asn Arg Asp Gly Ser Pro Gln Ala
545                 550                 555                 560

Cys Val Pro Asp Asn Pro Ala Arg Val Ile Lys Val Val Pro His Asn
                565                 570                 575

Ala Arg Ser Ala Thr Glu Ser Val Ala Arg Ile Phe Gln Ser Ile Gln
            580                 585                 590

Gln Glu Arg Asn Asn Met Thr
            595
```

<210> SEQ ID NO 60
<211> LENGTH: 1972
<212> TYPE: DNA
<213> ORGANISM: Brassica sp.
<220> FEATURE:
<221> NAME/KEY: exon
<222> LOCATION: (1)..(147)
<223> OTHER INFORMATION: partial
<220> FEATURE:
<221> NAME/KEY: Intron
<222> LOCATION: (148)..(343)
<220> FEATURE:
<221> NAME/KEY: exon
<222> LOCATION: (344)..(792)
<220> FEATURE:
<221> NAME/KEY: Intron
<222> LOCATION: (793)..(1504)
<220> FEATURE:
<221> NAME/KEY: exon
<222> LOCATION: (1505)..(1556)
<220> FEATURE:
<221> NAME/KEY: Intron
<222> LOCATION: (1557)..(1648)
<220> FEATURE:
<221> NAME/KEY: exon
<222> LOCATION: (1649)..(1972)

<400> SEQUENCE: 60

```
aaa gga gga gga cct cga gct cct cct aga aac aag atg gct ctc tac        48
Lys Gly Gly Gly Pro Arg Ala Pro Pro Arg Asn Lys Met Ala Leu Tyr
1               5                   10                  15 gag cac ctc acc acc cct tct cac agg ttt act gat cat agt tcc tcg        96
Glu His Leu Thr Thr Pro Ser His Arg Phe Thr Asp His Ser Ser Ser
                20                  25                  30 cca cgt cac acc aac act ctc ttt cct cct cct cct gga cca tct aac       144
Pro Arg His Thr Asn Thr Leu Phe Pro Pro Pro Pro Gly Pro Ser Asn
            35                  40                  45 cag gtactactga gttttagta ataatatata ttagttacag caaatcttaa             197
Gln tttcttgctg tgtcttatta ccatgtttcg tttgtggaaa tgattatctt ttaaagctat     257
aaccttcttg ttatgctgaa tagtttcagt agaagattat atagtgtatg tgggacattg     317
```

```
gaaataatta tcttttatt ctgcag cct tgt ggg gtg gag aga aac ttg act       370
                           Pro Cys Gly Val Glu Arg Asn Leu Thr
                            50                  55 tcc cag cat ctt gat tct tca gct tct ggc cat gta acc caa atg tcc       418
Ser Gln His Leu Asp Ser Ser Ala Ser Gly His Val Thr Gln Met Ser
 60                  65                  70 tcc atg gaa aat gtg aca act tta gca cat cgt cgt ggt gat caa agg       466
Ser Met Glu Asn Val Thr Thr Leu Ala His Arg Arg Gly Asp Gln Arg
 75                  80                  85                  90 aaa acg cta aga gag gaa gat gat ttt gcg gtt cct gta tat gtt aat       514
Lys Thr Leu Arg Glu Glu Asp Asp Phe Ala Val Pro Val Tyr Val Asn
                 95                 100                 105 gat agc tca aga aga ttt caa tgt cct ctt gaa aag tca gca tcg ggt       562
Asp Ser Ser Arg Arg Phe Gln Cys Pro Leu Glu Lys Ser Ala Ser Gly
            110                 115                 120 tgt gaa aga gtt aat gct tct tgt gag aca gag tct aca agt agt agg       610
Cys Glu Arg Val Asn Ala Ser Cys Glu Thr Glu Ser Thr Ser Ser Arg
        125                 130                 135 tta gac cat gaa act gga gtg atg gaa act gat gat gga gtt gaa tct       658
Leu Asp His Glu Thr Gly Val Met Glu Thr Asp Asp Gly Val Glu Ser
140                 145                 150 cat ggc aat cct aat gac gtc gat gat gat gat gat gat gat tcg ata       706
His Gly Asn Pro Asn Asp Val Asp Asp Asp Asp Asp Asp Asp Ser Ile
155                 160                 165                 170 tcc agc ata gac gtc tct tct gat gaa gtt gtg gga gta tta ggt caa       754
Ser Ser Ile Asp Val Ser Ser Asp Glu Val Val Gly Val Leu Gly Gln
                175                 180                 185 aac cgk ttc tgg aga gca agg aar gct atk gcc aag aa  gtycctcata        802
Asn Arg Phe Trp Arg Ala Arg Lys Ala Xaa Ala Lys Asn
            190                 195 gacttttggt gaactggtaa ggaatttttt gggtctttct ctgctgtttt aatgcttaaa     862
tgatgcaatg gtttgctcac aacatacata tatgattata actctgcttt atattttgaa    922
aaagaccaga tttggtttat ttttgattga gaagtgataa ttttttagtg aagaaacccc     982
ctgactcctc caaaaattga aggttcccgc cgagacagtt aatggatttt gcatctgctt   1042
gctggaacat gtccctgtcc ctgtctcggt ttggtatttg cttttattct gcattttccc   1102
ttcttgtcat tcaacgggtt gaaccaggta gttaaccata cataaagcta gttatgtgtc   1162
ttatgaaaat gaagaattat agtagcagag gttgtaaact atggagtttt ctatggattt   1222
tagactctgt tactcaggtt ttaaggttct atgtaaggta tcaattaaac ccaccccttg   1282
cataatgtct tcagttttc ttcttctatt atttatgcct ttctctgtgt tttttgacgc    1342
attgatttgc ttcttcatca ttgttggtta gaggcttctt gcttctttt ttttccgatt    1402 ctactgttct attatttgtt caaccgaaac tatatctatc tctctttgtg gaacttttct   1462
tatgggtcat cttcttgatc tgaccttgtt tctccgtaac ag t caa caa aga ata    1517
                                               Gln Gln Arg Ile
                                                       200 ttt gcg gtt caa tta ttt gag ttg cac agg ctr att aag gtaaaactca       1566
Phe Ala Val Gln Leu Phe Glu Leu His Arg Xaa Ile Lys
205                 210                 215 ttcagaaaac ttctcctacg tttcatgaat atttgttttg tgcaaaccta gtcaactgta   1626
ctttgttttc actataatca ag gtt caa aga ctt att gct tca tca tcg gat   1678
                         Val Gln Arg Leu Ile Ala Ser Ser Ser Asp
                                     220                 225
```

```
gtc ttg ctc gat gag atc agt tat ctt gga aat gtt cca gtg aag aag      1726
Val Leu Leu Asp Glu Ile Ser Tyr Leu Gly Asn Val Pro Val Lys Lys
            230                 235                 240 ctt ctt ccc tct gaa ttt ata tta aag cct cct cct cta cca cag gtt      1774
Leu Leu Pro Ser Glu Phe Ile Leu Lys Pro Pro Pro Leu Pro Gln Val
        245                 250                 255 acc aaa cac aga agc agc gac tcc gag aag act gac caa aat aaa atg      1822
Thr Lys His Arg Ser Ser Asp Ser Glu Lys Thr Asp Gln Asn Lys Met
    260                 265                 270 gaa tcc tca gct gag aac gta gtc ggg aag tcg tca aac caa ggt cag      1870
Glu Ser Ser Ala Glu Asn Val Val Gly Lys Ser Ser Asn Gln Gly Gln
275                 280                 285                 290 cag cat caa ccg tcc aac tac atg cct ttt gcg agc aac cca cca gct      1918
Gln His Gln Pro Ser Asn Tyr Met Pro Phe Ala Ser Asn Pro Pro Ala
                295                 300                 305 gca aat gga tgt tac tat cct cct cag cat cct cct ccc tct gga gga      1966
Ala Asn Gly Cys Tyr Tyr Pro Pro Gln His Pro Pro Pro Ser Gly Gly
            310                 315                 320 aat cag                                                              1972
Asn Gln <210> SEQ ID NO 61
<211> LENGTH: 324
<212> TYPE: PRT
<213> ORGANISM: Brassica sp.
<220> FEATURE:
<221> NAME/KEY: misc_feature
<222> LOCATION: (188)..(188)
<223> OTHER INFORMATION: Xaa = uncertain amino acid residue
<220> FEATURE:
<221> NAME/KEY: misc_feature
<222> LOCATION: (194)..(194)
<223> OTHER INFORMATION: Xaa = uncertain amino acid residue
<220> FEATURE:
<221> NAME/KEY: misc_feature
<222> LOCATION: (196)..(196)
<223> OTHER INFORMATION: Xaa = uncertain amino acid residue
<220> FEATURE:
<221> NAME/KEY: misc_feature
<222> LOCATION: (214)..(214)
<223> OTHER INFORMATION: Xaa = uncertain amino acid residue

<400> SEQUENCE: 61

Lys Gly Gly Gly Pro Arg Ala Pro Pro Arg Asn Lys Met Ala Leu Tyr
1               5                   10                  15

Glu His Leu Thr Thr Pro Ser His Arg Phe Thr Asp His Ser Ser Ser
            20                  25                  30

Pro Arg His Thr Asn Thr Leu Phe Pro Pro Pro Gly Pro Ser Asn
        35                  40                  45

Gln Pro Cys Gly Val Glu Arg Asn Leu Thr Ser Gln His Leu Asp Ser
    50                  55                  60

Ser Ala Ser Gly His Val Thr Gln Met Ser Ser Met Glu Asn Val Thr
65                  70                  75                  80

Thr Leu Ala His Arg Arg Gly Asp Gln Arg Lys Thr Leu Arg Glu Glu
                85                  90                  95

Asp Asp Phe Ala Val Pro Val Tyr Val Asn Asp Ser Arg Arg Phe
            100                 105                 110

Gln Cys Pro Leu Glu Lys Ser Ala Ser Gly Cys Glu Arg Val Asn Ala
        115                 120                 125
```

```
Ser Cys Glu Thr Glu Ser Thr Ser Ser Arg Leu Asp His Glu Thr Gly
    130                 135                 140

Val Met Glu Thr Asp Asp Gly Val Glu Ser His Gly Asn Pro Asn Asp
145                 150                 155                 160

Val Asp Asp Asp Asp Asp Asp Ser Ile Ser Ser Ile Asp Val Ser
                165                 170                 175

Ser Asp Glu Val Val Gly Val Leu Gly Gln Asn Xaa Phe Trp Arg Ala
            180                 185                 190

Arg Xaa Ala Xaa Ala Lys Asn Gln Gln Arg Ile Phe Ala Val Gln Leu
    195                 200                 205

Phe Glu Leu His Arg Xaa Ile Lys Val Gln Arg Leu Ile Ala Ser Ser
    210                 215                 220

Ser Asp Val Leu Leu Asp Glu Ile Ser Tyr Leu Gly Asn Val Pro Val
225                 230                 235                 240

Lys Lys Leu Leu Pro Ser Glu Phe Ile Leu Lys Pro Pro Leu Pro
                245                 250                 255

Gln Val Thr Lys His Arg Ser Ser Asp Ser Glu Lys Thr Asp Gln Asn
                260                 265                 270

Lys Met Glu Ser Ser Ala Glu Asn Val Val Gly Lys Ser Ser Asn Gln
    275                 280                 285

Gly Gln Gln His Gln Pro Ser Asn Tyr Met Pro Phe Ala Ser Asn Pro
    290                 295                 300

Pro Ala Ala Asn Gly Cys Tyr Tyr Pro Pro Gln His Pro Pro Pro Ser
305                 310                 315                 320

Gly Gly Asn Gln

<210> SEQ ID NO 62
<211> LENGTH: 505
<212> TYPE: DNA
<213> ORGANISM: Brassica
<220> FEATURE:
<221> NAME/KEY: exon
<222> LOCATION: (2)..(505)

<400> SEQUENCE: 62 a ccc ggt cca gat ccg ggg cac acg ggg ccg gtc tgt gga ggg tat tat    49
  Pro Gly Pro Asp Pro Gly His Thr Gly Pro Val Cys Gly Gly Tyr Tyr
  1               5                  10                  15 ggt cat ttc atg cct gca cca atg ttc atg ggt ggt ggt ggt ggt cag      97
Gly His Phe Met Pro Ala Pro Met Phe Met Gly Gly Gly Gly Gly Gln
            20                  25                  30 cct cct ccg ttt cac ccg ggc atg gga ttc cya tct cat ggt aat ggc     145
Pro Pro Pro Phe His Pro Gly Met Gly Phe Xaa Ser His Gly Asn Gly
        35                  40                  45 tac ttt cct cca tat ggt ggt atc atg atg aac cct tac tat tcc gga    193
Tyr Phe Pro Pro Tyr Gly Gly Ile Met Met Asn Pro Tyr Tyr Ser Gly
    50                  55                  60 cra caa caa caa caa caa ccc aat gag caa atg aac aac aac atc caa    241
Xaa Gln Gln Gln Gln Gln Pro Asn Glu Gln Met Asn Asn Asn Ile Gln
65                  70                  75                  80 caa cag agc tca gtg aat gaa gcg act tca caa caa caa cag cca acg    289
Gln Gln Ser Ser Val Asn Glu Ala Thr Ser Gln Gln Gln Gln Pro Thr
                85                  90                  95
```

```
aaa tct tat cct cgg gct aaa aag agc agg caa gag gga atc tct ggt    337
Lys Ser Tyr Pro Arg Ala Lys Lys Ser Arg Gln Glu Gly Ile Ser Gly
        100                 105                 110 aag aag aag tcc ttt caa cca ttc tca gcg gtt gat gat gtt cat gat    385
Lys Lys Lys Ser Phe Gln Pro Phe Ser Ala Val Asp Asp Val His Asp
            115                 120                 125 gac aag atc aac aat gct gca caa cct act gag gaa atg atg acg aca    433
Asp Lys Ile Asn Asn Ala Ala Gln Pro Thr Glu Glu Met Met Thr Thr
    130                 135                 140 acc aca acc aca aca aca act gtg act cag aca acg aga gat gga gca    481
Thr Thr Thr Thr Thr Thr Thr Val Thr Gln Thr Thr Arg Asp Gly Ala
145                 150                 155                 160 gga gtg acg aga gtg atc aag gtg                                    505
Gly Val Thr Arg Val Ile Lys Val
                165

<210> SEQ ID NO 63
<211> LENGTH: 168
<212> TYPE: PRT
<213> ORGANISM: Brassica sp.
<220> FEATURE:
<221> NAME/KEY: misc_feature
<222> LOCATION: (43)..(43)
<223> OTHER INFORMATION: Xaa = uncertain amino acid residue
<220> FEATURE:
<221> NAME/KEY: misc_feature
<222> LOCATION: (65)..(65)
<223> OTHER INFORMATION: Xaa = uncertain amino acid residue

<400> SEQUENCE: 63

Pro Gly Pro Asp Pro Gly His Thr Gly Pro Val Cys Gly Gly Tyr Tyr
1               5                   10                  15

Gly His Phe Met Pro Ala Pro Met Phe Met Gly Gly Gly Gly Gly Gln
            20                  25                  30

Pro Pro Pro Phe His Pro Gly Met Gly Phe Xaa Ser His Gly Asn Gly
        35                  40                  45

Tyr Phe Pro Pro Tyr Gly Gly Ile Met Met Asn Pro Tyr Tyr Ser Gly
    50                  55                  60

Xaa Gln Gln Gln Gln Pro Asn Glu Gln Met Asn Asn Asn Ile Gln
65                  70                  75                  80

Gln Gln Ser Ser Val Asn Glu Ala Thr Ser Gln Gln Gln Pro Thr
            85                  90                  95

Lys Ser Tyr Pro Arg Ala Lys Lys Ser Arg Gln Glu Gly Ile Ser Gly
        100                 105                 110

Lys Lys Lys Ser Phe Gln Pro Phe Ser Ala Val Asp Asp Val His Asp
    115                 120                 125

Asp Lys Ile Asn Asn Ala Ala Gln Pro Thr Glu Glu Met Met Thr Thr
    130                 135                 140

Thr Thr Thr Thr Thr Thr Thr Val Thr Gln Thr Thr Arg Asp Gly Ala
145                 150                 155                 160

Gly Val Thr Arg Val Ile Lys Val
                165

<210> SEQ ID NO 64
<211> LENGTH: 36
<212> TYPE: DNA
<213> ORGANISM: synthetic oligonucleotide
<220> FEATURE:
<221> NAME/KEY: misc_feature
<222> LOCATION: (28)..(28)
<223> OTHER INFORMATION: n = any nucleic acid residue
```

```
<400> SEQUENCE: 64
tgttatgtct ccttctgaag gactgrtnta yaarcc                               36

<210> SEQ ID NO 65
<211> LENGTH: 35
<212> TYPE: DNA
<213> ORGANISM: synthetic oligonucleotide
<220> FEATURE:
<221> NAME/KEY: misc_feature
<222> LOCATION: (30)..(30)
<223> OTHER INFORMATION: n = any nucleic acid
<220> FEATURE:
<221> NAME/KEY: misc_feature
<222> LOCATION: (33)..(33)
<223> OTHER INFORMATION: n = any nucleic acid

<400> SEQUENCE: 65
gcagattcag aagcagttct agcaktrtgn ggnac                                35

<210> SEQ ID NO 66
<211> LENGTH: 35
<212> TYPE: DNA
<213> ORGANISM: synthetic oligonucleotide
<220> FEATURE:
<221> NAME/KEY: misc_feature
<222> LOCATION: (33)..(33)
<223> OTHER INFORMATION: n = any nucleic acid

<400> SEQUENCE: 66
caaagagttt ttgctgttca agttttygar ytnca                                35

<210> SEQ ID NO 67
<211> LENGTH: 20
<212> TYPE: DNA
<213> ORGANISM: synthetic oligonucleotide

<400> SEQUENCE: 67
tcaatcagtc acctgggcat                                                 20

<210> SEQ ID NO 68
<211> LENGTH: 35
<212> TYPE: DNA
<213> ORGANISM: synthetic oligonucleotide
<220> FEATURE:
<221> NAME/KEY: misc_feature
<222> LOCATION: (9)..(9)
<223> OTHER INFORMATION: n = any nucleic acid

<400> SEQUENCE: 68
cartggytnr ttcctgttat gtctccttct gaagg                                35
```